US011241460B2

(12) United States Patent
Lanza et al.

(10) Patent No.: US 11,241,460 B2
(45) Date of Patent: *Feb. 8, 2022

(54) PHOTORECEPTORS AND PHOTORECEPTOR PROGENITORS PRODUCED FROM PLURIPOTENT STEM CELLS

(71) Applicant: Astellas Institute for Regenerative Medicine, Marlborough, MA (US)

(72) Inventors: Robert P. Lanza, Clinton, MA (US); Shi-Jiang Lu, Shrewsbury, MA (US); Wei Wang, Rochester, MN (US)

(73) Assignee: Astellas Institute for Regenerative Medicine, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,788

(22) Filed: Jul. 2, 2018

(65) Prior Publication Data

US 2019/0060370 A1 Feb. 28, 2019

Related U.S. Application Data

(63) Continuation of application No. 14/857,780, filed on Sep. 17, 2015, now abandoned, which is a continuation-in-part of application No. 14/489,415, filed on Sep. 17, 2014, which is a continuation-in-part of application No. 14/214,598, filed on Mar. 14, 2014, now Pat. No. 10,307,444, and a continuation-in-part of application No. PCT/US2014/029790, filed on Mar. 14, 2014.

(60) Provisional application No. 61/793,168, filed on Mar. 15, 2013, provisional application No. 61/793,168, filed on Mar. 15, 2013.

(51) Int. Cl.

| *A01N 63/00* | (2020.01) |
| *A01N 65/00* | (2009.01) |
| *A61K 35/30* | (2015.01) |
| *A61K 9/00* | (2006.01) |
| *C12N 5/0797* | (2010.01) |
| *C12N 5/0793* | (2010.01) |
| *A61K 35/545* | (2015.01) |

(52) U.S. Cl.
CPC ............ *A61K 35/30* (2013.01); *A61K 9/0048* (2013.01); *A61K 9/0051* (2013.01); *A61K 35/545* (2013.01); *C12N 5/062* (2013.01); *C12N 5/0623* (2013.01); *C12N 2501/105* (2013.01); *C12N 2501/13* (2013.01); *C12N 2501/235* (2013.01); *C12N 2501/33* (2013.01); *C12N 2501/385* (2013.01); *C12N 2501/392* (2013.01); *C12N 2501/727* (2013.01); *C12N 2501/998* (2013.01); *C12N 2501/999* (2013.01); *C12N 2506/02* (2013.01)

(58) Field of Classification Search
CPC ..................................................... A61K 35/30
See application file for complete search history.

(56) References Cited

U.S. PATENT DOCUMENTS

| 6,465,248 | B1 | 10/2002 | Commissiong et al. |
| 7,531,354 | B2 | 5/2009 | Stice et al. |
| 7,541,186 | B2 | 6/2009 | Reh et al. |
| 7,794,704 | B2 | 9/2010 | Klimanskaya |
| 9,133,435 | B2 | 9/2015 | Takahashi et al. |
| 9,249,390 | B2 | 2/2016 | Zhu et al. |
| 10,307,444 | B2 | 6/2019 | Lanza et al. |
| 2003/0166276 | A1 | 9/2003 | Carpenter et al. |
| 2010/0105137 | A1 | 4/2010 | Takahashi et al. |
| 2010/0136537 | A1 | 6/2010 | Swaroop et al. |
| 2011/0081719 | A1 | 4/2011 | Gamm et al. |
| 2011/0223140 | A1 | 9/2011 | Park et al. |
| 2014/0004086 | A1 | 1/2014 | Paek et al. |
| 2014/0294778 | A1 | 3/2014 | Lanza et al. |
| 2014/0186309 | A1 | 7/2014 | Klassen et al. |
| 2016/0030490 | A1 | 2/2016 | Lanza et al. |
| 2016/0175361 | A1 | 6/2016 | Lanza et al. |
| 2016/0175362 | A1 | 6/2016 | Lanza et al. |
| 2018/0117091 | A1 | 5/2018 | Small et al. |
| 2019/0290701 | A1 | 9/2019 | Lanza et al. |
| 2019/0321414 | A1 | 10/2019 | Lanza et al. |

FOREIGN PATENT DOCUMENTS

| CN | 102204930 A | 10/2011 |
| CN | 102712900 A | 10/2012 |
| EP | 2383333 B1 | 5/2015 |
| JP | 5441099 B2 | 3/2014 |
| KR | 10-2263956 B1 | 6/2021 |
| WO | 1996/030403 A1 | 10/1996 |
| WO | WO 99/55838 A1 | 11/1999 |
| WO | 2002/074176 A1 | 9/2002 |

(Continued)

OTHER PUBLICATIONS

Pearson (Mar. 2014, Biotechnology Advances, 32:485-491).*
[No Author Listed], ARVO Annual Meeting Abstract Search and Program Planner. BIOSIS [online], BIOSIS Accession No. 2012:522138. May 2011;2011:5989. 1 page.
Ahmad, Mash-1 is expressed during ROD photoreceptor differentiation and binds an E-box, E(opsin)-1 in the rat opsin gene. Brain Res Dev Brain Res. Dec. 21, 1995;90(1-2):184-9.
Akagi et al., Requirement of multiple basic helix-loop-helix genes for retinal neuronal subtype specification. J Biol Chem. Jul. 2004; 279;28492-98.
Meyer et al., Modeling early retinal development with human embryonic and induced pluripotent stem cells. Proc Natl Acad Sci U S A. Sep. 29, 2009;106(39):16698-703. doi: 10.1073/pnas. 0905245106. Epub Aug. 25, 2009. Supporting Information 11 pages.

(Continued)

*Primary Examiner* — Valarie E Bertoglio
(74) *Attorney, Agent, or Firm* — Wolf, Greenfield & Sacks, P.C.

(57) ABSTRACT

Methods are provided for the production of photoreceptor cells and photoreceptor progenitor cells from pluripotent stem cells. Additionally provided are compositions of photoreceptor cells and photoreceptor cells, as well as methods for the therapeutic use thereof. Exemplary methods may produce substantially pure cultures of photoreceptor cells and/or photoreceptor cells.

23 Claims, 43 Drawing Sheets

(56) References Cited

FOREIGN PATENT DOCUMENTS

| | | |
|---|---|---|
| WO | 2002/076386 A2 | 10/2002 |
| WO | 2004/007749 A2 | 1/2004 |
| WO | 2005/123902 A1 | 12/2005 |
| WO | 2007/100692 A2 | 9/2007 |
| WO | WO 2008/045952 A2 | 4/2008 |
| WO | WO 2008/087917 A1 | 7/2008 |
| WO | 2011/028524 A1 | 3/2011 |
| WO | WO 2011/043591 A2 | 4/2011 |
| WO | 2011/055855 A1 | 5/2011 |
| WO | 2013/077425 A1 | 5/2013 |
| WO | 2013/163296 A1 | 10/2013 |
| WO | 2013/183774 A1 | 12/2013 |
| WO | 2014/174492 A1 | 10/2014 |
| WO | 2015/025967 A1 | 2/2015 |
| WO | 2015/068505 A1 | 5/2015 |
| WO | 2015/087614 A1 | 6/2015 |
| WO | 2015/107738 A1 | 7/2015 |
| WO | 2015/109148 A1 | 7/2015 |
| WO | 2015/121687 A1 | 8/2015 |
| WO | 2016/063986 A1 | 4/2016 |
| WO | 2016/160718 A1 | 10/2016 |
| WO | 2017/043604 A1 | 3/2017 |
| WO | 2017/164992 A1 | 9/2017 |
| WO | 2017/176810 A1 | 10/2017 |
| WO | 2017/183732 A1 | 10/2017 |
| WO | 2018/055131 A1 | 3/2018 |
| WO | 2018/097253 A1 | 3/2018 |
| WO | 2018/132802 A1 | 7/2018 |
| WO | 2018/149985 A1 | 8/2018 |
| WO | 2018/154295 A1 | 8/2018 |
| WO | 2019/017492 A1 | 1/2019 |
| WO | 2019/028088 A1 | 2/2019 |
| WO | 2019/032999 A1 | 2/2019 |
| WO | 2019/054514 A1 | 3/2019 |
| WO | 2019/054515 A1 | 3/2019 |
| WO | 2019/138250 A1 | 7/2019 |
| WO | 2019/170766 A1 | 9/2019 |
| WO | 2019/210320 A2 | 10/2019 |
| WO | 2019/217630 A1 | 11/2019 |

OTHER PUBLICATIONS

Neeley, A Brief History of Spheroids. ThermoFisher Scientific. Aug. 24, 2016. https://www.thermofisher.com/blog/cellculture/a-brief-history-of-spheroids-and-3d-cell-culture/ [last accessed Dec. 28, 2018].

Ng et al., Two transcription factors can direct three photoreceptor outcomes from rod precursor cells in mouse retinal development. J Neurosci. Aug. 3, 2011;31:11118-25.

PCT/US2014/029790, Jul. 11, 2014, International Search Report and Written Opinion.

PCT/US2014/029790, Sep. 24, 2015, International Preliminary Report on Patentability.

EP 14764825.7, Oct. 14, 2016, Extended European Search Report.

Agathocleous et al., From progenitors to differentiated cells in the vertebrate retina. Annu Rev Cell Dev Biol. 2009;25:45-69. doi: 10.1146/annurev.cellbio.042308.113259. Abstract Only.

Amirpour et al., Differentiation of human embryonic stem cell-derived retinal progenitors into retinal cells by Sonic hedgehog and/or retinal pigmented epithelium and transplantation into the subretinal space of sodium iodate-injected rabbits. Stem Cells Dev. Jan. 2012;21(1):42-53. doi: 10.1089/scd.2011.0073.

Barber et al., Repair of the degenerate retina by photoreceptor transplantation. Proc Natl Acad Sci U S A. Jan. 2, 2013;110(1):354-9. doi: 10.1073/pnas.1212677110. Epub Dec. 17, 2012.

Barnea-Cramer et al., Function of human pluripotent stem cell-derived photoreceptor progenitors in blind mice. Sci Rep. Jul. 13, 2016;6:29784. doi: 10.1038/srep29784.

Bäumer et al., Retinal pigmented epithelium determination requires the redundant activities of Pax2 and Pax6. Development. Jul. 2003;130(13):2903-15.

Bez et al., Neurosphere and neurosphere-forming cells: morphological and ultrastructural characterization. Brain Research. 2003;993:18-29.

Boucherie et al., Brief report: self-organizing neuroepithelium from human pluripotent stem cells facilitates derivation of photoreceptors. Stem Cells. Feb. 2013;31(2):408-14. doi: 10.1002/stem.1268.

Busskamp et al., Genetic reactivation of cone photoreceptors restores visual responses in retinitis pigmentosa. Science. Jul. 23, 2010;329(5990):413-7. doi: 10.1126/science.1190897. Epub Jun. 24, 2010. Abstract only.

Carroll et al., Functional photoreceptor loss revealed with adaptive optics: an alternate cause of color blindness. Proc Natl Acad Sci U S A. Jun. 1, 2004;101(22):8461-6. Epub May 17, 2004.

Chung et al., Human embryonic stem cell lines generated without embryo destruction. Cell Stem Cell. Feb. 7, 2008;2(2):113-7. doi: 10.1016/j.stem.2007.12.013.

Cornish et al., The role of opsin expression and apoptosis in determination of cone types in human retina. Exp Eye Res. Jun. 2004;78(6):1143-54. Abstract only.

Cramer et al., Translating induced pluripotent stem cells from bench to bedside: application to retinal diseases. Curr Gene Ther. Apr. 2013;13(2):139-51. Review.

Da Silva et al., Smart thermoresponsive coatings and surfaces for tissue engineering: switching cell-material boundaries. Trends Biotechnol. Dec. 2007;25(12):577-83. Epub Nov. 8, 2007. Abstract Only.

Eberle et al., Increased integration of transplanted CD73-positive photoreceptor precursors into adult mouse retina. Investigative Opthalmology & Visual Science. Aug. 2011;52:6462-71. doi:10.1167/iovs.11-7399.

Eberle et al., Subretinal transplantation of MACS purified photoreceptor precursor cells into the adult mouse retina. J Vis Exp. Feb. 22, 2014;(84):e50932. doi: 10.3791/50932.

Eiraku et al., Mouse embryonic stem cell culture for generation of three-dimensional retinal and cortical tissues. Nat Protoc. Dec. 15, 2011;7(1):69-79. doi: 10.1038/nprot.2011.429. Abstract only.

Fischer et al., Transdifferentiation of pigmented epithelial cells: a source of retinal stem cells? Dev Neurosci. 2001;23(4-5):268-76. Abstract Only.

Gamm et al., Directed differentiation of human induced pluripotent stem cells: a retina perspective. Regen Med. May 2010;5(3):315-7. doi: 10.2217/rme.10.28.

Gonzalez-Cordero et al., Photoreceptor precursors derived from three-dimensional embryonic stem cell cultures integrate and mature within adult degenerate retina. Nat Biotechnol. Aug. 2013;31(8):741-7. doi: 10.1038/nbt.2643. Epub Jul. 21, 2013.

Gouras et al., Reconstruction of degenerate rd mouse retina by transplantation of transgenic photoreceptors. Investigative Opthalmology &Visual Science. Aug. 1992;33:2579-86.

Haider et al., Mutation of a nuclear receptor gene, NR2E3, causes enhanced S cone syndrome, a disorder of retinal cell fate. Nat Genet. Feb. 2000;24(2):127-31. Abstract only.

Hambright et al., Long-term survival and differentiation of retinal neurons derived from human embryonic stem cell lines in un-immunosuppressed mouse retina. Molec Vis. Apr. 12, 2012;18:920-36.

Hansson et al., Commentary: isolated stem cells—patentable as cultural artifacts? Stem Cells. Jun. 2007;25(6):1507-10. Epub Mar. 8, 2007. Abstract only.

Hartong et al., Retinitis pigmentosa. Lancet. Nov. 18, 2006;368(9549):1795-809. Review. Abstract only.

Harvey et al., The early phase of horizontal optokinetic responses in the pigmented rat and the effects of lesions of the visual cortex. Vision Res. Jun. 1997;37(12):1615-25.

Hirami et al., Generation of retinal cells from mouse and human induced pluripotent stem cells. Neurosci Lett. Jul. 24, 2009;458(3):126-31. doi: 10.1016/j.neulet.2009.04.035. Epub Apr. 18, 2009.

Hsiue et al., A novel strategy for corneal endothelial reconstruction with a bioengineered cell sheet. Transplantation. Feb. 15, 2006;81(3):473-6. Abstract Only.

(56) References Cited

OTHER PUBLICATIONS

Ide et al. Structural characterization of bioengineered human corneal endothelial cell sheets fabricated on temperature-responsive culture dishes. Biomaterials. Feb. 2006;27(4):607-14. Epub Aug. 15, 2005. Abstract Only.
Ikeda et al., Generation of Rx+/Pax6+ neural retinal precursors from embryonic stem cells. Proc Natl Acad Sci U S A. Aug. 9, 2005;102(32):11331-6. Epub Aug. 2, 2005.
Inoue et al., Subretinal transplantation of bone marrow mesenchymal stem cells delays retinal degeneration in the RCS rat model of retinal degeneration. Exp Eye Res. Aug. 2007;85(2):234-41. Epub May 6, 2007. Abstract Only.
Jin et al., Integration-free induced pluripotent stem cells derived from retinitis pigmentosa patient for disease modeling. Stem Cells Transl Med. Jun. 2012;1(6):503-9. doi: 10.5966/sctm.2012-0005. Epub Jun. 1, 2012.
Jonas et al., Intravitreal autologous bone marrow-derived mononuclear cell transplantation: a feasibility report. Acta Ophthalmol. Mar. 2008;86(2):225-6. Epub Sep. 26, 2007.
Klassen et al., Multipotent retinal progenitors express developmental markers, differentiate into retinal neurons, and preserve light-mediated behavior. Invest Ophthalmol Vis Sci. Nov. 2004;45(11):4167-73.
Klimanskaya et al., Human embryonic stem cell lines derived from single blastomeres. Nature. Nov. 23, 2006;444(7118):481-5. Erratum in: Nature. Nov. 23, 2006;444(7118):512. Nature. Mar. 15, 2007;446(7133):342.
Koso et al., CD73, a novel cell surface antigen that characterizes retinal photoreceptor precursor cells. Invest Ophthalmol Vis Sci. Nov. 2009;50(11):5411-8. doi: 10.1167/iovs.08-3246. Epub Jun. 10, 2009.
Kwan et al., Photoreceptor layer reconstruction in a rodent model of retinal degeneration. Exp Neurol. Sep. 1999;159(1):21-33. Abstract only.
La Torre et al., Production and transplantation of retinal cells from human and mouse embryonic stem cells. Methods Mol Biol. 2012;884:229-46. doi: 10.1007/978-1-61779-848-1_16. Abstract only.
Lakowski et al., Cone and rod photoreceptor transplantation in models of the childhood retinopathy Leber congenital amaurosis using flow-sorted Crx-positive donor cells. Hum MolGenet. Dec. 1, 2010;19(23):4545-59. doi: 10.1093/hmg/ddq378. Epub Sep. 21, 2010.
Lakowski et al., Effective transplantation of photoreceptor precursor cells selected via cell surface antigen expression. Stem Cells. Sep. 2011;29(9):1391-404. doi: 10.1002/stem.694.
Lambda et al., Efficient generation of retinal progenitor cells from human embryonic stem cells. Proc Natl Acad Sci U S A. Aug. 22, 2006;103(34):12769-74. Epub Aug. 14, 2006.
Lambda et al., Generation, purification and transplantation of photoreceptors derived from human induced pluripotent stem cells. PLoS One. Jan. 20, 2010;5(1):e8763.
Lambda et al., Transplantation of Human Embryonic Stem Cell-Derived Photoreceptors Restores Some Visual Function in Crx-Deficient Mice. Cell Stem Cell. 2009;4:73-9. doi: 10.1016/j.stem.2008.10.015.
Latorre et al., Conserved microRNA pathway regulates developmental timing of retinal neurogenesis. Proc Natl Acad Sci U S A. Jun. 25, 2013;110(26):E2362-70. doi: 10.1073/pnas.1301837110. Epub Jun. 10, 2013.
Li et al., Rapid induction and long-term self-renewal of primitive neural precursors from human embryonic stem cells by small molecule inhibitors. Proc Natl Acad Sci U S A. May 17, 2011;108(20):8299-304. doi: 10.1073/pnas.1014041108. Epub Apr. 27, 2011.
Liu et al., Integrated analysis of DNA methylation and RNA transcriptome during in vitro differentiation of human pluripotent stem cells into retinal pigment epithelial cells. PLoS One. Mar. 17, 2014;9(3):e91416. doi:10.1371/journal.pone.0091416. eCollection 2014. e91416.

Livne-Bar et al., Chx10 is required to block photoreceptor differentiation but is dispensable for progenitor proliferation in the postnatal retina. Proc Natl Acad Sci U S A. Mar. 28, 2006;103(13):4988-93.
Lolley et al., Linkage of photoreceptor degeneration by apoptosis with inherited defect in phototransduction. Invest Ophthalmol Vis Sci. Feb. 1994;35(2):358-62.
Lund et al., Human embryonic stem cell-derived cells rescue visual function in dystrophic RCS rats. Cloning Stem Cells. 2006 Fall;8(3):189-99.
Luo et al., Human retinal progenitor cell transplantation preserves vision. J Biol Chem. Mar. 7, 2014;289(10):6362-71. doi: 10.1074/jbc.M113.513713. Epub Jan. 9, 2014.
MacLaren et al., Retinal repair by transplantation of photoreceptor precursors. Nature. Nov. 9, 2006;444:203-7. Abstract Only.
McUsic et al., Guiding the morphogenesis of dissociated newborn mouse retinal cells and hES cell-derived retinal cells by soft lithography-patterned microchannel PLGA scaffolds. Biomaterials. Feb. 2012;33(5):1396-405. doi: 10.1016/j.biomaterials.2011.10.083. Epub Nov. 23, 2011.
Mellough et al., Efficient stage-specific differentiation of human pluripotent stem cells toward retinal photoreceptor cells. Stem Cells. Apr. 2012;30(4):673-86.
Meyer et al., Embryonic stem cell-derived neural progenitors incorporate into degenerating retina and enhance survival of host photoreceptors. Stem Cells. Feb. 2006;24(2):274-83. Epub Aug. 25, 2005.
Meyer et al., Modeling early retinal development with human embryonic and induced pluripotent stem cells. Proc Natl Acad Sci U S A. Sep. 29, 2009;106(39):16698-703. doi: 10.1073/pnas.0905245106. Epub Aug. 25, 2009.
Meyer et al., Optic vesicle-like structures derived from human pluripotent stem cells facilitate a customized approach to retinal disease treatment. Stem Cells. Aug. 2011;29(8):1206-18. doi: 10.1002/stem.674.
Nagy et al., Murine embryonic stem cells. Methods Enzymol. 2006;418:3-21. Abstract only.
Nakagawa et al., Generation of induced pluripotent stem cells without Myc from mouse and human fibroblasts. Nat Biotechnol. Jan. 2008;26(1):101-6. Epub Nov. 30, 2007. Abstract only.
Nishida et al., Corneal reconstruction with tissue-engineered cell sheets composed of autologous oral mucosal epithelium. N Engl J Med. Sep. 16, 2004;351(12):1187-96.
Nishida et al., Functional bioengineered corneal epithelial sheet grafts from corneal stem cells expanded ex vivo on a temperature-responsive cell culture surface. Transplantation. Feb. 15, 2004;77(3):379-85. Abstract Only.
Osakada et al., In vitro differentiation of retinal cells from human pluripotent stem cells by small-molecule induction. J Cell Sci. Sep. 1, 2009;122(Pt 17):3169-79. doi: 10.1242/jcs.050393. Epub Aug. 11, 2009.
Osakada et al., Toward the generation of rod and cone photoreceptors from mouse, monkey and human embryonic stem cells. Nat Biotechnol. Feb. 2008;26(2):215-24. doi: 10.1038/nbt1384. Epub Feb. 3, 2008. Erratum in: Nat Biotechnol. Mar. 2008;26(3):352. Abstract only.
Patterson et al., Defining the nature of human pluripotent stem cell progeny. Cell Res. Jan. 2012;22(1):178-93. doi: 10.1038/cr.2011.133. Epub Aug. 16, 2011.
Pearson et al., Restoration of vision after transplantation of photoreceptors. Nature. May 3, 2012;485(7396):99-103. doi: 10.1038/nature10997.
Punzo et al., Cellular responses to photoreceptor death in the rd1 mouse model of retinal degeneration. Invest Ophthalmol Vis Sci. Feb. 2007;48(2):849-57.
Reynolds et al., Generation of neurons and astrocytes from isolated cells of the adult mammalian central nervous system. Science. Mar. 27, 1992;255(5052):1707-10.
Schwartz et al., Embryonic stem cell trials for macular degeneration: a preliminary report. Lancet. Feb. 25, 2012;379(9817):713-20. doi:10.1016/S0140-6736(12)60028-2. Epub Jan. 24, 2012. Abstract only.
Schwartz et al., Human embryonic stem cell-derived retinal pigment epithelium in patients with age-related macular degeneration and

(56) References Cited

OTHER PUBLICATIONS

Stargardt's macular dystrophy: follow-up of two open-label phase 1/2 studies. Lancet. Feb. 7, 2015;385(9967):509-16. doi: 10.1016/S0140-6736(14)61376-3. Epub Oct. 15, 2014. Abstract only.
Singh et al., Reversal of end-stage retinal degeneration and restoration of visual function by photoreceptor transplantation. Proc Natl Acad Sci U S A. Jan. 15, 2013;110(3):1101-6. doi: 10.1073/pnas.1119416110. Epub Jan. 3, 2013.
Stingl et al., Artificial vision with wirelessly powered subretinal electronic implant alpha-IMS. Proc Biol Sci. Feb. 20, 2013;280(1757):20130077. doi: 10.1098/rspb.2013.0077. Print Apr. 22, 2013.
Sullivan et al., Introduction. Chapter 4: Derivation of human embryonic stem cell lines. In Human Embryonic Stem Cells: The Practical Handbook. Eds. Stephen Sullivan et al. John Wiley & Sons. Nov. 2007:p. 35.
Sumide et al., Functional human corneal endothelial cell sheets harvested from temperature-responsive culture surfaces. FASEB J. Feb. 2006;20(2):392-4. Epub Dec. 9, 2005. 23 Pages.
Swaroop et al., Transcriptional regulation of photoreceptor development and homeostasis in the mammalian retina. Nat Rev Neurosci. Aug. 2010;11(8):563-76.
Tucker et al., Patient-specific iPSC-derived photoreceptor precursor cells as a means to investigate retinitis pigmentosa. Elife. Aug. 27, 2013;2:e00824. doi: 10.7554/eLife.00824.
Tucker et al., Transplantation of adult mouse iPS cell-derived photoreceptor precursors restores retinal structure and function in degenerative mice. PLoS One. Apr. 29, 2011;6(4):e18992. doi: 10.1371/journal.pone.0018992. Erratum in: PLoS One. 2015;10(5):e0125947.
Vunjak-Novakovic et al., Biomimetic platforms for human stem cell research. Cell Stem Cell. Mar. 4, 2011;8(3):252-61. doi:10.1016/j.stem.2011.02.014.
West et al., Defining the integration capacity of embryonic stem cell-derived photoreceptor precursors. Stem Cells. Jul. 2012;30(7):1424-35. doi: 10.1002/stem.1123.
West et al., Long-term survival of photoreceptors transplanted into the adult murine neural retina requires immune modulation. Stem Cells. Nov. 2010;28(11):1997-2007. doi: 10.1002/stem.520.
Xiao et al., Spatial and temporal expression of short, long/medium, or both opsins in human fetal cones. J Comp Neurol. Oct. 2, 2000;425(4):545-59. Abstract only.
Yao et al., XIAP therapy increases survival of transplanted rod precursors in a degenerating host retina. Invest Ophthalmol Vis Sci. Mar. 1, 2011;52(3):1567-72. doi: 10.1167/iovs.10-5998. Print Mar. 2011.
Yi et al., A fibronectin fragment inhibits tumor growth, angiogenesis, and metastasis. Proc Natl Acad Sci U S A. Jan. 16, 2001;98(2):620-4.
Zaghloul et al., Changes in Rx1 and Pax6 activity at eye field stages differentially alter the production of amacrine neurotransmitter subtypes in *Xenopus*. Mol Vis. 2007;13:86-95. Epub Jan. 26, 2007.
Zrenner et al., Subretinal electronic chips allow blind patients to read letters and combine them to words. Proc Biol Sci. May 22, 2011;278(1711):1489-97. doi: 10.1098/rspb.2010.1747. Epub Nov. 3, 2010.
Zwaka et al., A germ cell origin of embryonic stem cells? Development. Jan. 2005;132(2):227-33.
Katoh et al., Blimp1 suppresses Chx10 expression in differentiating retinal photoreceptor precursors to ensure proper photoreceptor development. J Neurosci. 2010;30(19):6515-6526. doi:10.1523/JNEUROSCI.0771-10.2010.
Assawachananont et al., Transplantation of embryonic and induced pluripotent stem cell-derived 3D retinal sheets into retinal degenerative mice. Stem Cell Reports. Apr. 24, 2014;2(5):662-74. doi: 10.1016/j.stemcr.2014.03.011.
Canto-Soler et al., Stem Cell Sources and Their Potential for the Treatment of Retinal Degenerations. Invest Ophthalmol Vis Sci. Apr. 1, 2016;57(5):ORSFd1-9. doi: 10.1167/iovs.16-19127.

Capowski et al., Reproducibility and staging of 3D human retinal organoids across multiple pluripotent stem cell lines. Development. Jan. 9, 2019;146(1):dev171686(1-29). doi: 10.1242/dev.171686.
Chao et al., Transplantation of Human Embryonic Stem Cell-Derived Retinal Cells into the Subretinal Space of a Non-Human Primate. Transl Vis Sci Technol. May 16, 2017;6(3):4(1-13). doi: 10.1167/tvst.6.3.4.
Collin et al., Deconstructing Retinal Organoids: Single Cell RNA-Seq Reveals the Cellular Components of Human Pluripotent Stem Cell-Derived Retina. Stem Cells. May 2019;37(5):593-598. doi: 10.1002/stem.2963. Epub Jan. 12, 2019.
Collin et al., Using Zinc Finger Nuclease Technology to Generate CRX-Reporter Human Embryonic Stem Cells as a Tool to Identify and Study the Emergence of Photoreceptors Precursors During Pluripotent Stem Cell Differentiation. Stem Cells. Feb. 2016;34(2):311-21. doi: 10.1002/stem.2240. Epub Nov. 26, 2015.
Dorgau et al., Laminin γ3 plays an important role in retinal lamination, photoreceptor organisation and ganglion cell differentiation. Cell Death Dis. May 23, 2018;9(6):615(1-13). doi: 10.1038/s41419-018-0648-0.
Eldred et al., Thyroid hormone signaling specifies cone subtypes in human retinal organoids. Science. Oct. 12, 2018;362(6411):eaau6348(1-8). Supplemental Information Included, 20 pages, doi: 10.1126/science.aau6348.
Felemban et al., Extracellular matrix component expression in human pluripotent stem cell-derived retinal organoids recapitulates retinogenesis in vivo and reveals an important role for IMPG1 and CD44 in the development of photoreceptors and interphotoreceptor matrix. Acta Biomater. Jul. 1, 2018;74:207-221. doi: 10.1016/j.actbio.2018.05.023. Epub May 17, 2018.
Gagliardi et al., Characterization and Transplantation of CD73-Positive Photoreceptors Isolated from Human iPSC-Derived Retinal Organoids. Stem Cell Reports. Sep. 11, 2018;11(3):665-680. doi: 10.1016/j.stemcr.2018.07.005. Epub Aug. 9, 2018.
Gagliardi et al., Photoreceptor cell replacement in macular degeneration and retinitis pigmentosa: A pluripotent stem cell-based approach. Prog Retin Eye Res. Jul. 2019;71:1-25. doi: 10.1016/j.preteyeres.2019.03.001. Epub Mar. 16, 2019.
Gonzalez-Cordero et al., Recapitulation of Human Retinal Development from Human Pluripotent Stem Cells Generates Transplantable Populations of Cone Photoreceptors. Stem Cell Reports. Sep. 12, 2017;9(3):820-837. doi: 10.1016/j.stemcr.2017.07.022. Epub Aug. 24, 2017.
Hallam et al., Human-Induced Pluripotent Stem Cells Generate Light Responsive Retinal Organoids with Variable and Nutrient-Dependent Efficiency. Stem Cells. Oct. 2018;36(10):1535-1551. doi: 10.1002/stem.2883. Epub Aug. 13, 2018.
Hunt et al., 3D culture of human pluripotent stem cells in RGD-alginate hydrogel improves retinal tissue development. Acta Biomater. Feb. 2017;49:329-343. doi: 10.1016/j.actbio.2016.11.016. Epub Nov. 5, 2016.
Iraha et al., Establishment of Immunodeficient Retinal Degeneration Model Mice and Functional Maturation of Human ESC-Derived Retinal Sheets after Transplantation. Stem Cell Reports. Mar. 13, 2018;10(3): 1059-1074. doi: 10.1016/j.stemcr.2018.01.032. Epub Mar. 1, 2018.
Jin et al., Modeling retinal degeneration using patient-specific induced pluripotent stem cells. PLoS One. Feb. 10, 2011;6(2):e17084(1-8). doi: 10.1371/journal.pone.0017084.
Jung et al., 3D Microstructured Scaffolds to Support Photoreceptor Polarization and Maturation. Adv Mater. Sep. 2018;30(39):e1803550(1-10). Supplemental Information Included, 10 pages. doi: 10.1002/adma.201803550. Epub Aug. 14, 2018.
Kallman et al., Investigating cone photoreceptor development using patient-derived NRL null retinal organoids. Commun Biol. Feb. 21, 2020 ;3(1):82(1-13). doi: 10.1038/s42003-020-0808-5.
Kelley et al., Retinoic acid promotes differentiation of photoreceptors in vitro. Development. Aug. 1994;120(8):2091-102.
Kuwahara et al., Generation of a ciliary margin-like stem cell niche from self-organizing human retinal tissue. Nat Commun. Feb. 19, 2015;6:6286(1 -15). doi: 10.1038/ncomms7286.

(56) References Cited

OTHER PUBLICATIONS

Levine et al., Sonic hedgehog promotes rod photoreceptor differentiation in mammalian retinal cells in vitro. J Neurosci. Aug. 15, 1997;17(16):6277-88. doi: 10.1523/JNEUROSCI. 17-16-06277.1997.

Li et al., Generation of Retinal Organoids with Mature Rods and Cones from Urine-Derived Human Induced Pluripotent Stem Cells. Stem Cells Int. Jun. 13, 2018;2018:4968658(1-13). doi: 10.1155/2018/4968658.

Mandai et al., iPSC-Derived Retina Transplants Improve Vision in rd1 End-Stage Retinal-Degeneration Mice. Stem Cell Reports. Jan. 10, 2017;8(1):69-83. doi: 10.1016/j.stemcr.2016.12.008. Erratum in: Stem Cell Reports. Feb. 14, 2017;8(2):489. Erratum in: Stem Cell Reports. Apr. 11, 2017;8(4):1112-1113.

Mellough et al., Signaling Plays an Important Role in the Formation of Three-Dimensional Laminated Neural Retina and Other Ocular Structures From Human Embryonic Stem Cells. Stem Cells. Aug. 2015;33(8):2416-30. doi: 10.1002/stem.2023. Epub May 13, 2015.

Mellough et al., Systematic Comparison of Retinal Organoid Differentiation from Human Pluripotent Stem Cells Reveals Stage Specific, Cell Line, and Methodological Differences. Stem Cells Transl Med. Jul. 2019;8(7):694-706. doi: 10.1002/sctm.18-0267. Epub Mar. 27, 2019.

Nakano et al., Self-formation of optic cups and storable stratified neural retina from human ESCs. Cell Stem Cell. Jun. 14, 2012;10(6):771-785. doi: 10.1016/j.stem.2012.05.009.

Osakada et al., Stepwise differentiation of pluripotent stem cells into retinal cells. Nat Protoc. 2009;4(6):811-24. doi: 10.1038/nprot.2009.51. Epub May 7, 2009.

Ovando-Roche et al., Use of bioreactors for culturing human retinal organoids improves photoreceptor yields. Stem Cell Res Ther. Jun. 13, 2018;9(1):156(1-14). Supplemental Information Included, 6 pages, doi: 10.1186/s13287-018-0907-0.

Phillips et al., A Novel Approach to Single Cell RNA-Sequence Analysis Facilitates In Silico Gene Reporting of Human Pluripotent Stem Cell-Derived Retinal Cell Types. Stem Cells. Mar. 2018;36(3):313-324. doi: 10.1002/stem.2755. Epub Dec. 25, 2017. Erratum in: Stem Cells. Jul. 2018;36(7):1133.

Phillips et al., Generation of a rod-specific NRL reporter line in human pluripotent stem cells. Sci Rep. Feb. 5, 2018;8(1):2370. Supplemental Information Included, 26 pages, doi: 10.1038/s41598-018-20813-3.

Phillips et al., Modeling human retinal development with patient-specific induced pluripotent stem cells reveals multiple roles for visual system homeobox 2. Stem Cells. Jun. 2014;32(6): 1480-92. doi: 10.1002/stem. 1667.

Reh, Photoreceptor Transplantation in Late Stage Retinal Degeneration. Invest Ophthalmol Vis Sci. Apr. 1, 2016;57(5):ORSFgl-7. doi: 10.1167/iovs.15-17659.

Reichman et al., From confluent human iPS cells to self-forming neural retina and retinal pigmented epithelium. Proc Natl Acad Sci USA. Jun. 10, 2014; 111(23):8518-23. doi: 10.1073/pnas.1324212111. Epub May 27, 2014.

Reichman et al., Generation of Storable Retinal Organoids and Retinal Pigmented Epithelium from Adherent Human iPS Cells in Xeno-Free and Feeder-Free Conditions. Stem Cells. May 2017;35(5):1176-1188. doi: 10.1002/stem.2586. Epub Feb. 20, 2017.

Seiler et al., A new immunodeficient pigmented retinal degenerate rat strain to study transplantation of human cells without immunosuppression. Graefes Arch Clin Exp Ophthalmol. Jul. 2014;252(7): 1079-92. doi: 10.1007/s00417-014-2638-y. Epub May 13, 2014.

Shirai et al., Transplantation of human embryonic stem cell-derived retinal tissue in two primate models of retinal degeneration. Proc Natl Acad Sci USA. Jan. 5, 2016; 113(1):E81-90. Supplemental Information Included, 8 pages, doi: 10.1073/pnas.1512590113. Epub Dec. 22, 2015.

Singh et al., Characterization of Three-Dimensional Retinal Tissue Derived from Human Embryonic Stem Cells in Adherent Monolayer Cultures. Stem Cells Dev. Dec. 1, 2015;24(23):2778-95. doi: 10.1089/scd.2015.0144. Epub Sep. 10, 2015.

Suzuki et al., The simultaneous treatment of MMP-2 stimulants in retinal transplantation enhances grafted cell migration into the host retina. Stem Cells. Nov. 2006;24(ll):2406-11. doi: 10.1634/stemcells.2005-0587.

Tu et al., Medium- to long-term survival and functional examination of human iPSC-derived retinas in rat and primate models of retinal degeneration. EBioMedicine. Jan. 2019;39:562-574. doi: 10.1016/j.ebiom.2018.11.028. Epub Nov. 28, 2018.

Vergara et al., Three-dimensional automated reporter quantification (3D-ARQ) technology enables quantitative screening in retinal organoids. Development. Oct. 15, 2017;144(20):3698-3705. doi: 10.1242/dev. 146290. Epub Sep. 4, 2017.

Volkner et al., Retinal Organoids from Pluripotent Stem Cells Efficiently Recapitulate Retinogenesis. Stem Cell Reports. Apr. 12, 2016;6(4):525-538. doi: 10.1016/j.stemcr.2016.03.001. Epub Mar. 31, 2016.

Wahlin et al., Photoreceptor Outer Segment-like Structures in Long-Term 3D Retinas from Human Pluripotent Stem Cells. Sci Rep. Apr. 10, 2017;7(1):766(1-15). doi: 10.1038/s41598-017-00774-9.

West et al., Development of Stem Cell Therapies for Retinal Degeneration. Cold Spring Harb Perspect Biol. Aug. 3, 2020;12(8):a035683(l-24). doi: 10.1101/cshperspect.a035683.

Yanai et al., Differentiation of human embryonic stem cells using size-controlled embryoid bodies and negative cell selection in the production of photoreceptor precursor cells. Tissue Eng Part C Methods. Oct. 2013;19(10):755-64. doi: 10.1089/ten.TEC.2012.0524. Epub Mar. 15, 2013.

Zhong et al., Generation of three-dimensional retinal tissue with functional photoreceptors from human iPSCs. Nat Commun. Jun. 10, 2014;5:4047(1-14). Supplemental Information Included, 6 pages, doi: 10.1038/ncomms5047.

Zhou et al., Differentiation of human embryonic stem cells into cone photoreceptors through simultaneous inhibition of BMP, TGFβ and Wnt signaling. Development. Oct. 1, 2015;142(19):3294-306. Supplemental Information Included, 12 pages, doi: 10.1242/dev.125385.

Zhu et al., Three-dimensional neuroepithelial culture from human embryonic stem cells and its use for quantitative conversion to retinal pigment epithelium. PLoS One. 2013;8(1):e54552(1-13). doi: 10.1371/journal.pone.0054552. Epub Jan. 24, 2013.

Brzezinski et al., Ascl1 expression defines a subpopulation of lineage-restricted progenitors in the mammalian retina. Development. Aug. 2011;138(16):3519-31. doi: 10.1242/dev.064006. Epub Jul. 19, 2011.

Freund et al., Cone-rod dystrophy due to mutations in a novel photoreceptor-specific homeobox gene (CRX) essential for maintenance of the photoreceptor. Cell. Nov. 14, 1997;91(4):543-53. doi: 10.1016/s0092-8674(00)80440-7.

Merhi-Soussi et al., High yield of cells committed to the photoreceptor fate from expanded mouse retinal stem cells. Stem Cells. Sep. 2006;24(9):2060-70. doi: 10.1634/stemcells.2005-0311. Epub Apr. 27, 2006.

Parameswaran et al., Induced pluripotent stem cells generate both retinal ganglion cells and photoreceptors: therapeutic implications in degenerative changes in glaucoma and age-related macular degeneration. Stem Cells. Apr. 2010;28(4):695-703. doi: 10.1002/stem.320.

Tomita et al., Mash1 promotes neuronal differentiation in the retina. Genes Cells. Aug. 1996;1(8):765-74. doi: 10.1111/j.1365-2443.1996.tb00016.x.

* cited by examiner

PAX6

CHX10

MERGE

Pax6/CHX10/DAPI

Recoverin/DAPI

Rhodopsin/DAPI

Rhodopsin/Recoverin/DAPI

Opsin (green/red)/DAPI

PDE6a/DAPI

| DMEM/F12 Components | Molecular Weight | Concentration (mg/L) | mM |
|---|---|---|---|
| Amino Acids | | | |
| Glycine | 75 | 18.75 | 0.25 |
| L-Alanine | 89 | 4.45 | 0.05 |
| L-Arginine hydrochloride | 211 | 147.5 | 0.699 |
| L-Asparagine-H2O | 150 | 7.5 | 0.05 |
| L-Aspartic acid | 133 | 6.65 | 0.05 |
| L-Cysteine hydrochloride-H2O | 176 | 17.56 | 0.0998 |
| L-Cystine 2HCl | 313 | 31.29 | 0.1 |
| L-Glutamic Acid | 147 | 7.35 | 0.05 |
| L-Glutamine | 146 | 365 | 2.5 |
| L-Histidine hydrochloride-H2O | 210 | 31.48 | 0.15 |
| L-Isoleucine | 131 | 54.47 | 0.416 |
| L-Leucine | 131 | 59.05 | 0.451 |
| L-Lysine hydrochloride | 183 | 91.25 | 0.499 |

FIG. 21A

| | | | |
|---|---|---|---|
| L-Methionine | 149 | 17.24 | 0.116 |
| L-Phenylalanine | 165 | 35.48 | 0.215 |
| L-Proline | 115 | 17.25 | 0.15 |
| L-Serine | 105 | 26.25 | 0.25 |
| L-Threonine | 119 | 53.45 | 0.449 |
| L-Tryptophan | 204 | 9.02 | 0.0442 |
| L-Tyrosine disodium salt dihydrate | 261 | 55.79 | 0.214 |
| L-Valine | 117 | 52.85 | 0.452 |
| Vitamins | | | |
| Biotin | 244 | 0.0035 | 1.43E-05 |
| Choline chloride | 140 | 8.98 | 0.0641 |
| D-Calcium pantothenate | 477 | 2.24 | 0.0047 |
| Folic Acid | 441 | 2.65 | 0.00601 |
| Niacinamide | 122 | 2.02 | 0.0166 |
| Pyridoxine hydrochloride | 206 | 2 | 0.00971 |
| Riboflavin | 376 | 0.219 | 0.000582 |
| Thiamine hydrochloride | 337 | 2.17 | 0.00644 |
| Vitamin B12 | 1355 | 0.68 | 0.000502 |
| i-Inositol | 180 | 12.6 | 0.07 |
| Inorganic Salts | | | |
| Calcium Chloride (CaCl2) (anhyd.) | 111 | 116.6 | 1.05 |
| Cupric sulfate (CuSO4-5H2O) | 250 | 0.0013 | 5.2E-06 |
| Ferric Nitrate (Fe(NO3)3-9H2O) | 404 | 0.05 | 0.000124 |
| Ferric sulfate (FeSO4-7H2O) | 278 | 0.417 | 0.0015 |
| Magnesium Chloride (anhydrous) | 95 | 28.64 | 0.301 |
| Magnesium Sulfate (MgSO4) (anhyd.) | 120 | 48.84 | 0.407 |
| Potassium Chloride (KCl) | 75 | 311.8 | 4.16 |

FIG. 21B

| | | | |
|---|---|---|---|
| Sodium Bicarbonate (NaHCO3) | 84 | 1200 | 14.29 |
| Sodium Chloride (NaCl) | 58 | 6995.5 | 120.61 |
| Sodium Phosphate dibasic (Na2HPO4) anhydrous | 142 | 71.02 | 0.5 |
| Sodium Phosphate monobasic (NaH2PO4-H2O) | 138 | 62.5 | 0.453 |
| Zinc sulfate (ZnSO4-7H2O) | 288 | 0.432 | 0.0015 |
| Other Components | | | |
| D-Glucose (Dextrose) | 180 | 3151 | 17.51 |
| HEPES | 238 | 3574.5 | 15.02 |
| Hypoxanthine Na | 159 | 2.39 | 0.015 |
| Linoleic Acid | 280 | 0.042 | 0.00015 |
| Lipoic Acid | 206 | 0.105 | 0.00051 |
| Phenol Red | 376.4 | 8.1 | 0.0215 |
| Putrescine 2HCl | 161 | 0.081 | 0.000503 |
| Sodium Pyruvate | 110 | 55 | 0.5 |
| Thymidine | 242 | 0.365 | 0.00151 |

| Neurobasal Components | Molecular Weight | Concentration (mg/L) | mM |
|---|---|---|---|
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-H2O | 150 | 0.83 | 0.00553 |
| L-Cysteine | 121 | 31.5 | 0.26 |
| L-Histidine hydrochloride-H2O | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |

FIG. 21C

| | | | |
|---|---|---|---|
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3-9H2O) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate (NaHCO3) | 84 | 2200 | 26.19 |
| Sodium Chloride (NaCl) | 58 | 3000 | 51.72 |
| Sodium Phosphate monobasic (NaH2PO4-H2O) | 138 | 125 | 0.906 |
| Zinc sulfate (ZnSO4-7H2O) | 288 | 0.194 | 0.000674 |
| Other Components | | | |
| D-Glucose (Dextrose) | 180 | 4500 | 25 |
| HEPES | 238 | 2600 | 10.92 |
| Phenol Red | 376.4 | 8.1 | 0.0215 |
| Sodium Pyruvate | 110 | 25 | 0.227 |

| N2 Supplement Components | Molecular Weight | Concentration (mg/L) | mM |
|---|---|---|---|
| Proteins | | | |
| Human Transferrin (Holo) | 10000 | 10000 | 1 |
| Insulin Recombinant Full Chain | 5807.7 | 500 | 0.0861 |
| Other Components | | | |
| Progesterone | 314.47 | 0.63 | 0.002 |
| Putrescine | 161 | 1611 | 10.01 |
| Selenite | 173 | 0.52 | 0.00301 |

FIG. 21D

B27 Components

| Vitamins |
|---|

Biotin

DL Alpha Tocopherol Acetate
DL Alpha-Tocopherol
Vitamin A (acetate)

| Proteins |
|---|

BSA, fatty acid free Fraction V
Catalase

Human Recombinant Insulin
Human Transferrin
Superoxide Dismutase

| Other Components |
|---|

Corticosterone
D-Galactose
Ethanolamine HCl
Glutathione (reduced)
L-Carnitine HCl
Linoleic Acid
Linolenic Acid
Progesterone
Putrescine 2HCl
Sodium Selenite
T3 (triodo-l-thyronine)

FIG. 21E

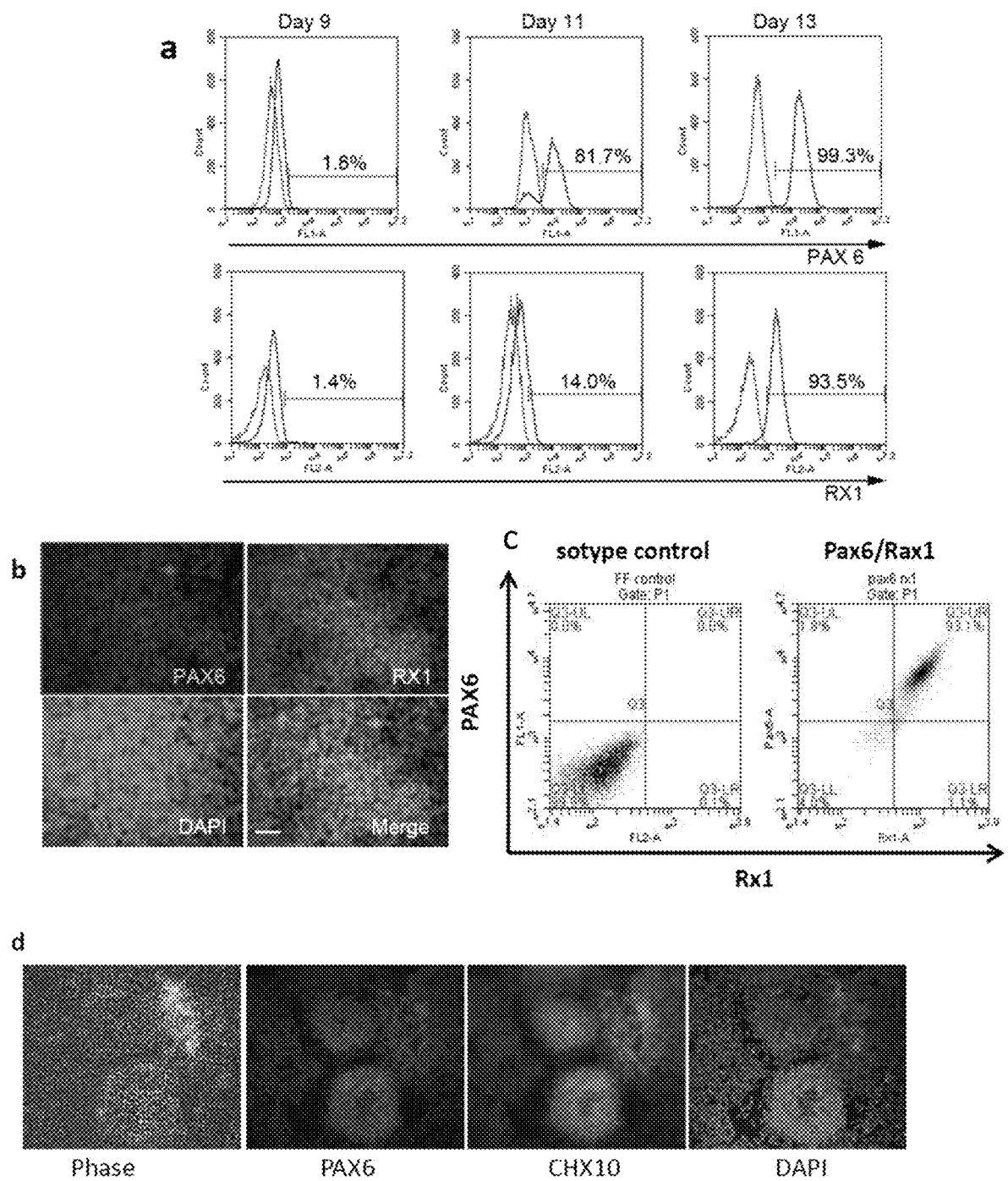
FIGs. 32A-D

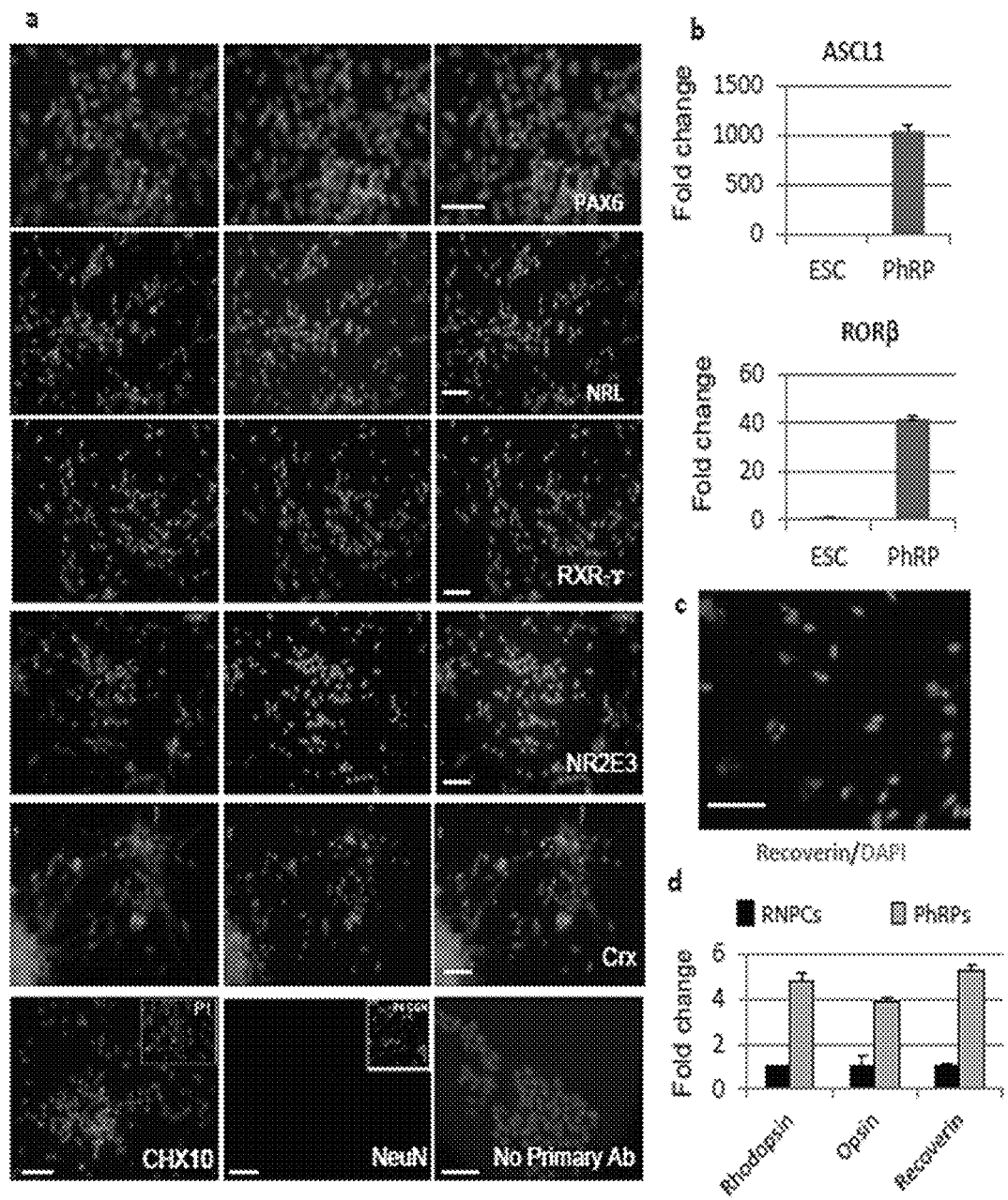
FIGs. 33A-D

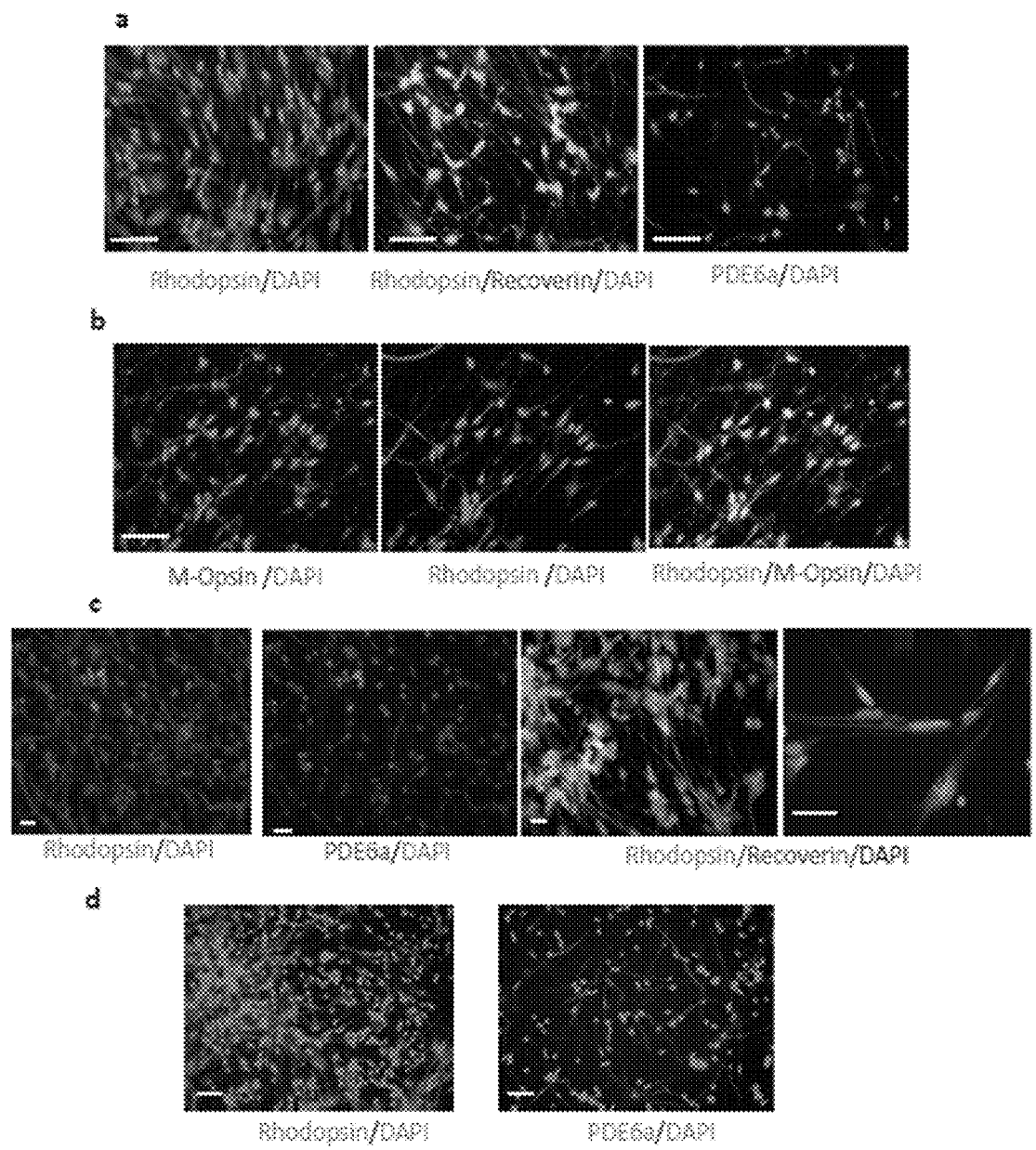
FIGs. 34A-D

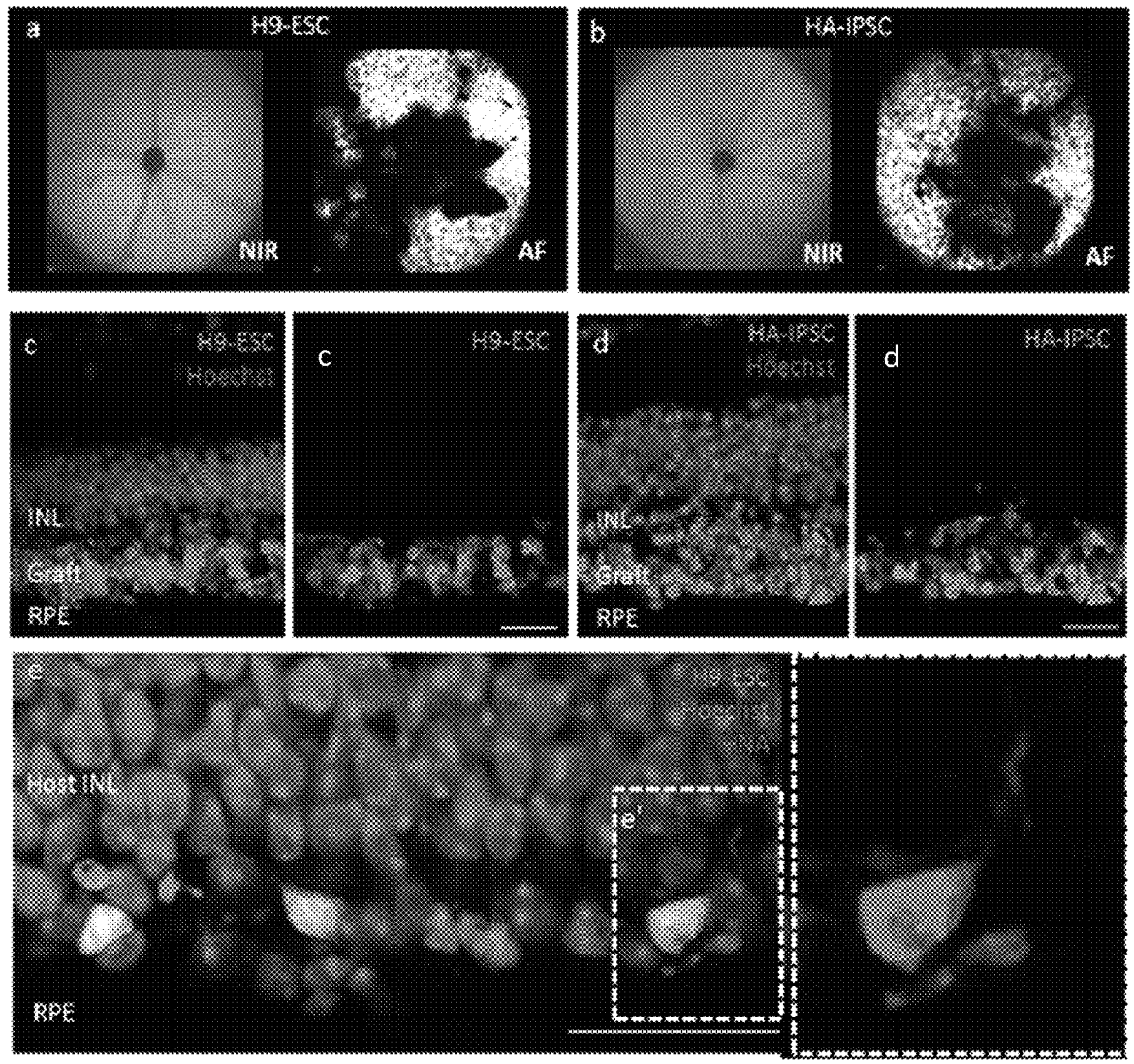
FIGs. 35A-E

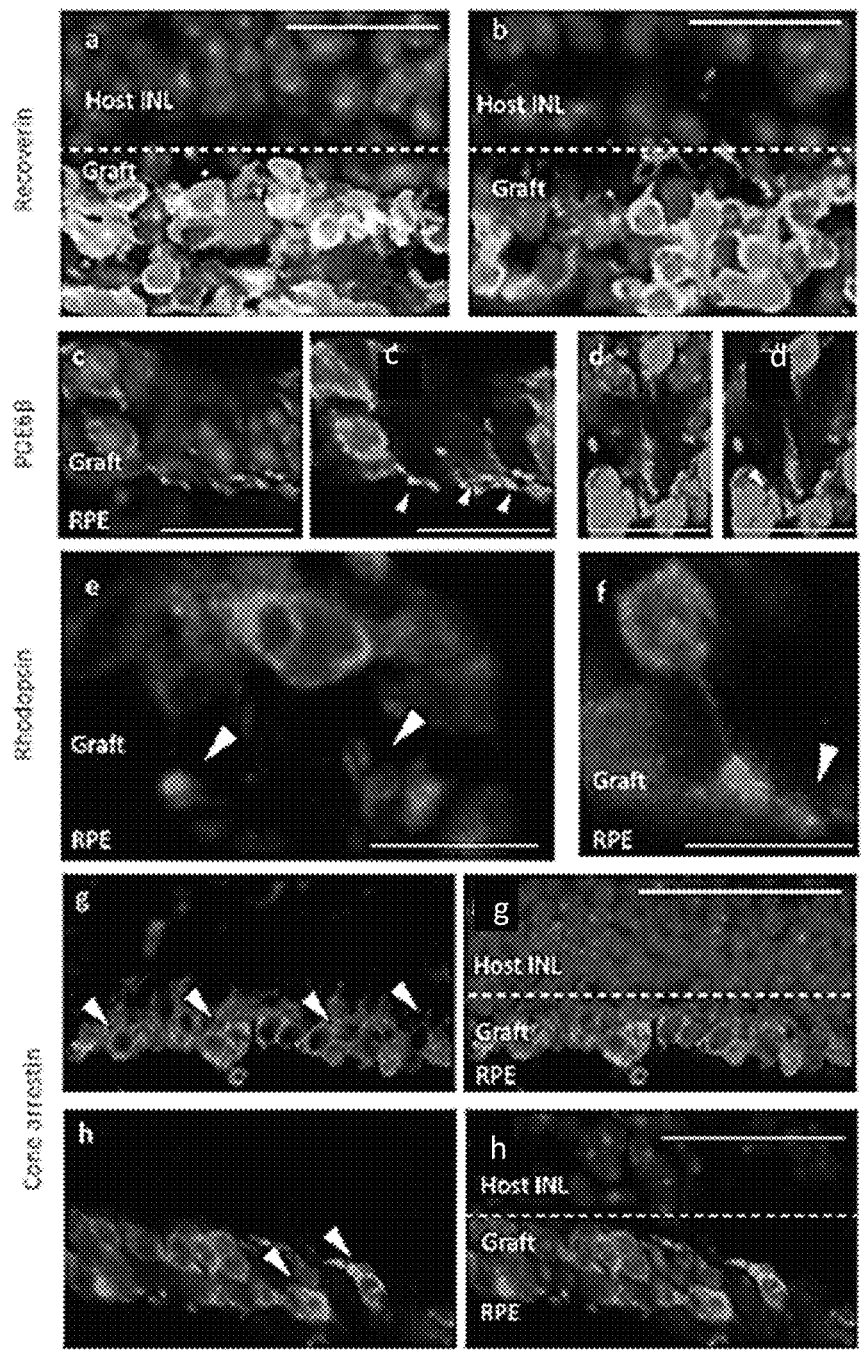
FIGs. 36A-H

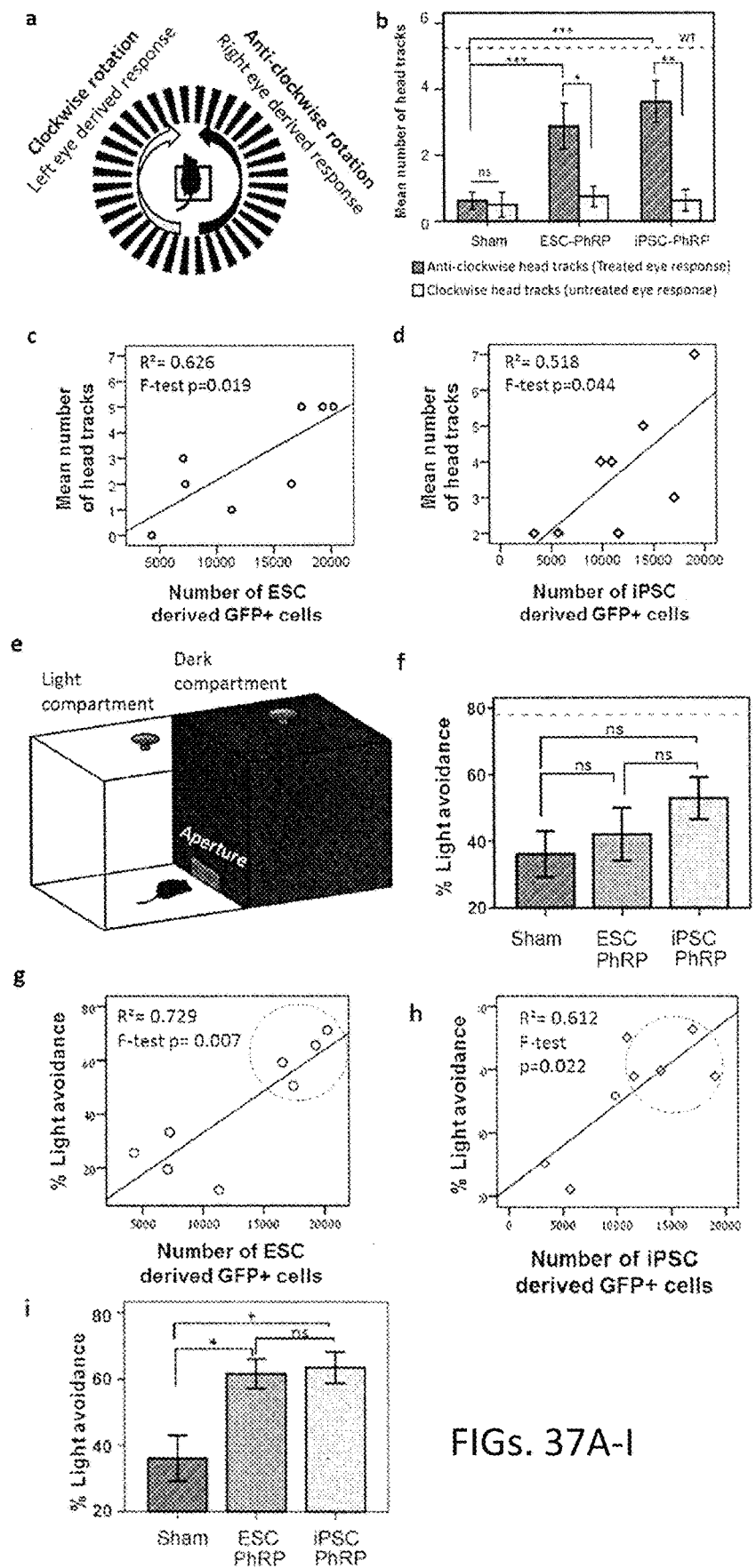
FIGs. 37A-I

PHOTORECEPTORS AND PHOTORECEPTOR PROGENITORS PRODUCED FROM PLURIPOTENT STEM CELLS

RELATED APPLICATIONS

This application is a continuation of U.S. Non-provisional application Ser. No. 14/857,780, filed Sep. 17, 2015, which is a continuation-in-part of U.S. Non-provisional application Ser. No. 14/489,415, filed Sep. 17, 2014, which is a continuation-in-part of U.S. Non-provisional application Ser. No. 14/214,598 and of International Application Serial No. PCT/US2014/029790, both filed Mar. 14, 2014, which claim the benefit under 35 U.S.C. § 119(e) of U.S. Provisional Application Ser. No. 61/793,168, filed Mar. 15, 2013, all entitled "PHOTORECEPTORS AND PHOTORECEPTOR PROGENITORS PRODUCED FROM PLURIPOTENT STEM CELLS", the entire contents of all of which are incorporated herein by reference.

BACKGROUND

Retinal diseases often result in blindness due to loss of post-mitotic neuronal cells. Among the retinal diseases are rod or cone dystrophies, retinal degeneration, retinitis pigmentosa, diabetic retinopathy, macular degeneration, Leber congenital amaurosis and Stargardt disease. In most retinal degenerations, cell loss is primarily in the outer nuclear layer which includes rod and cone photoreceptors. With the loss of post-mitotic neuronal cell populations, an exogenous source of new cells as a replacement for photoreceptor cells is needed.

A potential replacement source of photoreceptor cells includes stem cells. Early studies incorporated the use of mouse cells, mouse stem cells or heterogeneous populations of retinal progenitor cells as a possible source of cells for replacement of lost photoreceptors. These early studies described transplantation of photoreceptor precursor cells from postnatal day 1 mouse retina (Maclaren et al. Nature 444(9):203-207, 2006), in vitro generation of retinal precursor cells from mouse embryonic stem cells (Ikeda et al. Proc. Natl. Acad. Sci. 102(32):11331-11336, 2005), generation of retinal progenitor cells from postnatal day 1 mouse retinas (Klassen et al. Invest. Ophthal. Vis. Sci. 45(11):4167-4175, 2004), implantation of bone marrow mesenchymal stem cells in an RCS rat model of retinal degeneration (Inoue et al. Exp. Eye Res. 8(2):234-241, 2007), production of retinal progenitor cells, including ganglion cells, amacrine cells, photoreceptors wherein 0.01% of the total cells expressed S-opsin or rhodopsin, bipolar cells and horizontal cells, from the H1 human embryonic stem cell line (Lamba et al. Proc. Natl. Acad. Sci. 10(34):12769-12774, 2006) and induction of induced pluripotent stem cells (iPS) from human fibroblasts to produce retinal progenitor cells (Lamba et al. PLoS ONE 5(1):e8763. doi:10.1371/journal.pone.0008763). None of these approaches produced a homogeneous population of photoreceptor progenitor cells or photoreceptor cells for implantation. None of these approaches produced a homogeneous population of photoreceptor progenitor cells or photoreceptor cells that showed in vivo rod or cone function (e.g., detectable by conferring improvements in visual acuity). Supplies of donor-derived tissue from which photoreceptors and photoreceptor progenitors may be isolated (such as cadavers, fetal tissue, and live animals) are limited. Stem cells can be propagated and expanded in vitro indefinitely, providing a potentially inexhaustible source of non-donor derived cells for human therapy. Differentiation of stem cells into a homogeneous population of photoreceptor progenitors or photoreceptors may provide an abundant supply of non-donor derived cells for implantation and treatment of retinal diseases.

SUMMARY

In certain embodiments, the invention provides a substantially pure preparation of photoreceptor progenitor cells, comprising: a plurality of photoreceptor progenitor cells, and a medium suitable for maintaining the viability of the photoreceptor progenitor cells.

In certain embodiments, the invention provides a preparation of photoreceptor progenitor cells, comprising a plurality of cells containing at least 50% photoreceptor progenitor cells, and a medium suitable for maintaining the viability of the photoreceptor progenitor cells In certain embodiments, the invention provides a preparation of photoreceptor progenitor cells, comprising: a plurality of photoreceptor progenitor cells substantially free of pluripotent stem cells, retinal ganglion cells, and/or amacrine cells, i.e., include less than 10% or either of those cells, and even more preferably less than less than 5%, 2%, 1%, 0.1% or even less than 0.01% eye field pluripotent stem cells, retinal ganglion cells, and/or amacrine cells; and a medium suitable for maintaining the viability of the photoreceptor progenitor cells.

In certain embodiments, the invention provides a preparation of photoreceptor progenitor cells, comprising: a plurality of photoreceptor progenitor cells substantially free of pluripotent stem cells, retinal ganglion cells, mature photoreceptors, and/or amacrine cells, i.e., include less than 10% or either of those cells, and even more preferably less than less than 5%, 2%, 1%, 0.1% or even less than 0.01% eye field pluripotent stem cells, retinal ganglion cells, mature photoreceptors, and/or amacrine cells; and a medium suitable for maintaining the viability of the photoreceptor progenitor cells.

In certain embodiments, the invention provides a pharmaceutical preparation of photoreceptor progenitor cells that is suitable for use in a mammalian patient, comprising: a plurality of photoreceptor progenitor cells; and a pharmaceutically acceptable carrier for maintaining the viability of the photoreceptor progenitor cells for transplantation into a mammalian patient.

In certain embodiments, the invention provides a cryogenic cell preparation comprising at least 109 photoreceptor progenitor cells, and a cryopreservative system compatible with the photoreceptor progenitor cells and able to maintain the viability of such cells after thawing.

In preferred embodiments of the above preparations, at least 70% of the cells in the preparation are immunocytochemically PAX6+ and CHX10−, and (though optionally) mRNA transcript positive for MASH1 as detected by qPCR, and even more preferably at least 80%, 90%, 95% or 98% of the cells in the preparation are immunocytochemically PAX6+ and CHX10−, and (though optionally) mRNA transcript positive for MASH1 as detected by qPCR.

In certain embodiments, a majority of the photoreceptor progenitor cells are mRNA transcript positive for Nr2e3, Trβ2, RORβ and NRL as detected by qPCR.

In certain embodiments, the photoreceptor progenitor cells express at least 2, 3, 4, 5 or even 10 fold more, relative to retinal neural progenitor cells, of one or more proteins selected from uPA, Tenascin-C, CXCL16, CX3CL1 and Chitinase 3 like-1, as detected by immunoassay of secreted proteins or mRNA transcript levels by qPCR, In certain embodiments, the photoreceptor progenitor cells have replicative capacity to undergo at least 10, 20, 30, 50 or even 100 population doublings in cell culture with less than 25 percent of the cells undergoing cell death, senescing or differentiating into phenotypically non-photoreceptor cells by the 10th, 20th, 30th, 50th or even 100th doubling.

In certain embodiments, the photoreceptor progenitor cells have transferrin protein and or transferrin mRNA levels which are at least 10, 25, 50 or even 75 percent less than for glyceraldehyde 3-phosphate dehydrogenase.

In certain embodiments, the photoreceptor progenitor cells are HLA-genotypically identical, and preferably are genomically identical.

In certain embodiments, the photoreceptor progenitor cells have a mean terminal restriction fragment length (TRF) that is longer than 7 kb, 7.5 kb, 8 kb, 8.5 kb, 9 kb, 9.5 kb, 10 kb, 10.5 kb, 11 kb, 11.5 kb or even 12 kb.

In certain embodiments, the photoreceptor progenitor cells have a statistically significant decreased content and/or enzymatic activity, relative to fetal-derived photoreceptors, of proteins involved in one or more of (i) cell cycle regulation and cellular aging, (ii) cellular energy and/or lipid metabolism, (iii) apoptosis.

In certain embodiments, the photoreceptor progenitor cells have a statistically significant increased content and/or enzymatic activity of proteins involved in cytoskeleton structure and cellular dynamics relating thereto, relative to fetal derived photoreceptors.

In certain embodiments, the photoreceptor progenitor cells are suitable for administration to a human patient.

In certain embodiments, the photoreceptor progenitor cells are suitable for administration to a non-human veterinarian patient.

In preferred embodiments of the above preparations, the photoreceptor progenitor cells are derived from mammalian pluripotent stem cells, especially human pluripotent stem cells, preferably selected from the group consisting of embryonic stem cells and induced pluripotent stem cells.

In certain embodiments, the photoreceptor progenitor cells are differentiated from a common pluripotent stem cell source.

In certain embodiments, the photoreceptor progenitor cells maintain plasticity to differentiate into both rods and cones.

In certain embodiments, the photoreceptor progenitor cells can be transplanted into the subretinal space of ELOVL4-TG2 mice, will migrate to the outer nucleated layer and will improve scotopic and photopic ERG responses in the ELOVL4-TG2 mice.

In certain embodiments, the photoreceptor progenitor cells have phagocytic activity, such as the ability to phagocytose isolated photoreceptor outer segments, pHrodo™ Red E. coli BioParticles or both.

In certain embodiments, the photoreceptor progenitor cells secrete one or more neuroprotective factors.

In certain embodiments, the medium suitable for maintaining the viability of the photoreceptor progenitor cells is selected from the group consisting of a culture medium, a cryopreservative, and a biocompatible injection medium suitable for injection in a human patient.

In certain embodiments, the photoreceptor progenitor cell preparation is pyrogen and mycogen free.

Another aspect of the present invention provides a pharmaceutical preparation of photoreceptors that is suitable for use in a mammalian patient, comprising pluripotent stem cell derived photoreceptor cells, wherein greater than 70%, 80%, 90%, 95% or even 98% of the cells are immunocytochemically PAX6+, CHX10− and are rhodopsin+ and/or opsin+; and a pharmaceutically acceptable carrier for maintaining the viability of the photoreceptor cells for transplantation into a mammalian patient.

Still another aspect of the present invention provides a pharmaceutical preparation comprising: retinal pigment epithelial cells and either photoreceptor progenitor cells, photoreceptor cells or both; and a pharmaceutically acceptable carrier for maintaining the viability of the photoreceptor cells for transplantation into a mammalian patient. The preparation of cells can be provided as cells suspensions (either admixed together, or in the form of a kit with separate doses of cells that be delivered conjointly), or as a multi-layer cell graft (optionally disposed on a biocompatible matrix or solid support). In the case of the multi-layer cell graft, the RPE cells can be provided as a monolayer, preferably a polarized monolayer.

Yet another aspect of the invention provides methods for treating diseases and disorders caused by loss of photoreceptors in a patient, comprising administering such pharmaceutical preparations as described herein, such as preparations of photoreceptor progenitor cells or photoreceptor cells, or both. The preparations can be injected locally, such as into the sub-retinal space of the patient's eye, into the vitreous of the patients, or delivered systemically or into other body cavities where the cells can persist.

The diseases or disorders caused by loss of photoreceptors include macular degeneration such as age-related macular degeneration, whether at early or late stage, and retinitis pigmentosa. The diseases or disorders may be wet or dry age-related macular degeneration. The diseases or disorders may be myopic macular degeneration. The diseases or disorders may be Stargardt disease. In some instances, the patient has been diagnosed with early or intermediate stage age-related macular degeneration, and/or the photoreceptor cells and/or photoreceptor progenitors provided herein are administered during such early or intermediate stage. In some embodiments, the diseases or disorders may be retinitis pigmentosa.

In some embodiments, the loss of photoreceptors is a complete loss of photoreceptors. In some embodiments, the patient has eyesight of 20/60 or worse including 20/80 or worse, 20/100 or worse, 20/120 or worse, 20/140 or worse, 20/160 or worse, 20/180 or worse, 20/200 or worse, 20/400 or worse, 20/800 or worse, or 20/1000 or worse.

In some embodiments, the photoreceptor cells and/or the photoreceptor progenitors are administered as a dissociated cell suspension, optionally together with other cells such as retinal pigment epithelium (RPE) cells or RPE progenitors. In some embodiments, the photoreceptor cells and/or the photoreceptor progenitors are administered on a monolayer of RPE cells and/or RPE progenitor cells. In some embodiments, the photoreceptor cells and/or the photoreceptor progenitors are administered together with yet other cells, such as retinal ganglion cells and/or retinal ganglion progenitor cells, optionally with RPE cells and/or RPE progenitor cells, optionally as a dissociated cell suspension, an aggregated cell suspension, or a multilayer, optionally in the presence of a matrix or substrate. Any of these cell populations may be administered conjointly with a therapeutic agent, such as but not limited to drugs recited herein. In some embodiments, these cell populations are administered subretinally.

In certain embodiments, the invention provides a method of producing photoreceptor progenitor cells, comprising the steps of (a) culturing eye field progenitor cells, preferably as cells clusters and preferably under low adherence or non-adherent conditions, in a neural differentiation media for a period of time sufficient for the cell clusters to form individual cell spheres;

(b) culturing the cell spheres in a neural differentiation media under adherent conditions, preferably on a matrix (such as a biomaterial scaffold) until a majority of cells in the culture are retinal neural progenitor cells characterized as PAX6+, CHX10+ and SOX2−;

(c) thereafter, alternating culture conditions one or more times between low adherence or non-adherent conditions for a period of time sufficient for the retinal neural progenitor cells to form individual cell spheres, and then culturing the retinal neural progenitor cell containing cell spheres under adherent conditions, which alternating culture conditions are continued until a majority of the cells are photoreceptor progenitor cells.

In preferred embodiments, the eye field progenitor cells are characterized, such as immunocytochemically, as PAX6+ and RX1+ and OCT4− and NANOG−, and even more preferably are also characterized as Six3+, Six6+, Lhx2+, Tbx3+, SOX2+ and Nestin+, such as may be determined by immunostaining and/or flow cytometry or other standard assay used characterized marker expression in cells.

In preferred embodiments, the photoreceptor progenitor cells are characterized, such as immunocytochemically, as PAX6+ and CHX10− (such as may be determined by immunostaining and/or flow cytometry or other standard assay used characterized marker expression in cells), and even more preferably are also characterized as mRNA transcript positive for Mash1, Nr2e3, Trβ2, RORβ and NRL as detected by qPCR, In preferred embodiments, the photoreceptor progenitor cells are characterized as able to differentiate into photoreceptor cells upon treatment with retinoic acid.

In preferred embodiments, the photoreceptor progenitor cells maintain plasticity to differentiate into both rods and cones.

In preferred embodiments, the photoreceptor progenitor cells, when transplanted into the subretinal space of ELOVL4-TG2 mice, migrate to the outer nucleated layer and improve scotopic and photopic ERG responses in the ELOVL4-TG2 mice relative to control (no cells injected) ELOVL4-TG2 mice.

In certain embodiments, the adherent conditions include a culture system having a surface to which the cells can adhere that includes an adherent material, which may be, merely to illustrate, comprises one or more of a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a biomaterial scaffold, a poly L lactic acid, a dextran, an inert metal fiber, silica, natron glass, borosilicate glass, chitosan, or a vegetable sponge. In some embodiments, the adherent material is electrostatically charged. In certain embodiments, the biomaterial scaffold is extracellular matrix, such as collagen (such as collagen type IV or type I), 804G-derived matrix, fibronectin, vitronectin, chondronectin, laminin or Matrigel™. In other embodiments, the biomaterial is gelatin, alginate, polyglycolide, fibrin, or self-assembling peptides, In certain embodiments, the eye field progenitor cells, and as a consequence the retinal neural progenitor cells and photoreceptor progenitor cells, are derived from pluripotent stem cells, such as embryonic stem cells or induced pluripotent stem cells.

In preferred embodiments, the resulting preparation of photoreceptor progenitor cells, are provided substantially free of pluripotent stem cells, i.e., include less than 10% pluripotent stem cells, and even more preferably less than less than 5%, 2%, 1%, 0.1% or even less than 0.01% pluripotent stem cells.

In preferred embodiments, the resulting preparation of photoreceptor progenitor cells, are provided substantially free of eye field progenitor cells and retinal neural progenitor cells, i.e., include less than 10% or either of those cells, and even more preferably less than less than 5%, 2%, 1%, 0.1% or even less than 0.01% eye field progenitor cells and retinal neural progenitor cells.

In preferred embodiments, cellular component of the resulting preparation of photoreceptor progenitor cells is at least 50% pure with respect to other cell types (i.e., cells which are not photoreceptor progenitor cells), and preferably at least 75%, at least 85%, at least 95%, at least 99% or about 100% pure.

In certain embodiments, the method includes the further step of cryopreserving the photoreceptor progenitor cells. The cells are preferably frozen in a cryopreservative which is compatible with ultimately thawing the frozen cells and, after optionally washing the cells to remove the cryopreservative, the photoreceptors retaining at least 25% cell viability (such as based on culture efficiency), and more preferably at least 50%, 60%, 70%, 80% or even at least 90% cell viability.

Various of the progenitor cells as well as the photoreceptor cells may be cryopreserved. In some embodiments, the photoreceptor progenitor cells are cryopreserved as spheres.

In certain embodiments, the neural differentiation media (or medium as it is sometimes referred to herein) may comprise D-glucose, penicillin, streptomycin, GlutaMAX™, N2 supplement, B27 supplement, MEM non-essential amino acids solution and optionally including Noggin.

The neural differentiation media may include agents which activate the Notch pathway, such as Notch ligands or antibodies.

In certain embodiments, the neural differentiation media may be an essentially serum free medium, such as a MEDII conditioned medium. In certain embodiments, the neural differentiation media comprises DMEM/F12, FGF-2 and a MEDII conditioned medium. In certain embodiments, the neural differentiation media is between approximately 10% to approximately 50%>MEDII conditioned medium. In certain embodiments, the MEDII conditioned medium is a Hep G2 conditioned medium. The MEDII medium may comprise a large molecular weight extracellular matrix protein. The MEDII medium may comprise a low molecular weight component comprising proline.

In certain embodiments, the neural differentiation media is essentially serum free cell differentiation environment comprises less than 5% serum.

In certain embodiments, the neural differentiation media is essentially LIF free.

The neural differentiation media may also comprise various supplements such as B27 supplement (Invitrogen) and N2 supplement (also from Invitrogen). B27 supplement contains, amongst other constituents, SOD, catalase and other anti-oxidants (GSH), and unique fatty acids, such as linoleic acid, linolenic acid, lipoic acids. The N2 supplement can be replaced with, for example, the following cocktail: transferrin (10 g/L), insulin (500 mg/L), progesterone (0.63 mg/L), putrescine (1611 mg/L) and selenite (0.52 mg/L).

In certain embodiments of the foregoing aspects and embodiments, the photoreceptor progenitor cells are differentiated from a pluripotent stem cell source, such as a pluripotent stem cell that expresses OCT4, alkaline phosphatase, SOX2, SSEA-3, SSEA-4, TRA-1-60, and TRA-1-81 (such as, but not limited to, an embryonic stem (ES) cell line or induced pluripotency stem (iPS) cell line), and even more preferably from a common pluripotent stem cell source.

In certain embodiments of the foregoing aspects and embodiments, the photoreceptor progenitor cells have a mean terminal restriction fragment length (TRF) that is longer than 7 kb, 7.5 kb, 8 kb, 8.5 kb, 9 kb, 9.5 kb, 10 kb, 10.5 kb, 11 kb, 11.5 kb or even 12 kb.

In certain embodiments of the foregoing aspects and embodiments, a preparation is suitable for administration to a human patient, and more preferably pyrogen-free and/or free of non-human animal products.

In certain embodiments of the foregoing aspects and embodiments, a preparation is suitable for administration to a non-human veterinarian mammal, such as but not limited to a dog, cat or horse.

In one aspect, the disclosure provides a method of producing eye field progenitor cells, comprising (a) culturing pluripotent stem cells in a retinal induction culture medium. Said pluripotent stem cells may be human.

Said retinal induction culture medium may comprise insulin. Said insulin may be human. Said insulin may be present in a concentration of about 5-50 ug/ml human insulin or about 25 ug/ml. Said retinal induction culture medium may comprise DMEM/F12, DMEM/high glucose, or DMEM/knock-out.

Said retinal induction culture medium may comprise D-glucose. The retinal induction culture medium may comprise about 4.5 g/L D-glucose or between about 4 and about 5 g/L D-glucose.

The retinal induction culture medium may comprise one or more antibiotics. Said antibiotics may include one or both of penicillin and streptomycin, optionally in concentrations of about 0-100 units/ml of penicillin and optionally about 0-100 µg/ml of streptomycin, and further optionally in concentrations of about 100 units/ml of penicillin and optionally about 100 µg/ml of streptomycin.

The retinal induction culture medium may comprise N2 supplement. Said N2 supplement may be present in a concentration of about 0.1 to 5% or about 1%.

The retinal induction culture medium may comprise B27 supplement. Said B27 supplement may be present in a concentration of about 0.05-2.0% or about 0.2%.

The retinal induction culture medium may comprise non-essential amino acids or MEM non-essential amino acids or glutamine or GlutaMAX™. Said non-essential amino acids or MEM non-essential amino acids may be present in a concentration of about 0.1 mM The retinal induction culture medium may comprise a BMP signaling inhibitor. Said BMP signaling inhibitor may be selected from the group consisting of: Noggin such as Noggin polypeptide, dorsomorphin, LDN-193189, and any combination thereof.

The retinal induction culture medium may comprise Noggin, such as Noggin polypeptide. Said Noggin may be present at a concentration of between about 5-100 ng/ml or about 10-100 ng/ml or about 50 ng/ml.

In some embodiments, the medium may comprise Noggin, DKK1 and IGF-1. In some embodiments, the medium may comprise 5 ng/ml Noggin, 5 ng/ml DKK1, and 5 ng/ml IGF-1.

Said pluripotent stem cells may comprise human ES cells, human iPS cells, or human STAP cells. Said pluripotent stem cells may be cultured under feeder-free and/or xeno-free conditions and/or on a substrate optionally comprising Matrigel™ (a soluble preparation from Engelbreth-Holm-Swarm (EHS) mouse sarcoma cells) and optionally in mTESR1 medium, prior to being cultured in said retinal induction culture medium comprising insulin.

Said retinal induction culture medium may be replaced with fresh retinal induction culture medium daily. Said culturing in step (a) may be continued for about 1-10 days or about 2-7 days, or about 5-6 days.

The method may further comprise (b) culturing the cells in a neural differentiation medium. Said neural differentiation medium may comprise Neurobasal medium.

Said neural differentiation medium may comprise D-glucose. The neural differentiation medium may comprise about 4.5 g/L D-glucose or between about 4 and about 5 g/L D-glucose.

The neural differentiation medium may comprise one or more antibiotics. Said antibiotics may include one or both of penicillin and streptomycin, optionally in concentrations of about 0-100 units/ml of penicillin and optionally about 0-100 µg/ml of streptomycin, and further optionally in concentrations of about 100 units/ml of penicillin and optionally about 100 µg/ml of streptomycin.

The neural differentiation medium may comprise N2 supplement. Said N2 supplement may be present in a concentration of about 0.1 to 5% or about 2%.

The neural differentiation medium may comprise B27 supplement. Said B27 supplement may be present in a concentration of about 0.05-5.0%, about 0.05-2.0% or about 2%.

The neural differentiation medium may comprise non-essential amino acids or MEM non-essential amino acids or glutamine or GlutaMAX™. Said non-essential amino acids or MEM non-essential amino acids may be present in a concentration of about 0.1 mM The neural differentiation culture medium may comprise a BMP signaling inhibitor. Said BMP signaling inhibitor may be selected from the group consisting of: Noggin such as Noggin polypeptide, dorsomorphin, LDN-193189, and any combination thereof.

The neural differentiation culture medium may comprise Noggin, such as Noggin polypeptide. Said Noggin may be present at a concentration of between about 10-100 ng/ml or about 50 ng/ml.

Said cells may be cultured in said neural differentiation medium for about 10-60 days or about 15-35 days or about 24 days.

Said eye field progenitor cells may comprise at least 50%, at least 75%, at least 85%, at least 95%, at least 99% or about 100% of the cells in said culture.

Said eye field progenitor cells express one or both of the markers PAX6 and RX1. Thus, the eye field progenitor cells may be PAX6(+) and/or RX1(+). Said eye field progenitor cells may be one or more of SIX3(+), SIX6(+), LHX2(+), TBX3(+), and/or Nestin(+). Said eye field progenitor cells may be one or more of SOX2(+) and OCT4(−) and Nanog (−). Said eye field progenitor cells may be human.

The method may further comprise differentiating said eye field progenitor cells into retinal neural progenitor cells.

In another aspect, the disclosure provides a composition comprising eye field progenitor cells produced using a method as described herein, e.g., as described in the preceding paragraphs. In another aspect, the disclosure provides a composition comprising eye field progenitor cells, which are optionally human.

Said eye field progenitor cells may be human. Said eye field progenitor cells may comprise at least 50%, at least 75%, at least 85%, at least 95%, at least 99% or about 100% of the cells in said culture. Said eye field progenitor cells express one or both of the markers PAX6 and RX1. Thus, the eye field progenitor cells may be PAX6(+) and/or RX1(+). Said eye field progenitor cells may be one or more of SIX3(+), SIX6(+), LHX2(+), TBX3(+), and/or Nestin(+). Said eye field progenitor cells may be one or more of SOX2(+) and OCT4(−) and Nanog (−). Said eye field progenitor cells may be cryopreserved.

In another aspect, the disclosure provides a method of treatment of an individual in need thereof, comprising administering a composition comprising eye field progenitor cells (e.g., a composition as described herein or a composition produced using a method as described herein) to said individual. Said composition may be administered to the eye, subretinal space, or intravenously. Such individuals may have macular degeneration including age-related macular degeneration, and such macular degeneration may be early or late stage. Such individuals may have retinitis pigmentosa, retinal dysplasia, retinal degeneration, diabetic retinopathy, congenital retinal dystrophy, Leber congenital amaurosis, retinal detachment, glaucoma, or optic neuropathy.

In another aspect, the disclosure provides a method of producing retinal neural progenitor cells or photoreceptor progenitor cells, comprising (a) culturing eye field progenitor cells in a neural differentiation medium. Said neural differentiation medium may comprise Neurobasal medium.

Said neural differentiation medium may comprise D-glucose. The neural differentiation medium may comprise about 4.5 g/L D-glucose or between about 4 and about 5 g/L D-glucose.

The neural differentiation medium may comprise one or more antibiotics. Said antibiotics may include one or both of penicillin and streptomycin, optionally in concentrations of about 0-100 units/ml of penicillin and optionally about 0-100 μg/ml of streptomycin, and further optionally in concentrations of about 100 units/ml of penicillin and optionally about 100 μg/ml of streptomycin.

The neural differentiation medium may comprise N2 supplement. Said N2 supplement may be present in a concentration of about 0.1 to 5% or about 2%.

The neural differentiation medium may comprise B27 supplement. Said B27 supplement may be present in a concentration of about 0.05-5.0%, about 0.05-2.0% or about 2%.

The neural differentiation medium may comprise non-essential amino acids or MEM non-essential amino acids or glutamine or GlutaMAX™. Said non-essential amino acids or MEM non-essential amino acids may be present in a concentration of about 0.1 mM The neural differentiation culture medium optionally does not comprises an exogenously added BMP signaling inhibitor. The neural differentiation medium optionally does not contain exogenously added Noggin, such as Noggin polypeptide.

Step (a) may comprise (i) culturing eye field progenitor cells until the cells form spheres, and (ii) plating the spheres under adherent conditions.

Step (i) may comprise culturing the cells on low-adherent plates. Step (i) may comprise culturing the cells in a hanging drop. The culture of step (i) may be formed by mechanically or enzymatically breaking cultured cells into a single cell suspension. Step (i) may be continued for 1-10, 3-8, or about 5 days.

Step (ii) may comprise plating the spheres on Matrigel™. Step (ii) may comprise plating the spheres on laminin or collagen. Step (ii) may be continued until said culture is confluent.

Steps (i) and (ii) may be repeated in an alternating fashion.

Said cells may be cultured in said neural differentiation medium for about 10-60 days or about 15-35 days or about 25 days.

Said retinal neural progenitor cells may differentiate from said eye field progenitor cells and may be present in increasing numbers in said culture. Said retinal neural progenitor cells may comprise at least 50%, at least 75%, at least 85%, at least 95%, at least 99% or about 100% of the cells in said culture.

Said retinal neural progenitor cells may express one or both of the markers PAX6 and RX1. Thus, the neural progenitor cells may be PAX6(+) and/or CHX10(+). Said retinal neural progenitor cells may be SOX2(−). Said retinal neural progenitor cells may be Tuj1(+) or Tuj1(−).

Said cells may be cultured in said neural differentiation medium for about 10-330 days or about 15-300 days or about 10-100 days or about 15-100 days or about 100 days.

Said photoreceptor progenitor cells differentiate from said retinal neural progenitor cells and may be present in increasing numbers in said culture. Said photoreceptor progenitor cells may comprise at least 50%, at least 75%, at least 85%, at least 95%, at least 99% or about 100% of the cells in said culture.

Said photoreceptor progenitor cells may be PAX6(+) and/or CHX10(−). Said photoreceptor progenitor cells may express one or more of the markers Nr2e3, Trβ2, Mash1, RORβ and/or NRL, and thus may be Nr2e3(+) and/or Trβ2(+) and/or Mash1(+) and/or RORβ(+) and/or NRL(+).

Said cells may be cultured in said neural differentiation medium for at least about 130 days, at least about 160 days, at least about 190 days, or longer, whereby said photoreceptor progenitor cells exhibit decreased or no ability to differentiate into cones while retaining the ability to form rods.

The method may further comprise differentiating said photoreceptor progenitor cells into photoreceptors.

Said eye field progenitor cells may be differentiated from a pluripotent stem cell, such as an ES cell or iPS cell or a STAP cell, which pluripotent stem cell, such as an ES cell or iPS cell or STAP cell, may optionally be human.

In another aspect, said retinal neural progenitor cells may be human.

In another aspect, the disclosure provides a composition comprising retinal neural progenitor cells produced according to any method described herein, e.g., the methods described in the preceding paragraphs. In another aspect, the disclosure provides a composition comprising retinal neural progenitor cells, which are optionally human.

Said retinal neural progenitor cells may comprise at least 50%, at least 75%, at least 85%, at least 95%, at least 99% or about 100% of the cells in said culture.

Said retinal neural progenitor cells may express one or both of the PAX6 and CHX10 markers, and thus may be PAX6(+) and/or CHX10(+). Said retinal neural progenitor cells may be SOX2(−). Said retinal neural progenitor cells may be Tuj1(+) or Tuj1(−).

Said retinal neural progenitor cells may be cryopreserved.

In various of the foregoing aspects and embodiments, the invention further contemplates use of ROCK inhibitors in culture media during various phases of the differentiation, maintenance, and expansion of photoreceptor progenitor and photoreceptor cell cultures. Exemplary ROCK inhibitors include Y-27632, thiazovivin, GSK429286A, and Fasudil. Y-27632 may be used at a concentration ranging from 500 nM to 50 uM. Y-27632 is a selective inhibitor of the Rho associated kinase, p160ROCK and ROCK-II with a Ki value of 140 nm. Y-27632 additionally inhibits PKC, cAMP-dependent protein kinase and myosin light-chain kinase but with greatly diminished Ki values, 26, 25 and >250 µM, respectively.

In another aspect, the disclosure provides a method of treatment of an individual in need thereof, comprising administering a composition comprising retinal neural progenitor cells, e.g., a composition described herein or a composition produced according to a method described herein, to said individual. Said composition may be administered to the eye, subretinal space, or intravenously. Said photoreceptor progenitor cells may be human. Such individuals may have macular degeneration including age-related macular degeneration, and such macular degeneration may be early or late stage. Such individuals may have retinitis pigmentosa, retinal dysplasia, retinal degeneration, diabetic retinopathy, congenital retinal dystrophy, Leber congenital amaurosis, retinal detachment, glaucoma, or optic neuropathy.

In another aspect, the disclosure provides a composition comprising photoreceptor progenitor cells produced according to a method described herein, e.g., a method according to the preceding paragraphs. In another aspect, the disclosure provides a composition comprising photoreceptor progenitor cells, which are optionally human.

Said photoreceptor progenitor cells may comprise at least 50%, at least 75%, at least 85%, at least 95%, at least 99% or about 100% of the cells in said culture.

Said photoreceptor progenitor cells may be PAX6(+) and/or CHX10(−). Said photoreceptor progenitor cells express one or more of the Nr2e3, Trβ2, Mash1, RORβ and/or NRL markers, and thus may be Nr2e3(+) and/or Trβ2(+) and/or Mash1(+) and/or RORβ(+) and/or NRL(+).

Said photoreceptor progenitor cells may be cryopreserved.

In another aspect, the disclosure provides a method of treatment of an individual in need thereof, comprising administering a composition comprising photoreceptor progenitor cells, e.g., a composition as described herein e.g., in the preceding paragraphs, or a composition produced according to the methods described herein e.g., in the preceding paragraphs, to said individual. Said composition may be administered to the eye, subretinal space, or intravenously. Such individuals may have macular degeneration including age-related macular degeneration, and such macular degeneration may be early or late stage. Such individuals may have retinitis pigmentosa, retinal dysplasia, retinal degeneration, diabetic retinopathy, congenital retinal dystrophy, Leber congenital amaurosis, retinal detachment, glaucoma, or optic neuropathy.

In another aspect, the disclosure provides a method of producing photoreceptor cells, comprising (a) culturing photoreceptor progenitor cells in a photoreceptor differentiation medium. Said photoreceptor differentiation medium may comprise Neurobasal medium.

Said photoreceptor differentiation medium may comprise D-glucose. The photoreceptor differentiation medium may comprise about 4.5 g/L D-glucose or between about 4 and about 5 g/L D-glucose.

The photoreceptor differentiation medium may comprise one or more antibiotics. Said antibiotics may include one or more or all of penicillin and streptomycin, optionally in concentrations of about 0-100 units/ml of penicillin and optionally about 0-100 µg/ml of streptomycin, and further optionally in concentrations of about 100 units/ml of penicillin and optionally about 100 µg/ml of streptomycin.

The photoreceptor differentiation medium may comprise N2 supplement. Said N2 supplement may be present in a concentration of about 0.1 to 5% or about 2%.

The photoreceptor differentiation medium may comprise B27 supplement (e.g., formula number 080085-SA). Said B27 supplement may be present in a concentration of about 0.05-5.0%, about 0.05-2.0% or about 2%.

The photoreceptor differentiation medium may comprise non-essential amino acids or MEM non-essential amino acids or glutamine or GlutaMAX™. GlutaMAX™ is L-alanyl-L-glutamine, which is a stabilized form of L-glutamine. Said non-essential amino acids or MEM non-essential amino acids may be present in a concentration of about 0.1 mM Said photoreceptor differentiation medium may comprise forskolin, or other factors that increase cAMP levels. Said forskolin may be present in the photoreceptor differentiation medium at a concentration between about 1-100 µM or about 5 µM.

Said photoreceptor differentiation medium may comprise BDNF. Said BDNF may be present in the photoreceptor differentiation medium at a concentration between about 1-100 ng/ml or about 10 ng/ml.

Said photoreceptor differentiation medium may comprise CNTF. Said CNTF may be present in the photoreceptor differentiation medium at a concentration between about 1-100 ng/ml or about 10 ng/ml.

Said photoreceptor differentiation medium may comprise LIF. Said LIF may be present in the photoreceptor differentiation medium at a concentration between about 5-50 ng/ml or about 10 ng/ml.

Said photoreceptor differentiation medium may comprise (N—[N-(3,5-difluorophenacetyl)-1-alanyl]-S-phenylglycine t-butyl ester) (DAPT) or other Notch pathway inhibitor or Notch inhibitor (such as Notch blocking antibody or antibody fragment, Notch negative regulatory region antibody or antibody fragment, alpha-secretase inhibitor, gamma-secretase inhibitor, stapled peptide, small molecule blockers and siRNA, shRNA and miRNA). Said DAPT may be present in the photoreceptor differentiation medium at a concentration between about 1-100 µM or about 10 µM.

Said photoreceptor progenitor cells may be differentiated from retinal neural progenitor cells, which are optionally human. Said photoreceptor cells may be human.

In some embodiment, photoreceptor progenitor cells are pre-treated with retinoic acid and taurine in ND medium, prior to culture in the photoreceptor differentiation medium. The retinoic acid may be used at a concentration of about 0.2-10 µM and taurine may be used at a concentration of about 20-500 µM. This culture step may occur for about 1-2 weeks, in some embodiments. The medium may be changed (e.g., half change) every 2 days, in some instances. The medium may then be changed to ND medium lacking retinoic acid and taurine, and the cells may be cultured for about an additional 1-2 weeks, or until they become confluent.

In another aspect, the disclosure provides a composition comprising photoreceptor cells produced according to a method as described herein, e.g., in the preceding paragraphs, which are optionally human.

Said photoreceptor cells may be PAX6(−). Said photoreceptor cells may comprise at least 50%, at least 75%, at least 85%, at least 95%, at least 99% or about 100% of the cells in said culture. Said photoreceptor cells may be cryopreserved.

In another aspect, the disclosure provides a method of treatment of an individual in need thereof, comprising administering a composition comprising photoreceptor cells, e.g., a composition as described herein such as in the preceding paragraphs or a composition produced by a method as described herein e.g., in the preceding paragraphs, to said individual. Said composition may be administered to the eye, subretinal space, or intravenously. Such individuals may have macular degeneration including age-related macular degeneration, and such macular degeneration may be early or late stage. Such individuals may have retinitis pigmentosa, retinal dysplasia, retinal degeneration, diabetic retinopathy, congenital retinal dystrophy, Leber congenital amaurosis, retinal detachment, glaucoma, or optic neuropathy.

In another embodiment, the invention is directed to a substantially pure preparation of photoreceptor progenitor cells (PRPCs) or photoreceptor cells (PRs) of human origin, preferably non-donor derived photoreceptor progenitor cells or photoreceptor cells, originating from cells not grown on a mouse fibroblast feeder platform. For example, the preparation may be 85%-95% pure. In an embodiment, the invention is directed to a method of preparing the substantially pure preparation of PRPCs or PRs of human origin which omits the need for cells derived from a mouse fibroblast feeder platform. Replacing a feeder system with the methods of the present invention produces a greater homogeneity of photoreceptors cells, e.g., at 75%-100% or 85%-95%. The differentiation of the feeder-free stem cells can also occur in the absence of the introduction of exogenous inducing factors, which is a substantial improvement over the prior art. The optional addition of Noggin, however, can accelerate differentiation of the stem cells, even though it is not necessary for differentiation to occur. The resultant photoreceptor progenitor cells are uniquely characterized immunocytochemically as PAX6 positive (PAX6(+)) and CHX10 negative (CHX10(−)).

Another aspect provides a substantially pure preparation of photoreceptor progenitor cells, comprising: a plurality of photoreceptor progenitor cells, and a medium suitable for maintaining the viability of the photoreceptor progenitor cells, wherein greater than 90% of the cells in the preparation are immunocytochemically PAX6+ and CHX10−, and mRNA transcript positive for MASH1 as detected by qPCR.

Another aspect provides a preparation of photoreceptor progenitor cells, comprising: a plurality of cells containing at least 50 percent photoreceptor progenitor cells, and a medium suitable for maintaining the viability of the photoreceptor progenitor cells, wherein the photoreceptor progenitor cells immunocytochemically PAX6(+) and CHX10 (−), and mRNA transcript positive for MASH1 as detected by qPCR.

Another aspect provides a preparation of photoreceptor progenitor cells, comprising: a plurality of photoreceptor progenitor cells substantially free of pluripotent stem cells, retinal ganglion cells, mature photoreceptors, and/or amacrine cells; and a medium suitable for maintaining the viability of the photoreceptor progenitor cells, wherein the photoreceptor progenitor cells are immunocytochemically PAX6(+) and CHX10(−), and mRNA transcript positive for MASH1 as detected by qPCR.

Another aspect provides a pharmaceutical preparation of photoreceptor progenitor cells that is suitable for use in a mammalian patient, comprising: (a) a plurality of photoreceptor progenitor cells, wherein greater than 90% of the cells in the preparation are immunocytochemically PAX6+ and CHX10−, and mRNA transcript positive for MASH1 as detected by qPCR; and (b) a pharmaceutically acceptable carrier for maintaining the viability of the photoreceptor progenitor cells for transplantation into a mammalian patient.

Another aspect provides a cryogenic cell preparation comprising at least $10^9$ photoreceptor progenitor cells (PRPCs), comprising: (a) a plurality of photoreceptor progenitor cells, wherein greater than 90% of the cells in the preparation are immunocytochemically PAX6+ and CHX10−, and mRNA transcript positive for MASH1 as detected by qPCR; and (b) a cryopreservative system compatible with the viability of the photoreceptor progenitor cells upon thaw.

In some embodiments, the photoreceptor progenitor cells are derived from pluripotent stem cells. In some embodiments, the pluripotent stem cells are selected from the group consisting of human embryonic stem cells and induced pluripotent stem cells.

In some embodiments, the photoreceptor progenitor cells are human cells.

In some embodiments, a majority of the photoreceptor progenitor cells are mRNA transcript positive for Nr2e3, Trβ2, RORβ and NRL as detected by qPCR.

In some embodiments, the photoreceptor progenitor cells express at least 2-fold more, relative to retinal neural progenitor cells, of one or more markers selected from uPA, Tenascin-C, CXCL16, CX3CL1 and Chitinase 3 like-1, as detected by immunoassay of secreted proteins or mRNA transcript levels by qPCR.

In some embodiments, the photoreceptor progenitor cells have replicative capacity to undergo at least 20 population doublings in cell culture with less than 25 percent of the cells undergoing cell death, senescing or differentiating into phenotypically non-photoreceptor cells by the $20^{th}$ doubling.

In some embodiments, the photoreceptor progenitor cells have transferrin protein and or transferrin mRNA levels that are at least 25 percent less than glyceraldehyde 3-phosphate dehydrogenase protein or mRNA levels respectively.

In some embodiments, the photoreceptor progenitor cells are HLA-genotypically identical. In some embodiments, the photoreceptor progenitor cells are genomically identical.

In some embodiments, the photoreceptor progenitor cells have a mean terminal restriction fragment length (TRF) that is longer than 8 kb.

In some embodiments, the photoreceptor progenitor cells have a statistically significant decreased content and/or enzymatic activity, relative to fetal-derived photoreceptors, of proteins involved in one or more of (i) cell cycle regulation and cellular aging, (ii) cellular energy and/or lipid metabolism, and (iii) apoptosis.

In some embodiments, the photoreceptor progenitor cells have a statistically significant increased content and/or enzymatic activity of proteins involved in cytoskeleton structure and cellular dynamics relating thereto, relative to fetal derived photoreceptors.

In some embodiments, the preparation is suitable for administration to a human patient. In some embodiments, the preparation is suitable for administration to a non-human veterinarian patient.

In some embodiments, the photoreceptor progenitor cells are differentiated from a common pluripotent stem cell source.

In some embodiments, the medium suitable for maintaining the viability of the photoreceptor progenitor cells is selected from the group consisting of a culture medium, a cryopreservative, and a biocompatible injection medium suitable for injection in a human patient.

In some embodiments, the photoreceptor progenitor cells maintain plasticity to differentiate into both rods and cones.

In some embodiments, the photoreceptor progenitor cells, when transplanted into the subretinal space of ELOVL4-TG2 mice, migrate to the outer nucleated layer and improve scotopic and photopic ERG responses in the ELOVL4-TG2 mice.

In some embodiments, the preparation is pyrogen- and mycogen-free.

In some embodiments, the photoreceptor progenitor cells have phagocytic activity, optionally the ability to phagocytose isolated photoreceptor outer segments, pHrodo™ Red E. coli BioParticles or both.

In some embodiments, the photoreceptor progenitor cells secrete one or more neuroprotective factors.

Another aspect provides a substantially pure preparation of pluripotent stem cell-derived photoreceptor cells comprising: (a) pluripotent stem cell derived photoreceptor cells, wherein greater than 90% of the cells are immunocytochemically PAX6+, CHX10− and are rhodopsin+ and/or opsin+; and (b) a medium suitable for maintaining the viability of the stem cell derived photoreceptor cells.

Another aspect provides a pharmaceutical preparation of photoreceptors that is suitable for use in a mammalian patient, comprising: (a) pluripotent stem cell derived photoreceptor cells, wherein greater than 90% of the cells are immunocytochemically PAX6+, CHX10− and are rhodopsin+ and/or opsin+; and (b) a pharmaceutically acceptable carrier for maintaining the viability of the photoreceptor cells for transplantation into a mammalian patient.

Another aspect provides a method of treating a disease or disorder caused by loss of photoreceptors in a patient, comprising administering the pharmaceutical preparation of photoreceptor progenitor cells of claim 4 or the pharmaceutical preparation of photoreceptor cells of claim 28, or both.

In some embodiments, the preparation of cells are injected into the sub-retinal space of the patient.

Another aspect provides a method of producing photoreceptor progenitor cells, comprising the steps of culturing eye field progenitor cells under culture conditions alternating between low adherence or non-adherent conditions for a period of time sufficient to form individual cell spheres, and then adherent conditions, which alternating culture conditions are continued until a majority of the cells are photoreceptor progenitor cells, wherein the photoreceptor progenitor cells are characterized as PAX6(+) and CHX10(−), and wherein the photoreceptor progenitor cells differentiate into photoreceptor cells upon treatment with retinoic acid.

Another aspect provides a method of producing photoreceptor progenitor cells, comprising the steps of (a) culturing eye field progenitor cells, preferably as cells clusters and preferably under low adherence or non-adherent conditions, in a neural differentiation media for a period of time sufficient for the cell clusters to form individual cell spheres, wherein the eye field progenitor cells are characterized as PAX6(+) and RX1(+) and OCT4(−) and NANOG(−), and preferably are also characterized as SIX3(+), SIX6(+), LHX2(+), TBX3(+), SOX2(+) and Nestin+, as determined by immunostaining and/or flow cytometry; (b) culturing the cell spheres in a neural differentiation media under adherent conditions, preferably on a biomaterial scaffold such as gelatin, alginate, collagen type 1, Matrigel™, polyglycolide, collagen, fibrin, or self-assembling peptides, until a majority of cells in the culture are retinal neural progenitor cells characterized as PAX6(+), CHX10(+) and SOX2(−); and (c) thereafter, alternating culture conditions one or more times between low adherence or non-adherent conditions for a period of time sufficient for the retinal neural progenitor cells to form individual cell spheres, and then culturing the retinal neural progenitor cell containing cell spheres under adherent conditions, which alternating culture conditions are continued until a majority of the cells are photoreceptor progenitor cells, wherein the photoreceptor progenitor cells are characterized as PAX6(+) and CHX10(−), and preferably are also characterized as mRNA transcript positive for Mash1, Nr2e3, Trβ2, RORβ and NRL as detected by qPCR, and wherein the photoreceptor progenitor cells differentiate into photoreceptor cells upon treatment with retinoic acid.

In some embodiments, the photoreceptor progenitor cells are derived from pluripotent stem cells. In some embodiments, the pluripotent stem cells are embryonic stem cells or induced pluripotent stem cells, optionally human embryonic stem cells or human induced pluripotent stem cells. In some embodiments, the photoreceptor progenitor cells are provided substantially free of pluripotent stem cells.

In some embodiments, the photoreceptor progenitor cells are at least 50% pure, at least 75%, at least 85%, at least 95%, at least 99% or about 100% pure with respect to other cell types.

In some embodiments, the method includes the further step of cryopreserving the photoreceptor progenitor cells.

Another aspect provides a method for preparing a substantially pure culture of pluripotent stem cell-derived photoreceptor progenitor cells comprising: (a) culturing pluripotent stem cells in a feeder-free system to produce one or more eye field progenitor cells; (b) culturing said one or more eye field progenitor cells to produce retinal neural progenitor cells that are PAX6+ and CHX10+; (c) culturing said retinal neural progenitor cells to produce photoreceptor progenitor cells (PRPCs) that are PAX6+ and CHX10−. Other aspects provide preparations of cells comprising EFPs, RNPCs, PhRPs or photoreceptor-like cells, wherein the population is homogeneous or nearly homogeneous (e.g., greater than 90%, 91%, 92%, 93%, 94%, 95%, 96%, 97%, 98%, 99% or more of the cells are phenotypically defined as one of these precursor populations as provided herein).

Another aspect provides a method of treating a disease or disorder caused by loss of photoreceptors, comprising administering to the subject a preparation of photoreceptor progenitor cells wherein at least 70% of the cells in the preparation are immunocytochemically PAX6(+) and CHX10(−), and mRNA transcript positive for MASH1 as detected by qPCR, wherein the subject is characterized as having eyesight of 20/200 or worse prior to administration.

In some embodiments, the subject is human and the photoreceptor progenitor cells are human.

In some embodiments, the photoreceptor progenitor cells are derived in vitro from pluripotent stem cells. In some embodiments, the pluripotent stem cells are selected from the group consisting of embryonic stem cells and induced pluripotent stem cells.

In some embodiments, the photoreceptor progenitor cells are HLA-genotypically identical. In some embodiments, the photoreceptor progenitor cells are genomically identical. In some embodiments, a majority of the photoreceptor progenitor cells in the preparation is mRNA transcript positive for Nr2e3, Trβ2, RORβ and NRL as detected by qPCR. In some embodiments, the photoreceptor progenitor cells express at least 2-fold more, relative to retinal neural progenitor cells, of one or more markers selected from uPA, Tenascin-C, CXCL16, CX3CL1 and Chitinase 3 like-1, as detected by immunoassay of secreted proteins or mRNA transcript levels by qPCR. In some embodiments, the photoreceptor progenitor cells have replicative capacity to undergo at least 20 population doublings in cell culture with less than 25 percent of the cells undergoing cell death, senescing or differentiating into phenotypically non-photoreceptor cells by the 20$^{th}$ doubling. In some embodiments, the photoreceptor progenitor cells have transferrin protein and or transferrin mRNA levels that are at least 25 percent less than glyceraldehyde 3-phosphate dehydrogenase protein or mRNA levels respectively. In some embodiments, the photoreceptor progenitor cells maintain plasticity to differentiate into both rods and cones.

In some embodiments, the photoreceptor progenitor cells are administered to the sub-retinal space of the subject. In some embodiments, the photoreceptor progenitor cells are administered in suspension. In some embodiments, the photoreceptor progenitor cells are administered on a matrix or a support.

In some embodiments, the photoreceptor progenitor cells are provided substantially free of pluripotent stem cells. In some embodiments, the photoreceptor progenitor cells are at least 75%, at least 85%, at least 95%, at least 99% or about 100% pure with respect to other cell types. In some embodiments, the photoreceptor progenitor cells are administered at a dose of about $10^3$-$10^4$ cells, or a dose of about $10^5$-$10^6$ cells, or a dose of about $10^6$-$10^7$ cells, a dose of about $10^7$-$10^8$ cells.

In some embodiments, the subject is characterized as having eyesight worse than 20/200. In some embodiments, the subject is characterized as having eyesight of 20/400 or worse. In some embodiments, the subject is characterized as having eyesight of 20/800 or worse. In some embodiments, the subject is characterized as having eyesight of 20/1000 or worse.

Another aspect provides a synchronized photoreceptor progenitor cell population wherein the population is cell cycle synchronized.

Another aspect provides a synchronized photoreceptor progenitor cell population wherein all the cells in the population express NRL and TRβ2.

BRIEF DESCRIPTION OF THE DRAWINGS

FIGS. 21A-E show the components of culture media and media supplements used in the Examples.

FIGS. 32A-D. In vitro differentiation of human embryonic stem cells towards retinal neural progenitors. (A) Flow cytometry analyses show dynamic changes of PAX6 and RX1 expression on cells from day 9 to day 13 after in vitro differentiation. (B) Immunofluorescence staining shows co-expression of PAX6 and RX1 in day 13 eye field progenitors. (C) Quantification of PAX6 and RX1 double positive eye field progenitors by flow cytometry analysis which shows >90% of them expressing both PAX6 and RX1 proteins. (D) Immunofluorescence staining shows homogeneous co-expression of PAX6 and CHX10 on retinal neuronal progenitor cells (RNPC) at about day 30 after initial differentiation in vitro. Scale bar, 50 µm.

FIGS. 33A-D. In vitro differentiation of retinal neural progenitors towards photoreceptor progenitors. (A) Immunofluorescence staining shows the expression of transcription factors PAX6, CRX, NRL, RXR-γ, NR2E3 and CHX10 in PhRPs at 90-100 days after in vitro differentiation as is apparent from the color version of the Figure. The upper right corner of the CHX10 image shows positive expression of CHX10 in RNPCs at day 30, but negative in PhRPs. No positive stain was observed for neuN antibody in these cells (The upper right corner of the neuN image shows positive expression of neuN in mature mouse cerebellar granule neurons). $2^{nd}$ antibody only also shows no stain. (B) Real time-PCR analysis shows up-regulation of photoreceptor transcription factors ASCL1 and RORβ in PhRPs. (C) Immunofluorescence staining shows low level expression of recoverin in the cytoplasm of PhRPs. (D) Real time-PCR confirms up-regulation of photoreceptor genes rhodoposin, opsin and recoverin in PhRPs as compared to RNPCs. Scale bar, 50 µm. All nuclei are counterstained in blue with DAPI as is apparent from the color version of the Figure.

FIGS. 34A-D. In vitro generation of mature photoreceptor-like cells from human ESC/iPS-derived PhRPs. (A) Expression of rod photoreceptor markers, rhodopsin, recoverin and PDE6α and (B) cone photoreceptor markers M-opsin (left panel), Rhodopsin (middle panel) and colocalization of rhodopsin (red) and M-opsin (green, right panel of B) in human ESC-derived photoreceptors after two week in vitro maturation of PhRPs (100 days of in vitro differentiation) in photoreceptor differentiation medium. Scale bar, 50 µm. (C) Expression of rhodopsin and PDE6α in human iPSC-derived photoreceptors after two week in vitro maturation. Scale bar, 20 µm. (D) Human ESC-derived PhRPs cultured in vitro for 8 months differentiate into rod photoreceptors expressing rhodopsin and PDE6α, no cone pigment gene expression is detectable in these cells. Scale bar, 50 µm. All nuclei are counterstained in blue with DAPI. Expression of rhodopsin, recoverin, M-opsin, DAPI and PDE6α is apparent from the color version of the Figure.

FIGS. 35A-E. Transplanted ESC-PhRPs and iPSC-PhRPs survive in the subretinal space of rd1 mice. Scanning laser ophthalmoscopy (SLO) was performed in vivo three weeks post-transplantation to assess the extent of surviving donor cells; GFP positive cells are observed in AF mode as white dots or clusters (black areas represent areas of retina which were not seeded with transplanted cells, due to incomplete detachment of the retina around the optic nerve head). Representative NIR and AF fundus images of rd1 mice show a homogeneous presence of GFP+ cells in the two treatment groups: ESC-PhRPs (A) and iPSC-PhRPs (B). Histological assessment 3 weeks post transplantation revealed ESC-PhRP (C) and iPSC-PhRP (D) derived cell layers (green) between the RPE and INL of the rd1 retina, replacing the absent ONL in the adult rd1, as is apparent from the color version of the Figure. (E) GFP+ cells were stained with human nuclear antigen (HNA) which co-localized with GFP, indicating that the GFP signal observed in vivo in treated animals was indeed an indicator of transplanted human PhRPs. Scale bar, 25 µm. RPE=retinal pigment epithelium; INL=inner nuclear layer; NIR=near-infrared; AF=autofluorescence; HNA=human nuclear antigen.

FIGS. 36A-H. Transplanted ESC-PhRPs and iPSC-PhRPs express mature photoreceptor markers in vivo. Immunofluorescence staining 3 weeks post-transplantation shows expression of mature photoreceptor markers in transplanted human PhRPs (green) as is apparent from the color version of the Figure. In all images cells are located in the subretinal space and oriented so that the host INL is located at the top of the image and the RPE at the bottom. The pan-photoreceptor marker recoverin was observed within the reconstructed layer of cells in animals treated with both ESC-PhRPs (A) and iPSC-PhRPs (B). The dashed line represents the interface between the host ONL and the engrafted layer of human cells. The rod specific enzyme phosphodiesterase β6 (PDE6b), which is necessary in phototransduction and is absent in rd1 mice due to mutation, was reinstated in the retina and located in the outer processes of transplanted ESC-PhRPs (C) and iPSC-PhRPs (D). The rod specific protein rhodopsin, which is normally located in outer segment membrane disk, was also observed in outer segments of ESC-PhRPs (E) and iPSC-PhRPs (F). The cone specific marker cone-arrestin was observed in maturing ESC-PhRPs (G) and iPSC-PhRPs (H). The dashed line represents the interface between the host ONL and the engrafted layer of human cells. Scale bar, 20 µm. RPE, retinal pigment epithelium; INL, inner nuclear layer.

FIGS. 37A-I. Recovery of basic visual responses in rd1 mice following transplantation of human PhRPs correlates to number of engrafted cells. (A) Schematic of the optomotor (OMR) test arena and expected response to the direction of drum rotation. (B) Mean OMR 3 weeks post-transplantation indicating an improvement in OMR driven by treated eyes (dark grey) compared to paired untreated eyes (light grey) after transplantation of ESC-PhRPs (paired sample t-test, t=2.86, p=0.024) and iPSC-PhRPs (paired sample t-test, t=5.02, p=0.002), In the sham treated group there were no differences in OMR driven by treated and untreated eyes (paired sample t test, t=0.31 ns). Furthermore, OMR response was improved in PhRP treatment groups compared to sham treatment (one way-ANOVA, F=7.8, p=0.003), with an increase in the response in both ESC-PhRP (p<0.05) and iPSC-PhRP (p<0.005) treated animals (Bonferroni test for multiple comparisons). (C) A positive correlation was found between number of head tracks and number of GFP+ cells in animals treated with ESC-PhRPs (n=8, $R^2$=0.729, F=16.13, p<0.01) and (D) iPSC-PhRPs (n=8, $R^2$=0.612, F=9.46, p<0.05). (*p<0.5, **p<0.01). (E) Schematic of the light avoidance apparatus. (F) There were no differences between the three groups in mean light avoidance responses (F=1.43, p=0.261 [ns]). However, a positive correlation was observed between number of GFP+ cells and light avoidance behavior in individual animals of (G) ESC-PhRP ($R^2$=0.729, F=16.13, p<0.01) and (H) iPSC-PhRP treated group ($R^2$=0.612, F=9.46, p<0.05). (I) Comparing only animals with above-median numbers of GFP+ cells (encircled in C and D) a difference emerged between the three groups ($X^2$=6 (df2), p<0.05) showing improvement in ESC-PhRP treated (n=4, p<0.05) and iPSC-PhRP treated (n=4, p<0.05) subgroups. The dashed line represents the mean response of age-matched wild-type mice. Error bars represent ±1 S.E.M.

DETAILED DESCRIPTION

The invention provides methods for generating photoreceptor cells (PRC) and photoreceptor progenitor cells (PRPC). These methods involve in vitro differentiation from earlier progenitors including pluripotent stem cells, eye field (EF) progenitors, and retinal neural progenitor cells. The methods provided herein may use as a starting material any of the foregoing progenitor (including stem cell) populations.

The invention further contemplates generating photoreceptor cells (PRC) and photoreceptor progenitor cells (PRPC) in vitro from primary eye field (EF) progenitors and retinal neural progenitors cells (i.e., primary cells referring to cells obtained from a subject rather than from in vitro differentiation of a more immature progenitor.

Figure 22:
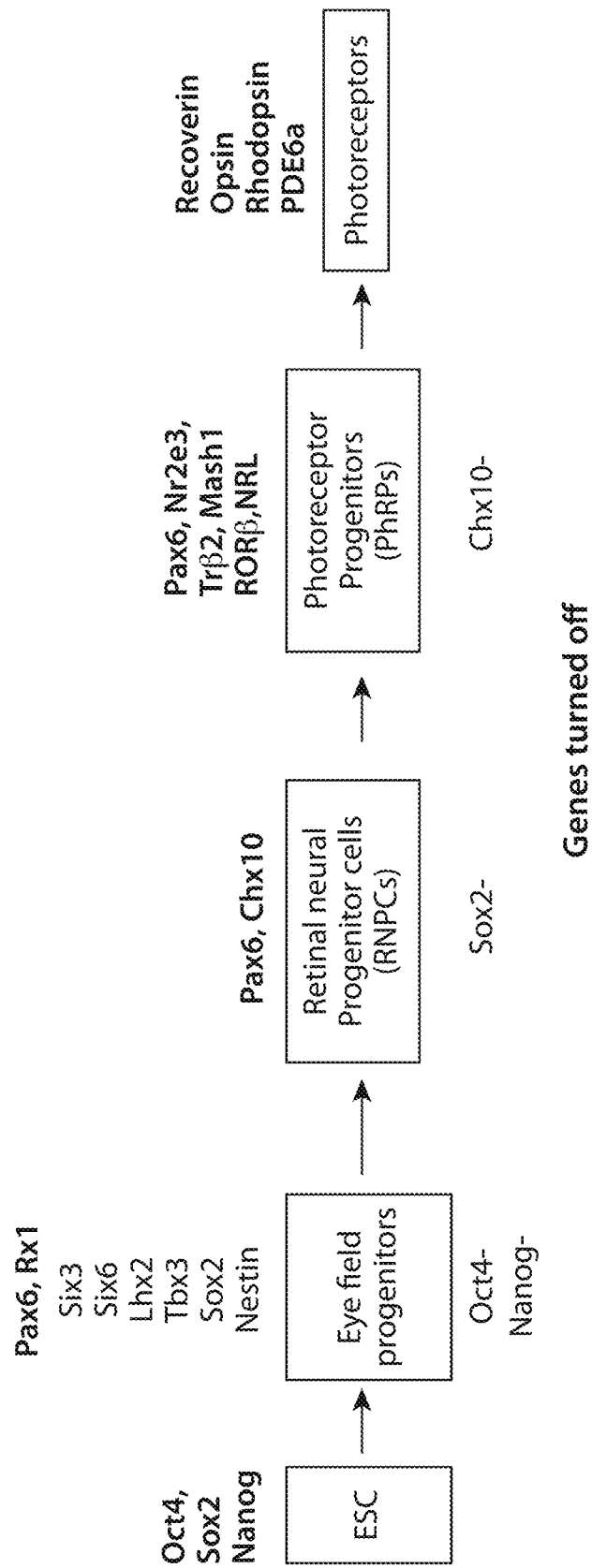
FIG. 22 illustrates the gene expression pattern of ESC, eye field progenitor cells, retinal neural progenitor cells, photoreceptor progenitor cells, and photoreceptor cells during in vitro differentiation from human pluripotent stem cells.
Figure 23:
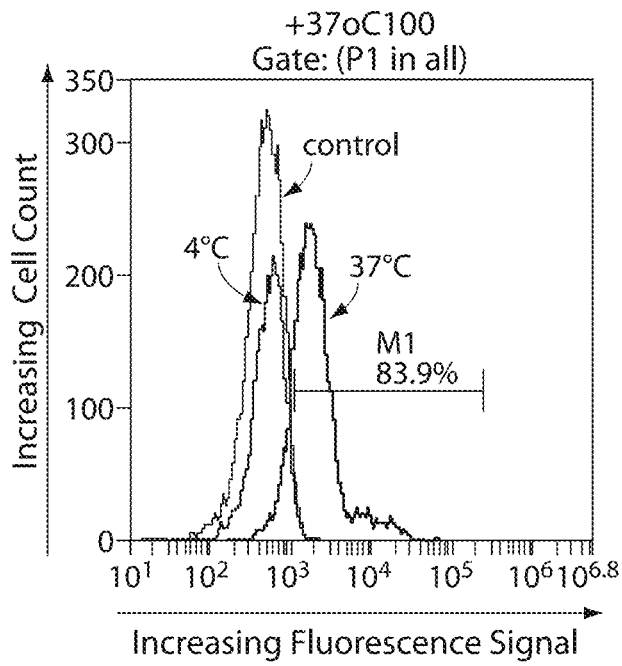
FIG. 23 provides flow cytometry histograms showing relative degrees of phagocytosis of pHrodo™ Red *E. coli* BioParticles (Invitrogen) fluorescent bioparticles by hES-RPE and hES-photoreceptor progenitors at 37° C. and at 4° C., compared to control (no bioparticles). The histogram for the photoreceptor progenitor cells illustrate that, like RPE cells, the intensity of the fluorescence signal increases upon shifting the cells from a relatively non-permissive temperature of 4° C. to a physiologically relevant temperature of 37° C., indicating that photoreceptor progenitor cells are capable of phagocytosing the bioparticles. The bioparticles are a surrogate for shed outer segments and drusen in the eye.
Figure 23:
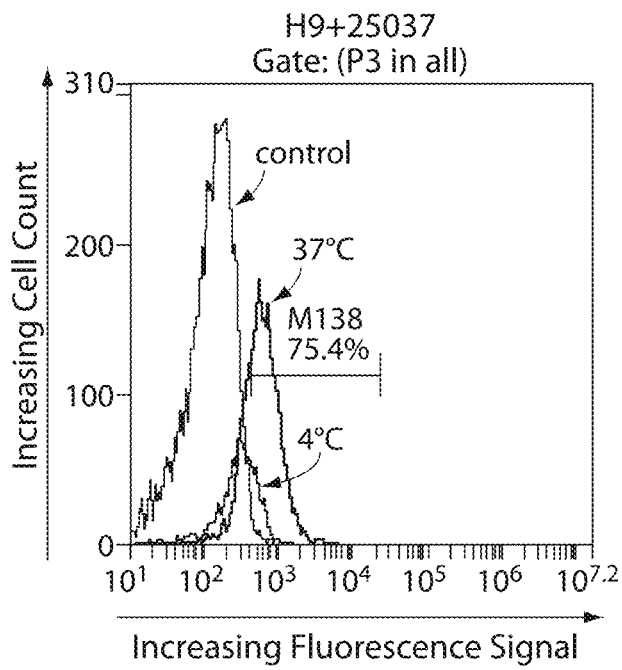
Figure 24:
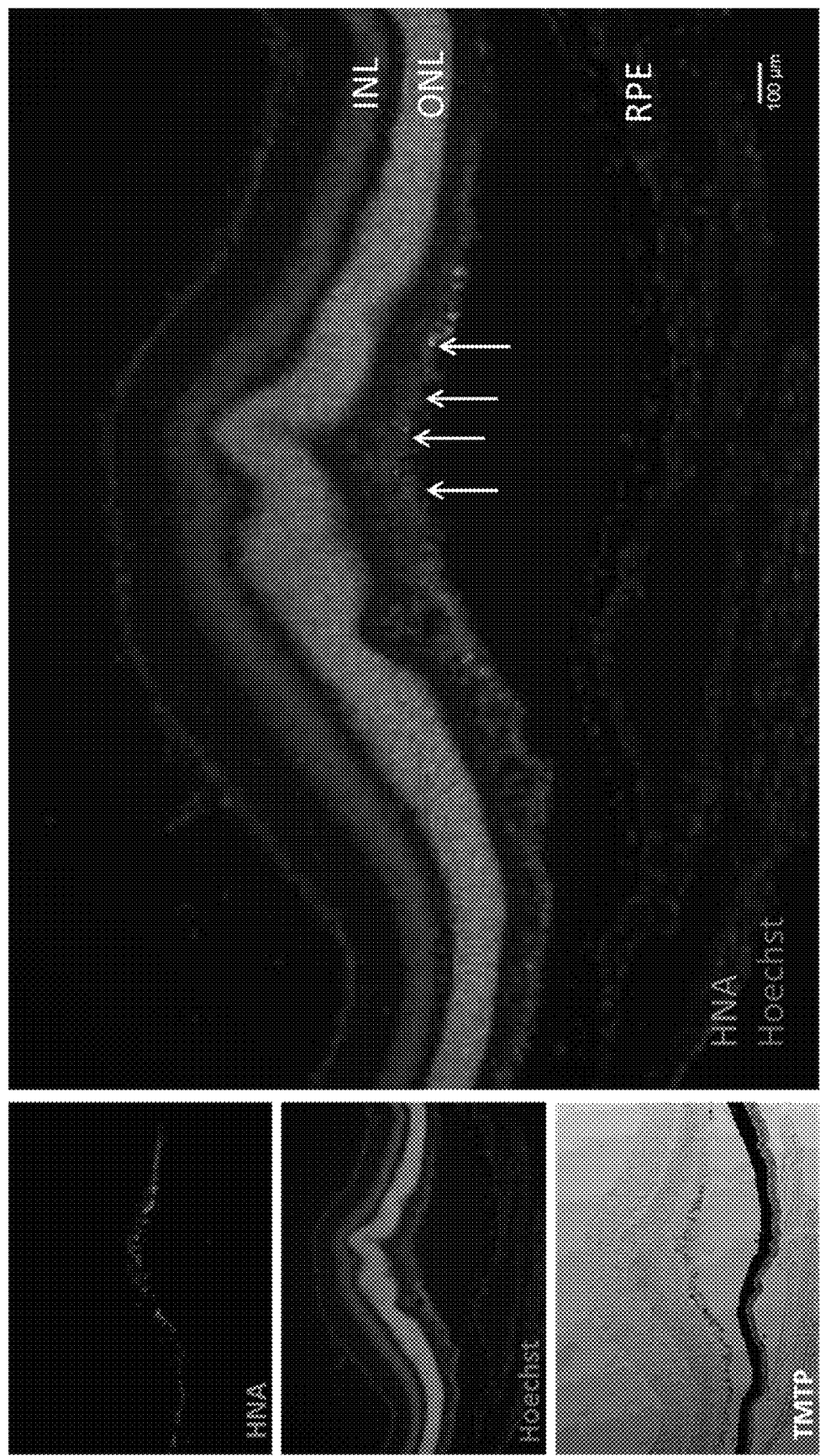
FIG. 24 provides cross-sectional images of the retina, including the INL, ONL and RPE, of wild type mice, 1 week post-transplant. The arrows indicate the presence of human cells in the subretinal space. The side panels show staining with HNA (indicative of the human donor cells) and Hoechst (indicative of DNA and thus cells generally), and a TMTP image (bright field microscopy image). HNA is human nuclear antigen, ONL is outer nuclear layer, INL is inner nuclear layer, and RPE is retinal pigment epithelium.
Figure 25:
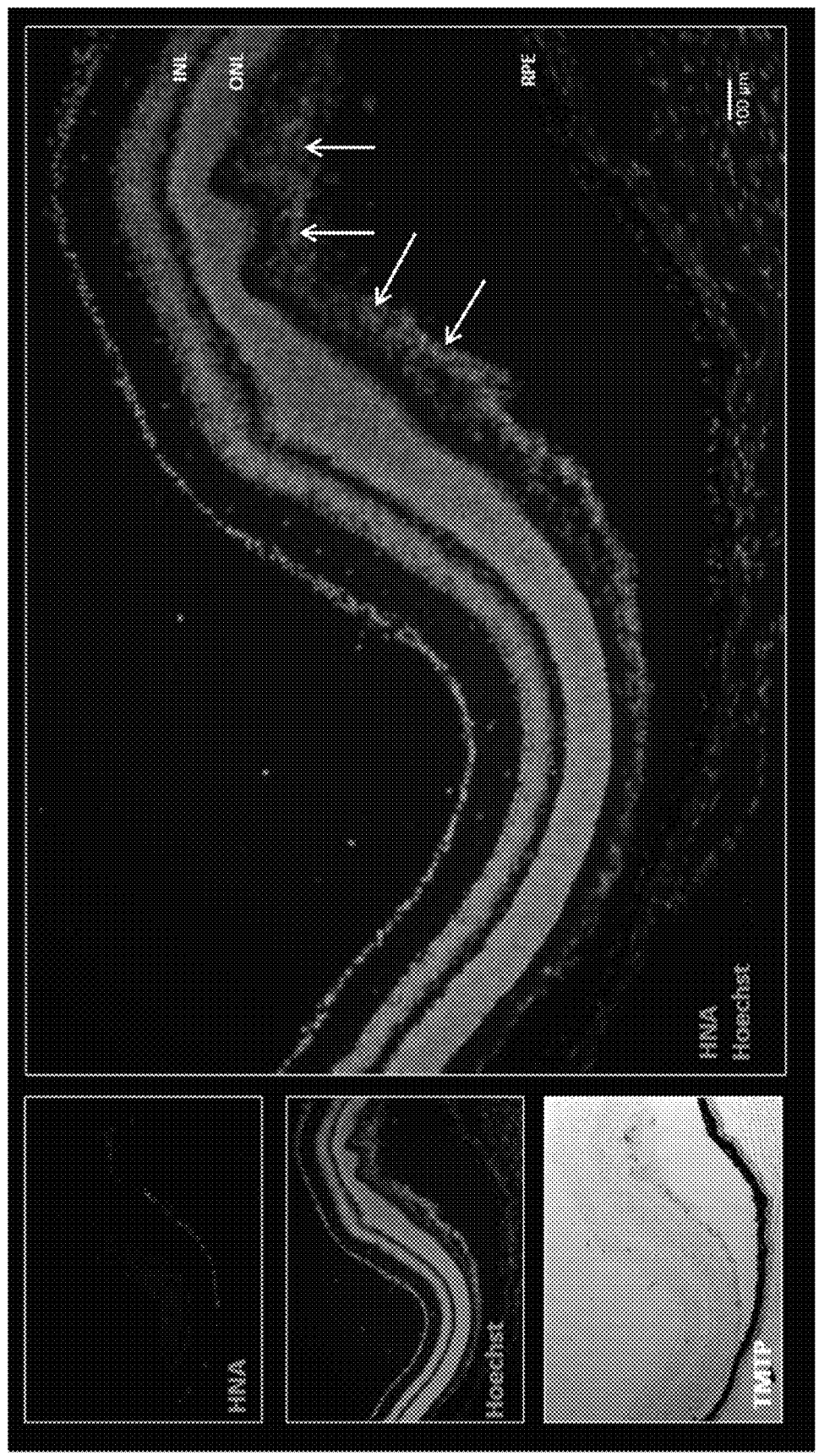
FIG. 25 provides cross-sectional images of the retina, including the INL, ONL and RPE, of wild type mice, 2 weeks post-transplant. The arrows indicate the presence of human cells in the subretinal space. The side panels show staining with HNA and Hoechst, and a TMTP image.
Figure 26:
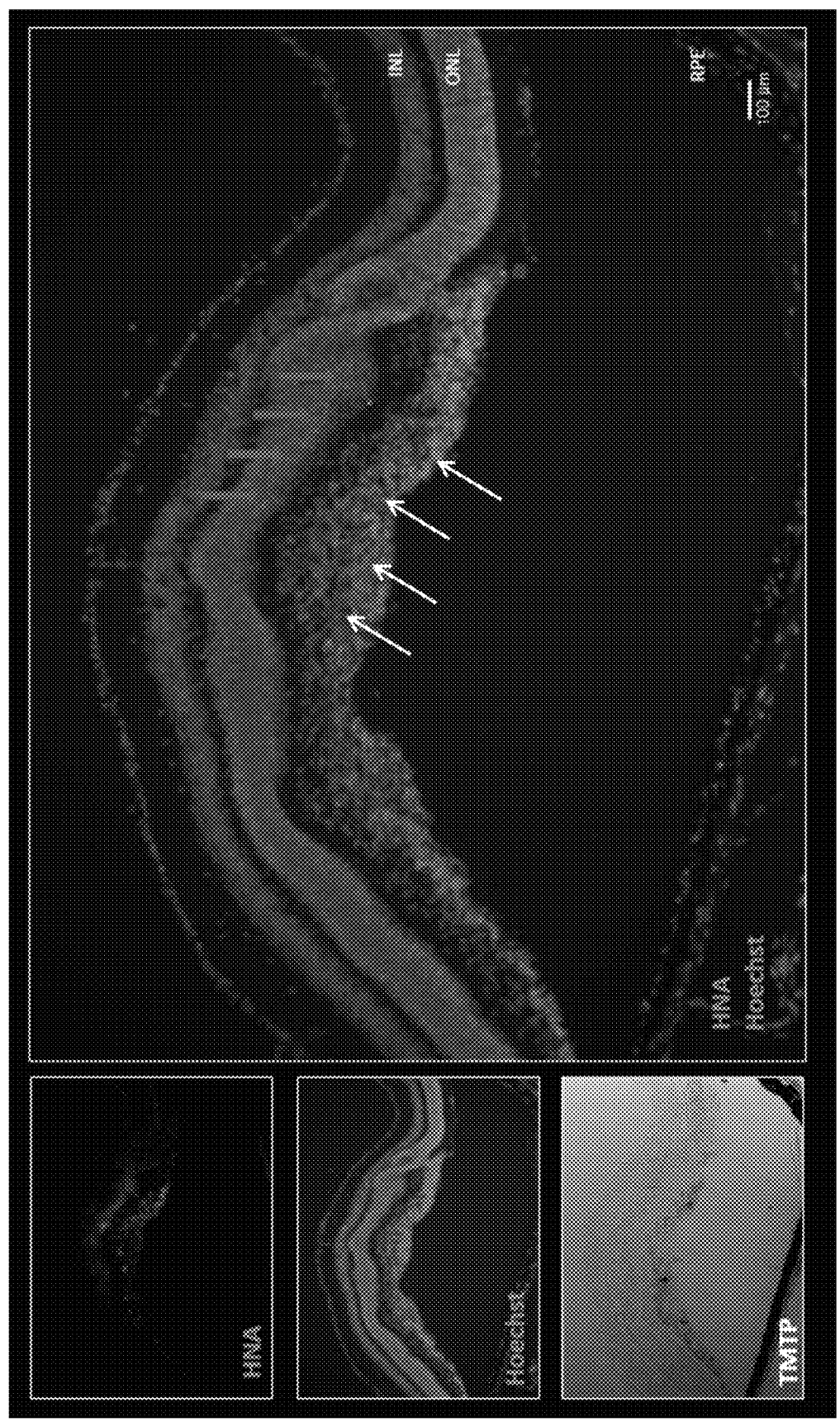
FIG. 26 provides cross-sectional images of the retina, including the INL, ONL and RPE, of wild type mice, 3 weeks post-transplant. The arrows indicate the presence of human cell in the subretinal space (bottom arrows) and the ONL (top, thicker arrows particularly). The side panels show staining with HNA and Hoechst, and a TMTP image.
Figure 27:
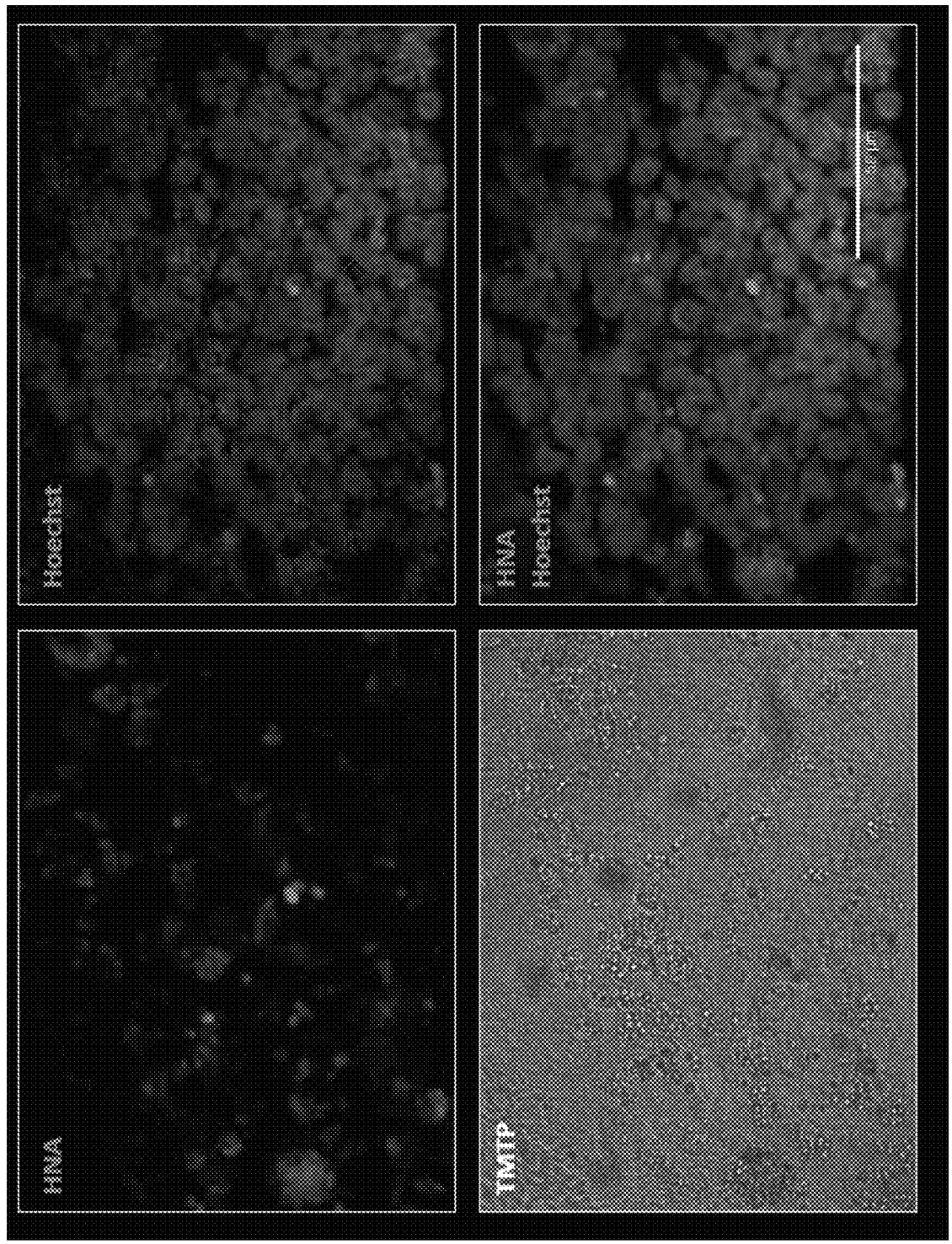
FIG. 27 provides high power cross-sectional images of transplanted cells in the outer nuclear layer (ONL). HNA is human nuclear antigen and is indicative of human donor cells and Hoechst is a DNA stain and is indicative of cells generally.

Photoreceptor development occurs through a number of developmental stages, each of which can be defined phenotypically (e.g., by way of marker expression profile) and/or functionally. This development is illustrated schematically in FIG. 22. In vitro pluripotent stem cells differentiate into EF progenitors, which in turn differentiate into retinal neural progenitor cells, which in turn differentiate into photoreceptor progenitor cells, which in turn differentiate into photoreceptor cells.

Progenitor cells, as used herein, refer to cells that remain mitotic and can produce more progenitor cells, of the same or of more limited differentiative capacity, or can differentiate to an end fate cell lineage. The terms progenitor and precursor are used interchangeably. Cells at each of these stages will be discussed in greater detail herein.

The photoreceptor progenitor cells (also referred to as photoreceptor progenitors) and photoreceptor cells provided herein may be used in a variety of in vivo and in vitro methods. For example, the photoreceptor progenitor cells may be used in vivo to treat conditions of the retina, including but not limited to macular degeneration and retinitis pigmentosa. The photoreceptor progenitor cells and photoreceptor cells may be used in vitro in screening assays to identify putative therapeutic or prophylactic treatment candidates.

The invention further provides photoreceptor progenitor cells and photoreceptor cells obtained by the methods described herein. Photoreceptor progenitor cells and photoreceptor cells obtained by in vitro differentiation of pluripotent stem cells or their differentiated progeny such as eye field progenitor cells. Eye field progenitor cells may themselves be obtained from in vitro differentiation of pluripotent stem cells, or they may be primary eye field progenitors obtained from a subject.

The invention provides populations of photoreceptor progenitor cells and populations of photoreceptor cells that have not been attained or are not attainable from primary sources. These populations may be homogenous or near homogeneous in their cell content. For example, at least 50%, at least 60%, at least 70%, at least 80%, at least 90%, at least 95%, at least 99%, or about 100% of the cells in such a population may be photoreceptor progenitor cells. As another example, at least 50%, at least 60%, at least 70%, at least 80%, at least 90%, at least 95%, at least 99%, or about 100% of the cells in such a population may be photoreceptor cells. These cells in these populations may be of a single haplotype. For example, they may be HLA-matched. These cells in these populations may be genetically identical.

The disclosure provides substantially pure (or homogeneous) preparations of various cell populations based on the ability of the disclosed methods to directly differentiate progenitor cells such as but not limited to pluripotent stem cells. As used herein, directed differentiation intends that the progenitor cell population differentiates into or towards a desired lineage, due in part to the factors or other stimuli provided to such progenitor cells, thereby avoiding differentiation into other undesired, and thus potentially contaminating, lineages. The methods provided herein drive differentiation of for example pluripotent stem cells to eye field progenitors without generating embryoid bodies (EB). EBs, as described below, are three dimensional cell clusters that can form during differentiation of pluripotent stem cells including but not limited to embryonic stem (ES) cells, and that typically contain cells, including progenitors, of mesodermal, ectodermal and endodermal lineages. The three dimensional nature of the EB may create a different environment, including different cell-cell interactions and different cell-cell signaling, than occurs in the non-EB based methods described herein. In addition, cells within EBs may not all receive a similar dose of an exogenously added agent, such as a differentiation factor present in the surrounding medium, and this can result in various differentiation events and decisions during development of the EB.

In contrast, the culture methods of the invention culture progenitor cells do not require and preferably avoid EB formation. Instead, these methods culture cells in conditions that provide the cells with equal contact with the surrounding medium, including factors in such medium. The cells may grow as a monolayer or near monolayer attached to a culture surface, as an example.

The ability of all or a majority of the progenitor cells to be in contact with their surrounding medium and thus the factors in such medium to an approximately equal degree results in those progenitor cells differentiating at similar times and to similar degrees. This similar differentiation timeline for a population of progenitor cells indicates that such cells are synchronized. The cells may be cell cycle synchronized in some instances also. Such synchronicity results in populations of cells that are homogeneous or near homogeneous in their cellular make-up. As an example, the methods described herein can produce cellular populations wherein at least 50%, at least 60%, at least 70%, at least 80%, at least 90%, at least 95%, or about 100% of cells are a particular cell of interest. The cell of interest may be defined phenotypically, for example by intracellular or extracellular marker expression. The cell of interest may be an eye field progenitor cell, a neural retinal progenitor cell, a photoreceptor progenitor cell, or a photoreceptor cell.

As used herein, a majority of cells means at least 50%, and depending on the embodiment may include at least 60%, at least 70%, at least 80%, at least 90%, at least 95%, or about 100% of cells.

The degree of purity that may be achieved using the methods of the invention are particularly important where such cell populations are to be used in vivo for therapeutic or prophylactic purposes. The ability to obtain populations of high cellular purity avoids performing another manipulation such as an enrichment or selection step, which may result in unnecessary cell loss. This is particularly important where the cell population may be small or the cell number may be limited.

Definitions

As defined here, singular forms are provided for illustrative purposes, but may also apply to plural versions of the phrase. The following definitions are meant to supplement conventional definitions of the terms as they would be understood by persons of ordinary skill.

"Substantially pure preparation of photoreceptor progenitor cells (PRPCs)." As used herein, this phrase refers to a preparation of cells (e.g., a composition comprising cells) wherein the cells are at least 75% pure or preferably at least 85% pure, at least 95% pure, or are about 85% to 95% pure. For example, the level of purity may be quantified by determining the proportion of cells in the preparation that express one or more markers, such as those markers of PRPCs (including those markers identified in this application or others known in the art), relative to the total number of cells in the preparation, e.g., by detecting cells that do or do not express said one or more markers. Optionally expression of markers indicative of non-PRPC cells may also be detected, thereby facilitating detection and/or quantitation of said cells. Exemplary methods that may be utilized to include, without limitation, Fluorescence Activated Cell Sorting (FACS), immunohistochemistry, in situ hybridization, and other suitable methods known in the art. Optionally the determination of purity may be performed disregarding non-viable cells present in the preparation.

"Substantially pure preparation of photoreceptor cells (PRs) of human origin." As used herein, this phrase refers to a preparation of cells (e.g., a composition comprising cells) wherein the cells are at least 75% pure or preferably at least 85% pure, at least 95% pure, or are about 85% to 95% pure. For example, the level of purity may be quantified by determining the proportion of cells in the preparation that express one or more markers, such as those markers of PRs (including those markers identified in this application or others known in the art), relative to the total number of cells in the preparation, e.g., by detecting cells that do or do not express said one or more markers. Optionally expression of markers indicative of non-PR cells may also be detected, thereby facilitating detection and/or quantitation of said cells. Exemplary methods that may be utilized to include, without limitation, Fluorescence Activated Cell Sorting (FACS), immunohistochemistry, in situ hybridization, and other suitable methods known in the art. Optionally the determination of purity may be performed disregarding non-viable cells present in the preparation.

"Embryoid bodies" refers to clumps or clusters of pluripotent cells (e.g., iPSC or ESC) which may be formed by culturing pluripotent cells under non-attached conditions, e.g., on a low-adherent substrate or in a "hanging drop." In these cultures, pluripotent cells can form clumps or clusters of cells denominated as embryoid bodies. See Itskovitz-Eldor et al., Mol Med. 2000 February; 6(2):88-95, which is hereby incorporated by reference in its entirety. Typically, embryoid bodies initially form as solid clumps or clusters of pluripotent cells, and over time some of the embryoid bodies come to include fluid filled cavities, the latter former being referred to in the literature as "simple" EBs and the latter as "cystic" embryoid bodies.

The term "embryonic stem cell" (ES cell or ESC) is used herein as it is used in the art. This term includes cells derived from the inner cell mass of human blastocysts or morulae, including those that have been serially passaged as cell lines. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method used to produce them, can be identified based on (i) the ability to differentiate into cells of all three germ layers, (ii) expression of at least OCT 4 and alkaline phosphatase, and (iii) ability to produce teratomas when transplanted into immunodeficient animals. Embryonic stem cells that may be used in embodiments of the present invention include, but are not limited to, human ES cells ("ESC" or "hES cells") such as MA01, MA09, ACT-4, No. 3, H1, H7, H9, H14 and ACT30 embryonic stem cells. Additional exemplary cell lines include NED1, NED2, NED3, NED4, NED5, and NED7. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444: 481-485. The human ES cells used in accordance with exemplary embodiments of the present invention may be derived and maintained in accordance with GMP standards.

The term "ES cells" does not infer, and should not be inferred to mean, that the cells were generated through the destruction of an embryo. To the contrary, various methods are available and can be used to generate ES cells without destruction of an embryo, such as a human embryo. As an example, ES cells may be generated from single blastomeres derived from an embryo, in a manner similar to the extraction of blastomeres for pre-implantation genetic diagnosis (PGD). Examples of such cell lines include NED1, NED2, NED3, NED4, NED5, and NED7. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444: 481-485. See also Chung et al. 2008, Cell Stem Cell, 2:113. All of these lines were generated without embryo destruction.

As used herein, the term "pluripotent stem cells" includes but is not limited to tissue-derived stem cells, embryonic stem cells, embryo-derived stem cells, induced pluripotent stem cells, and stimulus-triggered acquisition of pluripotency (STAP) cells, regardless of the method by which the pluripotent stem cells are derived. The term also includes pluripotent stem cells having the functional and phenotypic characteristics of the afore-mentioned cells, regardless of the method used to generate such cells. Pluripotent stem cells are defined functionally as stem cells that are: (a) capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express OCT4, alkaline phosphatase, SSEA-3 surface antigen, SSEA-4 surface antigen, Nanog, TRA-1-60, TRA-1-81, SOX2, REX1, etc.). In certain embodiments, pluripotent stem cells express one or more markers selected from the group consisting of: OCT4, alkaline phosphatase, SSEA-3, SSEA-4, TRA-1-60, and TRA-1-81. Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPSCs) generated by reprogramming a somatic cell by expressing a combination of factors (herein referred to as reprogramming factors). The iPSCs can be generated using fetal, postnatal, newborn, juvenile, or adult somatic cells.

In certain embodiments, factors that can be used to reprogram somatic cells to pluripotent stem cells include, for example, a combination of OCT 4 (sometimes referred to as OCT 3/4), SOX2, c-Myc, and KLF4. In other embodiments, factors that can be used to reprogram somatic cells to pluripotent stem cells include, for example, a combination of OCT 4, SOX2, Nanog, and Lin28. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell. In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc.). Pluripotent stem cells may be genetically modified or otherwise modified to increase longevity, potency, homing, to prevent or reduce alloimmune responses or to deliver a desired factor in cells that are differentiated from such pluripotent cells (for example, photoreceptors, photoreceptor progenitor cells, rods, cones, etc. and other cell types described herein, e.g., in the examples).

"Induced pluripotent stem cells" (iPS cells or iPSC) can be produced by protein transduction of reprogramming factors in a somatic cell. In certain embodiments, at least two reprogramming proteins are transduced into a somatic cell to successfully reprogram the somatic cell. In other embodiments, at least three reprogramming proteins are transduced into a somatic cell to successfully reprogram the somatic cell. In other embodiments, at least four reprogramming proteins are transduced into a somatic cell to successfully reprogram the somatic cell.

The pluripotent stem cells can be from any species. Embryonic stem cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc.), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPS cells can be from any species. These iPS cells have been successfully generated using mouse and human cells. Furthermore, iPS cells have been successfully generated using embryonic, fetal, newborn, and adult tissue. Accordingly, one can readily generate iPS cells using a donor cell from any species. Thus, one can generate iPS cells from any species, including but not limited to, human, non-human primates, rodents (mice, rats), ungulates (cows, sheep, etc.), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

The induced pluripotent stem cell may be produced by expressing or inducing the expression of one or more reprogramming factors in a somatic cell. The somatic cell may be a fibroblast, such as a dermal fibroblast, synovial fibroblast, or lung fibroblast, or a non-fibroblastic somatic cell. The somatic cell may be reprogrammed through causing expression of (such as through viral transduction, integrating or non-integrating vectors, etc.) and/or contact with (e.g., using protein transduction domains, electroporation, microinjection, cationic amphiphiles, fusion with lipid bilayers containing, detergent permeabilization, etc.) at least 1, 2, 3, 4, 5 reprogramming factors. The reprogramming factors may be selected from OCT 3/4, SOX2, NANOG, LIN28, C-MYC, and KLF4. Expression of the reprogramming factors may be induced by contacting the somatic cells with at least one agent, such as a small organic molecule agents, that induce expression of reprogramming factors.

Further exemplary pluripotent stem cells include induced pluripotent stem cells generated by reprogramming a somatic cell by expressing or inducing expression of a combination of factors ("reprogramming factors"). iPS cells may be obtained from a cell bank. The making of iPS cells may be an initial step in the production of differentiated cells. iPS cells may be specifically generated using material from a particular patient or matched donor with the goal of generating tissue-matched PHRPS or photoreceptor cells. iPSCs can be produced from cells that are not substantially immunogenic in an intended recipient, e.g., produced from autologous cells or from cells histocompatible to an intended recipient.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. See, e.g., Yu et al., Science. 2009 May 8; 324(5928):797-801, which is hereby incorporated by reference in its entirety. When reprogramming factors are expressed using non-integrative vectors, the factors may be expressed in the cells using electroporation, transfection, or transformation of the somatic cells with the vectors. For example, in mouse cells, expression of four factors (OCT3/4, SOX2, C-MYC, and KLF4) using integrative viral vectors is sufficient to reprogram a somatic cell. In human cells, expression of four factors (OCT3/4, SOX2, NANOG, and LIN28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPSC is obtained it may be used to produce cell types disclosed herein, e.g., photoreceptor progenitor cells, photoreceptor cells, rods, cones, etc. and other cell types described herein, e.g., in the examples.

Stimulus-triggered acquisition of pluripotency (STAP) cells are pluripotent stem cells produced by reprogramming somatic cells with sublethal stimuli such as low-pH exposure. The reprogramming does not require nuclear transfer into or genetic manipulation of the somatic cells. Reference can be made to Obokata et al., Nature, 505:676-680, 2014.

"Stem cell" is used here to refer to a pluripotent cell which can proliferate and/or differentiate into a mature cell and is optionally of human origin.

"Adult stem cell" refers to a multipotent cell isolated from adult tissue and can include bone marrow stem cells, cord blood stem cells and adipose stem cells and is of human origin.

"Retina" refers to the neural cells of the eye, which are layered into three nuclear layers comprised of photoreceptors, horizontal cells, bipolar cells, amacrine cells, Müller glial cells and ganglion cells.

"Precursor cell" refers to a cell capable of differentiating to an end fate cell lineage. In embodiments of the invention, an "eye field progenitor cell" is differentiated from embryonic stem cells or induced pluripotent stem cells and expresses the markers PAX6 and RX1. In embodiments of the invention, a "retinal neural progenitor cell" refers to a cell differentiated from embryonic stem cells or induced pluripotent stem cells, that expresses the cell markers PAX6 and CHX10. In embodiments of the invention, "photoreceptor progenitor" refers to cells differentiated from embryonic stem cells or induced pluripotent stem cells and that expresses the marker PAX6 while not expressing the marker CHX10 (i.e. CHX10(−)). These cells transiently express CHX10 at retinal neural progenitor stage, but the CHX10 expression is turned off when cells differentiate into the photoreceptor progenitor stage. Also, "photoreceptor" may refer to post-mitotic cells differentiated from embryonic stem cells or induced pluripotent stem cells and that expresses the cell marker rhodopsin or any of the three cone opsins, and optionally express the rod or cone cGMP phosphodiesterase. The photoreceptors may also express the marker recoverin, which is found in photoreceptors. The photoreceptors may be rod and/or cone photoreceptors.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," "treat" or "treatment", as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms. Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms. Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms.

Conditions to be treated according to the invention and thus using one or more of the preparations provided herein include but are not limited macular degeneration including age-related macular degeneration, and such macular degeneration may be early or late stage. Other conditions to be treated include but are not limited to retinitis pigmentosa, retinal dysplasia, retinal degeneration, diabetic retinopathy, congenital retinal dystrophy, rod dystrophy, cone dystrophy, cone-rod dystrophy, Leber congenital amaurosis, retinal detachment, glaucoma, optic neuropathy, and trauma that affects the eye.

Cell Markers:

Exemplary cell markers that may be assessed for expression include the following: PAX6, RX1, SIX3, SIX6, LHX2, TBX3, SOX2, CHX10, Nestin, TRbeta2, NR2E3, NRL, MASH1, RORbeta, Recoverin, Opsin, Rhodopsin, rod and cone cGMP Phosphodiesterase, which may be assessed at the protein and/or mRNA (see Fischer A J, Reh T A, Dev Neurosci. 2001; 23(4-5):268-76; Baumer et al., Development. 2003 July; 130(13):2903-15, Swaroop et al., Nat Rev Neurosci. 2010 August; 11(8):563-76, Agathocleous and Harris, Annu. Rev. Cell Dev. Biol. 2009. 25:45-69, each of which is hereby incorporated by reference in its entirety). Said marker identifiers are generally used as in the literature and in the art, particular in the fields of art in related to the contexts in which those gene identifiers are recited herein, which may include literature related to photoreceptors, rods, cones, photoreceptor differentiation, photoreceptor progenitors, neural differentiation, neural stem cells, pluripotent stem cells, and other fields as indicated by context. Additionally, the markers are generally human, e.g., except where the context indicates otherwise. The cell markers can be identified using conventional immunocytochemical methods or conventional PCR methods which techniques are well known to those of ordinary skill in the art.

Cell Culture Media:

In embodiments of the invention, the cells are stored, proliferated or differentiated in various cell culture media. Retinal induction medium is utilized for the stem cell production into Eye Field Progenitor Cells. The retinal induction medium may comprise D-glucose, penicillin, streptomycin, N2 supplement (e.g. 0.1-5%), B27 supplement (e.g., 0.005 to 0.2%), MEM non-essential amino acids solution and optionally including insulin and/or Noggin, and may be in a DMEM/F12 (Invitrogen) or similar base medium. For example, the Retinal induction medium may include at least insulin. Additionally, the insulin concentration may be varied or increased which may promote cell survival and/or yield of differentiated cells. For example, the insulin concentration may be varied across a range and survival and/or differentiation monitored in order to identify an insulin concentration with improves either or both of these attributes. The addition of Noggin is believed not to be necessary but was observed to increase the expression of eye field transcription factors.

The components of DMEM/F12, Neurobasal medium, N2 serum supplement, and B27 serum supplement are provided in FIG. 21. It is to be understood that the invention contemplates the use of these particular media and supplements or media or supplements comprising, consisting essentially of, or consisting of these components.

The methods described herein may use human factors such as human Noggin, human insulin, and the like.

Noggin is a secreted bone morphogenetic protein (BMP) inhibitor that reportedly binds BMP2, BMP4, and BMP7 with high affinity to block TGFβ family activity. SB431542 is a small molecule that reportedly inhibits TGFβ/Activin/Nodal by blocking phosphorylation of ACTRIB, TGFβR1, and ACTRIC receptors. SB431542 is thought to destabilize the Activin- and Nanog-mediated pluripotency network as well as suppress BMP induced trophoblast, mesoderm, and endodermal cell fates by blocking endogenous Activin and BMP signals. It is expected that agents having one or more of the aforementioned activities could replace or augment the functions of one or both of Noggin and SB431542, e.g., as they are used in the context of the disclosed methods. For example, applicants envision that the protein Noggin and/or the small molecule SB4312542 could be replaced or augmented by one or more inhibitors that affect any or all of the following three target areas: 1) preventing the binding of the ligand to the receptor; 2) blocking activation of receptor (e.g., dorsomorphin), and 3) inhibition of SMAD intracellular proteins/transcription factors. Exemplary potentially suitable factors include the natural secreted BMP inhibitors Chordin (which blocks BMP4) and Follistatin (which blocks Activin), as well as analogs or mimetics thereof. Additional exemplary factors that may mimic the effect of Noggin include use of dominant negative receptors or blocking antibodies that would sequester BMP2, BMP4, and/or BMP7. Additionally, with respect to blocking receptor phosphorylation, dorsomorphin (or Compound C) has been reported to have similar effects on stem cells. Inhibition of SMAD proteins may also be effected using soluble inhibitors such as SIS3 (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline, Specific Inhibitor of Smad3, SIS3), overexpression of one or more of the inhibitor SMADs (e.g., SMAD6, SMAD7, SMAD10) or RNAi for one of the receptor SMADs (SMAD1, SMAD2, SMAD3, SMAD5, SMAD8/9). Another combination of factors expected to be suitable for generating neural progenitors comprises a cocktail of Leukemia Inhibitory Factor (LIF), GSK3 inhibitor (CHIR 99021), Compound E (γ secretase inhibitor XXI) and the TGFβ inhibitor SB431542 which has been previously shown to be efficacious for generating neural crest stem cells (Li et al., Proc Natl Acad Sci USA. 2011 May 17; 108(20):8299-304). Additional exemplary factors may include derivatives of SB431542, e.g., molecules that include one or more added or different substituents, analogous functional groups, etc. and that have a similar inhibitory effect on one or more SMAD proteins. Suitable factors or combinations of factors may be identified, for example, by contacting pluripotent cells with said factor(s) and monitoring for adoption of eye field progenitor cell phenotypes, such as characteristic gene expression (including expression of the markers described herein, expression of a reporter gene coupled to an eye field progenitor cell promoter, or the like) or the ability to form a cell type disclosed herein such as retinal neural progenitor cells, photoreceptor progenitors, rod progenitors, cones, and/or rods.

Preferably the cells are treated with or cultured in a retinal induction medium prior to culture with a neural differentiation medium. A neural differentiation medium is utilized for Eye Field Progenitor Cell production into Retinal Neural Progenitor Cells. The neural differentiation medium may comprise D-glucose, penicillin, streptomycin, GlutaMAX™, N2 supplement, B27 supplement, MEM non-essential amino acids solution and optionally including Noggin. The neural differentiation medium may also be utilized for Retinal Neural Progenitor Cell production into Photoreceptor Progenitor Cells but without the inclusion of Noggin. The use of a neural differentiation medium, optionally supplemented with retinoic acid and taurine, followed by utilization of a photoreceptor differentiation medium (Invitrogen) which optionally may comprise D-glucose, penicillin, streptomycin, GlutaMAX™, N2 supplement, B27 supplement (e.g., formula number 080085-SA) with the addition of forskolin, BDNF, CNTF, LIF and DAPT is utilized for Photoreceptor Progenitor Cells production into Photoreceptor Cells. For example the photoreceptor differentiation medium may comprise thyroid hormone, e.g., in an amount that is present in the foregoing medium, or in a different or greater amount. For example said medium may comprise exogenously added thyroid hormone. In exemplary embodiments the photoreceptor differentiation medium may comprise one, two, or all three BDNF, CNTF and DAPT, e.g., BDNF, CNTF, DAPT, BDNF and CNTF, CNTF and DAPT, BDNF and DAPT, or all three of BDNF, CNTF and DAPT, which medium may optionally comprise Neurobasal Medium and/or may optionally comprise thyroid hormone.

The neural differentiation medium constituents are as follows: N2: 1% (1 ml of N2 per 100 ml), B27: 2% (2 ml of B27 per 100 ml), and Noggin: 50 ng/ml.

Noggin is not needed after cells have all become eye field progenitors.

Embryonic Stem Cells (ESCs) or Adult Stem Cells or Induced Pluripotent Stem Cells (iPS):

The ESCs, or Adult Stem Cells or iPS cells utilized herein may be propagated on a feeder-free system, such as in Matrigel™ (a soluble preparation from Engelbreth-Holm-Swarm (EHS) mouse sarcoma cells) or another matrix. Additionally, or alternatively, said pluripotent cells may be cultured on a matrix which may be selected from the group consisting of laminin, fibronectin, vitronectin, proteoglycan, entactin, collagen, collagen I, collagen IV, collagen VIII, heparan sulfate, Matrigel™ (a soluble preparation from Engelbreth-Holm-Swarm (EHS) mouse sarcoma cells), CellStart, a human basement membrane extract, and any combination thereof. Said matrix may comprise, consist of, or consist essentially of Matrigel™ (a soluble preparation from Engelbreth-Holm-Swarm (EHS) mouse sarcoma cells). The stem cells do not form embryoid bodies in culture, which is an improvement over the prior art. The cells differentiate into eye field progenitor cells in the absence of exogenous factors. In an embodiment, ESCs differentiate into eye field progenitor cells in the presence of Noggin.

Eye Field Progenitor Cells (EFPCs):

The EFPCs differentiate from ESCs, Adult stem cells or induced pluripotent stem cells (iPSCs) into cells that are PAX6(+) and RX1(+). The EFPCs can also be SIX3(+), SIX6(+), LHX2(+), TBX3(+) Nestin(+) and/or SOX2(+) and OCT4(−) and NANOG(−). The differentiation into EFPCs occurs in a retinal induction medium which may comprise DMEM/F12, D-glucose, penicillin, streptomycin, N2 supplement, B27 supplement, MEM non-essential amino acid and insulin. On day 5, when cells reach confluence, cells are changed to neural differentiation medium. Preferably the step of producing EFPCs is performed prior to culturing pluripotent cells in the neural differentiation medium described below, as it has been observed that such culture conditions may adversely affect pluripotent cell viability.

Retinal Neural Progenitor Cells (RNPCs):

The RNPCs differentiate from the EFPCs in the absence of exogenous factors. The RNPCs are PAX6(+) and CHX10(+). The cells at this state may be Tuj1+ or Tuj1−. Optionally the method may include enriching or purifying Tuj1+ or Tuj1− cells at this stage, and/or purifying or removing strongly Tuj1+ cells and/or purifying or removing strongly Tuj1− cells (e.g., cells lacking even low level detectable expression thereof) and proceeding with the subsequent method steps with one or the other of these populations. In an embodiment, Noggin is added to accelerate the differentiation from EFPCs to RNPCs The differentiation into RNPCs occurs in a neural differentiation media which may comprise Neurobasal Medium (Invitrogen), D-glucose, penicillin, streptomycin, GlutaMAX™, N2 supplement, B27 supplement and MEM non-essential amino acid solution. Noggin may be added at a final concentration of 5-100 µg/ml.

Photoreceptor Progenitor Cells (PhRPCs):

The PhRPCs may be differentiated from the RNPCs in the absence of Noggin and in neural differentiation medium). The PRPCs are PAX6(+) and CHX10(−). In embodiment, 60%, 70%, 80%, 85%, 90%, or 95% of the PRPCs are PAX6(+) and CHX10(−) The PRPCs can also be Nr2e3(+), Trβ2(+), Mash1(+), RORβ(+) and/or NRL(+). The presence of CHX10 would suggest a bipolar cell lineage, but in the present method, the PRPCs have differentiated to a photoreceptor lineage, and therefore do not possess CHX10 at this stage. The cells may be grown as spheres or neurospheres (e.g., on low attachment plates or optionally on hanging drop cultures, in a low-gravity environment, or other suitable culture condition).

Photoreceptors (PRs):

The PRs may differentiate from the PhRPCs in a two-step differentiation process 1) Adding neural differentiation medium with retinoic acid and taurine for 2 weeks and 2) addition of the photoreceptor differentiation medium.—see Example 2.

The PRs may be rhodopsin(+), recoverin(+), PE6a(+) or opsin(+). The opsin may be any of the cone opsins. The PRs may be bipotential for cones or rods. Exemplary photoreceptors produced by this method may be PAX6−, which may be in contrast to some previously described purported photoreceptor cells. As described below in exemplary embodiments there is a 2 step differentiation process 1) adding ND medium and retinoic acid and taurine for 2 weeks and 2) use of the photoreceptor differentiation medium, which methods are further exemplified in the working examples below.

In exemplary embodiments the method may produce 40-60 million EFPCs, 60-90 million RNPCs, or 0.5-1 billion PhRPCs per starting 1 million pluripotent cells.

In an exemplary embodiment, the cells may be transplanted into a rat in need thereof, e.g., an RCS rat, or other animal model of disease (e.g. for night blindness or for color blindness), and the resulting effect on visual function may be detected by the optomotor response test, ERG, luminance threshold recording and/or the visual center blood flow assay.

In certain embodiments, the photoreceptor progenitors and/or photoreceptors derived therefrom, have at least a two-fold increase in transcription and/or expression of one or more proteins selected from Chrna7, Edil3, CD59a, Hpse, Akt3 and Cast when compared to the average of photoreceptors from healthy human adults.

In certain embodiments, the photoreceptor progenitors and/or photoreceptors derived therefrom, have at least a two-fold decrease in transcription and/or expression of one or more proteins selected from Acvrl1, Cxcl12, Dnmt3a, Tef, Neurl1, Ncor1, Cxcl12 and Rhoa when compared to the average of photoreceptors from healthy human adults.

Applications and Uses

Screening Assays

The present invention provides methods for screening various agents that modulate the differentiation of a retinal progenitor cell. It could also be used to discover therapeutic agents that support and/or rescue mature photoreceptors that are generated in culture from retinal progenitor cells. For the purposes of this invention, an "agent" is intended to include, but not be limited to, a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated, that the agent is used alone or in combination with another agent, having the same or different biological activity as the agents identified by the inventive screen.

To practice the screening method in vitro, an isolated population of cells can be obtained as described herein. When the agent is a composition other than a DNA or RNA, such as a small molecule as described above, the agent can be directly added to the cells or added to culture medium for addition. As is apparent to those skilled in the art, an "effective" amount must be added which can be empirically determined. When the agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

Neurosensory Retinal Structures

The photoreceptor progenitor cells, and optionally the photoreceptor cells differentiated therefrom, can be used to generate neurosensory retinal structures. For instance, the invention contemplates the generation of multilayer cellular structures comprised of retinal pigment epithelial (RPE) cells and photoreceptor cells (or photoreceptor progenitor cells). These structures can be used for drug screening, as models for diseases, or as or in a pharmaceutical preparation. In the latter case, the pharmaceutical preparation can be an RPE-photoreceptor graft, which may be disposed on a biocompatible solid support or matrix (preferably a bioresorbable matrix or support) that can be implanted like a "patch".

To further illustrate, the biocompatible support for the cells can be a biodegradable polyester film support for retinal progenitor cells. The biodegradable polyester can be any biodegradable polyester suitable for use as a substrate or scaffold for supporting the proliferation and differentiation of retinal progenitor cells. The polyester should be capable of forming a thin film, preferably a micro-textured film, and should be biodegradable if used for tissue or cell transplantation. Suitable biodegradable polyesters for use in the invention include polylactic acid (PLA), polylactides, polyhydroxyalkanoates, both homopolymers and co-polymers, such as polyhydoxybutyrate (PHB), polyhydroxybutyrate co-hydroxyvalerate (PHBV), polyhydroxybutyrate co-hydroxyhexanote (PHBHx), polyhydroxybutyrate co-hydroxyoctonoate (PHBO) and polyhydroxybutyrate co-hydroxyoctadecanoate (PHBOd), polycaprolactone (PCL), polyesteramide (PEA), aliphatic copolyesters, such as polybutylene succinate (PBS) and polybutylene succinate/adipate (PBSA), aromatic copolyesters. Both high and low molecular weight polyesters, substituted and unsubstituted polyester, block, branched or random, and polyester mixtures and blends can be used. Preferably the biodegradable polyester is polycaprolactone (PCL).

In certain embodiments, the biocompatible support is a poly(p-xylylene) polymer, such as parylene N, parylene D, parylene-C, parylene AF-4, parylene SF, parylene HT, parylene VT-4 and Parylene CF, and most preferably parylene-C.

The polymeric support can typically be formed into a thin film using known techniques. The film thickness is advantageously from about 1 micron to about 50 microns, and preferably about 5 microns in thickness. The surface of the film can be smooth, or the film surface can be partially or completely micro-textured. Suitable surface textures include micro-grooves or micro-posts, for instance. The film can be cut and shaped to form a suitable shape for implantation.

The RPE and/or photoreceptor cells or photoreceptor progenitor cells can be plated directly—together or sequentially (e.g., photoreceptor cells or photoreceptor progenitor cells after an RPE layer is formed)—onto the film to form a biocompatible scaffold. Alternatively, the polymer film can be coated with a suitable coating material such as poly-D-lysine, poly-L-lysine, fibronectin, laminin, collagen I, collagen IV, vitronectin and Matrigel™. The cells can be plated to any desired density, but a single layer of RPE cells (an RPE monolayer) is preferred.

Alternatively, the photoreceptors and/or photoreceptor progenitors may be administered together with other cell types, including other retinal cell types such as but not limited to retinal ganglion cells, retinal ganglion progenitor cells, retinal pigment epithelium (RPE) cells or RPE progenitors. The photoreceptors and/or photoreceptor progenitors may be administered with one or any combination of these different cell types. The cells may be administered on a matrix or scaffold, as described above, or they may be administered as cell aggregates, or they may be administered as a dissociated cell suspension. In some embodiments, the cells may be administered on top of a monolayer of RPE cells, which itself may or may not be situated on a matrix or substrate. The cells to be administered may all be derived from in vitro differentiation of hES cells or iPS cells or in some instances they may derive or be obtained from other sources. Certain cells may be derived from in vitro differentiation of hES cells or iPS cells and other cells may derive or be obtained from other sources. At a minimum, the photoreceptor cells and/or photoreceptor progenitor cells are derived from in vitro differentiation of pluripotent stem cells such as hES cells or iPS cells. Any of these various cell combinations may be administered conjointly with other therapeutic agents such as those described herein.

Therapeutic Uses

This invention also provides methods for replacing or repairing photoreceptor cells in a patient in need of this treatment comprising administering a pharmaceutical preparation including the photoreceptor progenitor cells of the present invention, or photoreceptors derived therefrom or a combination thereof, to a patient. As described herein, the pharmaceutical preparation can be a suspension of cells or cells which are formed into transplantable tissue in vitro. In many instances, the cells will be administered to the subretinal space of a diseased or degenerated retina. However, as the photoreceptor progenitor cells of the present invention also have a neuroprotective effect, the cells can be administered locally but outside of the retina (such as in the vitreous) or by depot or systemic delivery to other parts of the body.

The pharmaceutical preparations of the present invention can be used in a wide range of diseases and disorders that result in visual system deterioration, including retinal degeneration-related disease. Such diseases and disorders may be caused by aging, such that there appears to be an absence of an injury or disease that is identifiable as a substantial source of the deterioration. Skilled artisans will understand the established methods for diagnosing such disease states, and/or inspecting for known signs of such injuries. In addition, the literature is replete with information on age-related decline or deterioration in aspects of the visual systems of animals. The term "retinal degeneration-related disease" is intended to refer to any disease resulting from innate or postnatal retinal degeneration or abnormalities. Examples of retinal degeneration-related diseases include retinal dysplasia, retinal degeneration, aged macular degeneration, diabetic retinopathy, retinitis pigmentosa, congenital retinal dystrophy, Leber congenital amaurosis, retinal detachment, glaucoma, optic neuropathy, and trauma.

Additionally or alternatively, the deterioration of the visual system components, such as the neurosensory retina can be caused by injury, for example trauma to the visual system itself (e.g., an eye), to the head or brain, or the body more generally. Certain such injuries are known to be age-related injuries, i.e., their likelihood, or frequency increases with age. Examples of such injuries include retinal tears, macular holes, epiretinal membrane, and retinal detachments, each of which might occur in an animal of any age, but which are more likely to occur, or occur with greater frequency in aging animals, including otherwise healthy aging animals.

The deterioration of the visual system or components thereof also can be caused by disease. Included among the diseases are various age-related diseases that impact the visual system. Such diseases occur with greater likelihood and/or frequency in older animals than in the young. Examples of diseases which may affect the visual system, including for example the neurosensory retinal layers, and cause deterioration thereof are various forms of retinitis, optic neuritis, macular degeneration, proliferative or non-proliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage (preretinal, intraretinal and/or subretinal), hypertensive retinopathy, retinal inflammation, retinal edema, retinoblastoma, or retinitis pigmentosa.

Some of the foregoing diseases tend to be specific to certain animals such as companion animals, e.g., dogs and/or cats. Some of the diseases are listed generically, i.e., there may be many types of retinitis, or retinal hemorrhage; thus some of the disease are not caused by one specific etiologic agent, but are more descriptive of the type of disease or the result. Many of the diseases that can cause decline or deterioration of one or more components of the visual system can have both primary and secondary or more remote effects on an animal's visual system.

Advantageously, the pharmaceutical preparations of the present invention may be used to compensate for a lack or diminution of photoreceptor cell function. As illustrated in the Examples, the cells of the invention, including the photoreceptor progenitors, can be used as a cell replacement therapy in subjects that have lost photoreceptor function, in whole or in part. Such subjects if human may have eyesight characterized as 20/60 or worse, including 20/80 or worse, or 20/100 or worse, or 20/120 or worse, or 20/140 or worse, or 20/160 or worse, or 20/180 or worse, or 20/200 or worse. Thus, this disclosure contemplates treatment of subjects having some level of visual acuity as well as those having no discernable visual acuity.

The cells of this disclosure may be characterized by their ability to reconstitute some level of visual acuity in animal models such as mouse models. In some instances, suitable animal models may be those having a visual impairment that manifests as an optomotor response that is 10% or less, 20% or less, 30% or less, 40% or less, or 50% or less than wild type response. Optomotor responses may be measured using assays such as that described in the Examples. After transplantation of the cells of the invention, such optomotor responses will increase, preferably by a statistically significant amount, as shown in the Examples.

This disclosure therefore contemplates administration of the photoreceptor cells and/or photoreceptor progenitor cells described herein for the purpose of preventing, in whole or in part, disease progression, or replacing photoreceptors and photoreceptor progenitors in the recipient (as part of a cell replacement therapy), or some combination thereof. The extent to which either mechanism contributes to the improved outcome will depend on the extent of retinal degeneration in the recipient.

Examples of retinal dysfunction that can be treated by the retinal stem cell populations and methods of the invention include but are not limited to: partial or complete photoreceptor degeneration (as occurs in, e.g., retinitis pigmentosa, cone dystrophies, cone-rod and/or rod-cone dystrophies, and macular degeneration); retina detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV retinitis and toxoplasmosis; inflammatory conditions, such as the uveitidies; tumors, such as retinoblastoma and ocular melanoma; and for the replacement of inner retinal neurons, which are affected in ocular neuropathies including glaucoma, traumatic optic neuropathy, and radiation optic neuropathy and retinopathy.

In one aspect, the cells can treat or alleviate the symptoms of retinitis pigmentosa in a patient in need of the treatment. In another aspect, the cells can treat or alleviate the symptoms of macular degeneration, such as age-related macular degeneration (wet or dry), Stargardt disease, myopic macular degeneration or the like, in a patient in need of this treatment. For all of these treatments, the cells can be autologous or allogeneic to the patient. In a further aspect, the cells of the invention can be administered in combination with other treatments.

Retinitis pigmentosa (RP) refers to a heterogeneous group of hereditary eye disorders characterized by progressive vision loss due to a gradual degeneration of photoreceptors. An estimated 100,000 people in the United States have RP. Classification of this group of disorders under one rubric is based on the clinical features most commonly observed in these patients. The hallmarks of RP are night blindness and reduction of peripheral vision, narrowing of the retinal vessels, and the migration of pigment from disrupted retinal pigment epithelium into the retina, forming clumps of various sizes, often next to the retinal blood vessels.

Typically, patients first notice difficulty seeing at night due to the loss of rod photoreceptors; the remaining cone photoreceptors then become the mainstay of visual function. Over years and decades, however, the cones also degenerate, leading to a progressive loss of vision. In most RP patients, visual field defects begin in the midperiphery, between 30° and 50° from fixation. The defective regions gradually enlarge, leaving islands of vision in the periphery and a constricted central field (called tunnel vision). When the visual field contracts to 200 or less and/or central vision is 20/200 or worse, the patient becomes legally blind.

Inheritance patterns indicate that RP can be transmitted in X-linked (XLRP), autosomal dominant (ADRP), or recessive (ARRP) modes. Among the three genetic types of RP, ADRP is the mildest. These patients often retain good central vision to 60 years of age and beyond. In contrast, patients with the XLRP form of the disease are usually legally blind by 30 to 40 years of age. However, the severity and the age of onset of the symptoms varies greatly among patients with the same genetic type of RP. This variation is apparent even within the same family when presumably all the affected members have the same genetic mutation. Many RP-inducing mutations have now been described. Of the genes identified so far, many encode photoreceptor-specific proteins, several being associated with phototransduction in the rods, such as rhodopsin, subunits of the cGMP phosphodiesterase, and the cGMP-gated $Ca^{2+}$ channel. Multiple mutations in each of the cloned genes have been found. For example, in the case of the rhodopsin gene, 90 different mutations have been identified among ADRP patients.

Regardless of the specific mutation, the vision loss that is most critical to RP patients is due to the gradual degeneration of cones. In many cases, the protein that the RP-causing mutation affects is not even expressed in the cones; the prime example is rhodopsin—the rod-specific visual pigment. Therefore, the loss of cones may be an indirect consequence of a rod-specific mutation. The ability to replace damaged photoreceptors provides an approach to the treatment of this disease.

Age-related macular degeneration (AMD) causes a progressive loss of central vision, and is the most common cause of vision loss in people over age 55. The underlying pathology is degeneration of the photoreceptors. Various studies have implicated hereditary factors, cardiovascular disease, environmental factors such as smoking and light exposure, and nutritional causes as contributing to the risk of developing AMD. RPE degeneration is accompanied by variable loss of both the overlying photoreceptors and the underlying choroidal perfusion. Visual acuity loss or visual field loss occurs when the RPE atrophies and results in secondary loss of the overlying photoreceptor cells that it supplies. The ability to replace RPE and photoreceptor cells provides a means of treating established AMD.

Macular degeneration is broadly divided into two types. In the exudative-neovascular form, or "wet" AMD, which accounts for 10% of all cases, abnormal blood vessel growth occurs under the macula. There is formation of a subretinal network of choroidal neovascularization often associated with intraretinal hemorrhage, subretinal fluid, pigment epithelial detachment, and hyperpigmentation. Eventually, this complex contracts and leaves a distinct elevated scar at the posterior pole. These blood vessels leak fluid and blood into the retina and thus cause damage to the photoreceptors. Wet AMD tends to progress rapidly and can cause severe damage; rapid loss of central vision may occur over just a few months.

The remaining 90% of AMD cases are atrophic macular degeneration (dry form), where there is pigmentary disturbance in the macular region but no elevated macular scar and no hemorrhage or exudation in the region of the macula. In these patients there is a gradual disappearance of the retinal pigment epithelium (RPE), resulting in circumscribed areas of atrophy. Since photoreceptor loss follows the disappearance of RPE, the affected retinal areas have little or no visual function. Vision loss from dry AMD occurs more gradually over the course of many years. These patients usually retain some central vision, although the loss can be severe enough to compromise performance of tasks that require seeing details.

When the appropriate age and clinical findings are accompanied by the loss of visual acuity, visual field, or other visual functions, the condition often is classified as AMD. At times, the step prior to the onset of visual loss has been classified as AMD if the patient has characteristic drusen and relevant family history.

Occasionally, macular degeneration occurs at a much earlier age. Many of these cases are caused by genetic mutations. There are many forms of hereditary macular degeneration, each with its own clinical manifestations and genetic cause. The most common form of juvenile macular degeneration is known as Stargardt disease, which is inherited as an autosomal recessive. Patients are usually diagnosed under the age of 20. Although the progression of vision loss is variable, most of these patients are legally blind by age 50. Mutations that cause Stargardt disease have been identified in the ABCR gene, which codes for a protein that transports retinoids across the photoreceptor membrane.

The photoreceptor progenitor cells of the present invention find use in the treatment of degenerative diseases, and may be delivered as progenitor cells or as the differentiated progeny (rods and cones) thereof, e.g. after commitment to a photoreceptor lineage of interest. The cells are administered in a manner that permits them to graft or migrate to the intended retinal site, such as in the outer nucleated layer, and reconstitute or regenerate the functionally deficient area.

Figure 31:
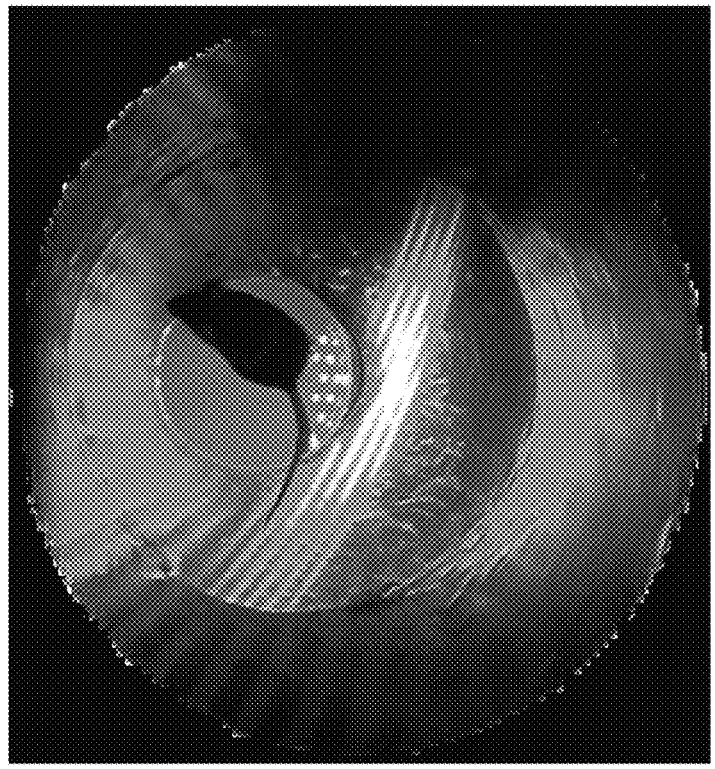
FIG. 31. Optomotor schematic and results. A schematic and an photograph of the optomotor response experimental set up are shown (top left and top right respectively). The data are represented as the number of head tracks in rd1 mice treated with hESC derived photoreceptor progenitors or with iPSC derived photoreceptor progenitors, or in untreated rd1 mice. ANOVA summary F=6.642, p=0.0058 (Tukey's multiple comparisons test). Error bars represent SEM. Dashed line represents the mean response of age-matched WT mice.
Figure 31:
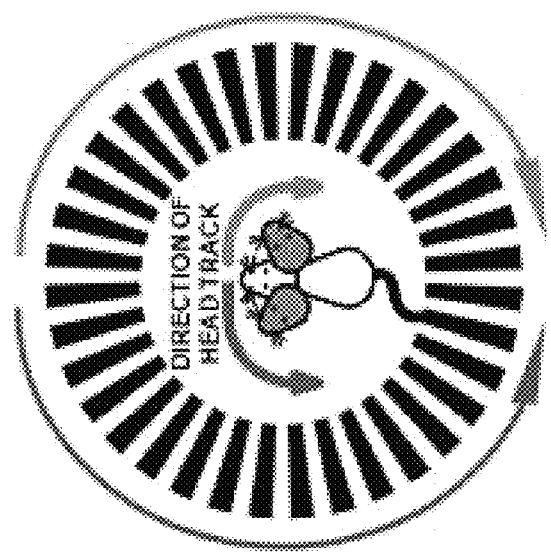
Figure 31:
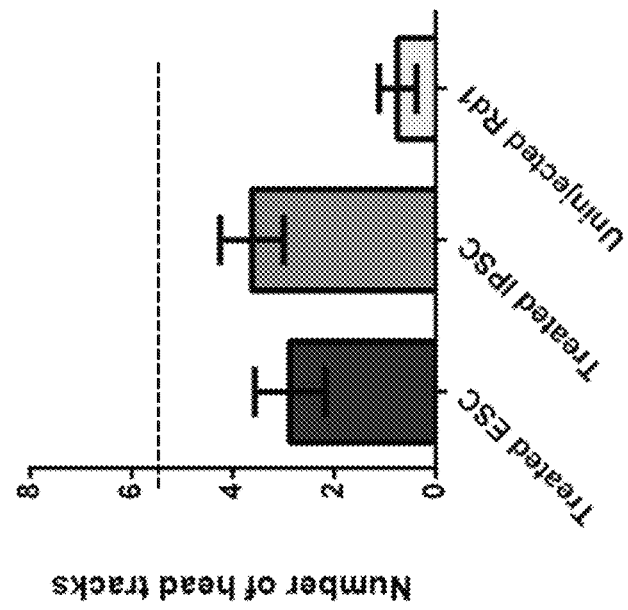

The Examples demonstrate the ability of photoreceptor progenitors disclosed herein to regenerate visual acuity in mouse models of blindness due to photoreceptor degeneration. Visual acuity in such mouse models may be assessed using optomotor responses (or optokinetic nystagmus responses). As shown in FIG. 31, such responses are significantly lower in rd1 mice as compared to wild type mice (e.g., the rd1 mouse has less than 1 head turn versus almost 6 head turns for a wild type mouse).

In another aspect the disclosure provides a method of drug delivery, comprising administering photoreceptors and photoreceptor progenitors described herein or produced by any method described herein to said patient, wherein said photoreceptors and photoreceptor progenitors deliver said drug. A wide range of drugs can be used. The engineered photoreceptors and photoreceptor progenitors may be prepared so that they include one or more compounds selected from the group consisting of drugs that act at synaptic and neuroeffector junctional sites; drugs that act on the central nervous system; drugs that modulate inflammatory responses such as anti-inflammatory agents including non-steroidal anti-inflammatory agent; drugs that affect renal and/or cardiovascular function; drugs that affect gastrointestinal function; antibiotics; anti-viral agents, anti-neoplastic and anti-cancer agents; immunomodulatory agents; anesthetic, steroidal agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, nutritional agent, drugs acting on the blood and/or the blood-forming organs; hormones; hormone antagonists; agents affecting calcification and bone turnover, vitamins, gene therapy agents; or other agents such as targeting agents, etc.

For example, the photoreceptor and/or photoreceptor progenitors may be prepared so that they include one or more compounds selected from the group consisting of drugs that act at synaptic and neuroeffector junctional sites (e.g., acetylcholine, methacholine, pilocarpine, atropine, scopolamine, physostigmine, succinylcholine, epinephrine, norepinephrine, dopamine, dobutamine, isoproterenol, albuterol, propranolol, serotonin); drugs that act on the central nervous system (e.g., clonazepam, diazepam, lorazepam, benzocaine, bupivacaine, lidocaine, tetracaine, ropivacaine, amitriptyline, fluoxetine, paroxetine, valproic acid, carbamazepine, bromocriptine, morphine, fentanyl, naltrexone, naloxone); drugs that modulate inflammatory responses (e.g., aspirin, indomethacin, ibuprofen, naproxen, steroids, cromolyn sodium, theophylline); drugs that affect renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, mevalonate); drugs that affect gastrointestinal function (e.g., omeprazole, sucralfate); antibiotics (e.g., tetracycline, clindamycin, amphotericin B, quinine, methicillin, vancomycin, penicillin G, amoxicillin, gentamicin, erythromycin, ciprofloxacin, doxycycline, acyclovir, zidovudine (AZT), ddC, ddI, ribavirin, cefaclor, cephalexin, streptomycin, gentamicin, tobramycin, chloramphenicol, isoniazid, fluconazole, amantadine, interferon); anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, decarbazine); immunomodulatory agents (e.g., interleukins, interferons, GM-CSF, TNFα, TNFβ, cyclosporine, FK506, azathioprine, steroids); drugs acting on the blood and/or the blood-forming organs (e.g., interleukins, G-CSF, GM-CSF, erythropoietin, vitamins, iron, copper, vitamin B12, folic acid, heparin, warfarin, coumarin); hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride), vitamins (e.g., riboflavin, nicotinic acid, pyridoxine, pantothenic acid, biotin, choline, inositol, carnitine, vitamin C, vitamin A, vitamin E, vitamin K), gene therapy agents (e.g., viral vectors, nucleic-acid-bearing liposomes, DNA-protein conjugates, anti-sense agents); or other agents such as targeting agents etc. The photoreceptors and photoreceptor progenitors of the present invention can be engineered to include one or more therapeutic agents which are released or secreted by these cells either in a passive manner (diffuse out of the cells over time) or in an active manner (upon deliberate rupture or lysis of the cells). hESCs and/or hiPSCs may be genetically modified and used to produce photoreceptors and photoreceptor progenitors that express a desired agent for treatment of a disease. In one aspect, hESCs and/or hiPSCs could be genetically modified to express an antitumor agent. Photoreceptors and photoreceptor progenitors produced from such genetically modified hESCs, hiPSCs and MLPs may be used to deliver such antitumor agent to a tumor for the treatment of a neoplastic disease, including for example retinoblastoma.

In certain embodiments, the photoreceptors and photoreceptor progenitors have been engineered to include one or more therapeutic agents, such as a small molecule drug, aptamer or other nucleic acid agent, or recombinant proteins.

Genetically engineered progenitor cells or photoreceptors can also be used to target gene products to sites of degeneration. These gene products can include survival-promoting factors to rescue native degenerating neurons, factors that can act in an autocrine manner to promote survival and differentiation of grafted cells into site-specific neurons or to deliver neurotransmitter(s) to permit functional recovery. Ex vivo gene therapy, e.g., the recombinantly engineering the progenitor cells or the photoreceptors in culture, could be used effectively as a neuroprotective strategy to prevent retinal cell loss in RP, AMD, and glaucoma and in diseases that cause retinal detachment, by the delivery of growth factors and neurotrophins such as FGF2, NGF, ciliary neurotrophic factor (CNTF), and brain derived neurotrophic factor (BDNF), which factors have been shown to significantly slow the process of cell death in models of retinal degeneration. Therapy using photoreceptor progenitor and/or photoreceptor cells engineered to synthesize a growth factor or a combination of growth factors can not only ensure sustained delivery of neuroprotectants, but may also reconstruct damaged retina.

The photoreceptor progenitor cells of the present invention or differentiated photoreceptors thereof (collectively "preparations of cells") may be administered conjointly with one or more other therapeutic agents. As used herein, the phrases "conjoint administration" and "administered conjointly" refer to any form of administration in combination of two or more different therapeutic entities such that the second agent is administered while the previously administered therapeutic agent (such as the cells) is still effective in the body (e.g., the two therapeutics are simultaneously effective in the patient, which may include synergistic effects of the two agents). For example, the different therapeutic agents can be administered either in the same formulation, where the cells are amenable to co-formulation, or in a separate formulations, either concomitantly or sequentially. Thus, an individual who receives such treatment can benefit from a combined effect of transplanted cells and one or more different therapeutic agents.

One or more angiogenesis inhibitors may be administered in combination (i.e., conjointly) with the preparations of cells, preferably in a therapeutically effective amount for the prevention or treatment of ocular disease, such as an angiogenesis-associated ocular disease. Exemplary ocular diseases include macular degeneration (e.g., wet AMD or dry AMD), diabetic retinopathy, and choroidal neovascularization. Exemplary angiogenesis inhibitors include VEGF antagonists, such as inhibitors of VEGF and/or a VEGF receptor (VEGFR, e.g., VEGFR1 (FLT1, FLT), VEGFR2 (KDR, FLK1, VEGFR, CD309), VEGFR3 (FLT4, PCL)), such as peptides, peptidomimetics, small molecules, chemicals, or nucleic acids, e.g., pegaptanib sodium, aflibercept, bevasiranib, rapamycin, AGN-745, vitalanib, pazopanib, NT-502, NT-503, or PLG101, CPD791 (a di-Fab' polyethylene glycol (PEG) conjugate that inhibits VEGFR-2), anti-VEGF antibodies or functional fragments thereof (such as bevacizumab (AVASTIN®) or ranibizumab (LUCENTIS®)), or anti-VEGF receptor antibodies (such as IMC-1121(B) (a monoclonal antibody to VEGFR-2), or IMC-18F1 (an antibody to the extracellular binding domain of VEGFR-1)). Additional exemplary inhibitors of VEGF activity include fragments or domains of VEGFR receptor, an example of which is VEGF-Trap (Aflibercept), a fusion protein of domain 2 of VEGFR-1 and domain 3 of VEGFR-2 with the Fc fragment of IgG1. Another exemplary VEGFR inhibitors is AZD-2171 (Cediranib), which inhibits VEGF receptors 1 and 2. Additional exemplary VEGF antagonists include tyrosine kinase inhibitors (TKIs), including TKIs that reportedly inhibit VEGFR-1 and/or VEGFR-2, such as sorafenib (Nexavar), SU5416 (Semaxinib), SU11248/Sunitinib (Sutent), and Vandetanib (ZD 6474). Additional exemplary VEGF antagonists include Ly317615 (Enzastaurin), which is though to target a down-stream kinase involved in VEGFR signaling (protein kinase C). Additional exemplary angiogenesis inhibitors include inhibitors of alpha5beta1 integrin activity, including and anti-alpha5beta1 integrin antibodies or functional fragments thereof (such as volociximab), a peptide, peptidomimetic, small molecule, chemical or nucleic acid such as 3-(2-{1-alkyl-5-[(pyridine-2-ylamino)-methyl]-pyrrolidin-3-yloxy}-acetylamino)-2-(alkyl-amino)-propionic acid, (S)-2-[(2,4,6-trimethylphenyl) sulfonyl]amino-3-[7-benzyloxycarbonyl-8-(2-pyridinylaminomethyl)-1-oxa-2,7-diazaspiro-(4,4)-non-2-en-3-yl]carbonylamino propionic acid, EMD478761, or RC*D(ThioP)C* (Arg-Cys-Asp-Thioproline-Cys; asterisks denote cyclizing by a disulfide bond through the cysteine residues). Additional exemplary angiogenesis inhibitors include 2-methoxyestradiol, alphaVbeta3 inhibitors, Angiopoietin 2, angiostatic steroids and heparin, angiostatin, angiostatin-related molecules, anti-alpha5beta1 integrin antibodies, anti-cathepsin S antibodies, antithrombin III fragment, bevacizumab, calreticulin, canstatin, carboxyamidotriazole, Cartilage-Derived Angiogenesis Inhibitory Factor, CDAI, CM101, CXCL10, endostatin, IFN-α, IFN-β, IFN-γ, IL-12, IL-18, IL-4, linomide, maspin, matrix metalloproteinase inhibitors, Meth-1, Meth-2, osteopontin, pegaptanib, platelet factor-4, prolactin, proliferin-related protein, prothrombin (kringle domain-2), ranibizumab, restin, soluble NRP-1, soluble VEGFR-1, SPARC, SU5416, suramin, tecogalan, tetrathiomolybdate, thalidomide, lenalidomide, thrombospondin, TIMP, TNP-470, TSP-1, TSP-2, vasostatin, VEGFR antagonists, VEGI, Volociximab (also known as M200), a fibronectin fragment such as anastellin (see Yi and Ruoslahti, Proc Natl Acad Sci USA. 2001 Jan. 16; 98(2):620-4) or any combination thereof. Said angiogenesis inhibitor is preferably in an amount sufficient to prevent or treat proliferative (neovascular) eye disease, such as choroidal neovascular membrane (CNV) associated with wet AMD and other diseases of the retina. Additional exemplary angiogenesis inhibitors include: Lenvatinib (E7080), Motesanib (AMG 706), Pazopanib (Votrient), and an IL-6 antagonist such as anti-IL-6 antibody. Additional exemplary angiogenesis inhibitors include fragments, mimetics, chimeras, fusions, analogs, and/or domains of any of the foregoing. Additional exemplary angiogenesis inhibitors include combinations of any of the foregoing. In an exemplary embodiment, the preparation of cells comprises an anti-VEGF antibody, e.g., bevacizumab, such as between about 0.1 mg to about 6.0 mg, e.g., about 1.25 mg and about 2.5 mg bevacizumab, per injection into the eye. In further exemplary embodiments, the preparation of cells comprises one or more inhibitors of VEGF activity and one or more inhibitors of alpha5beta1 integrin activity.

One or more anti-inflammatory agents may be administered in combination with the preparation of cells. Exemplary anti-inflammatory agents include: glucocorticoids, non-steroidal anti-inflammatory drugs, aspirin, ibuprofen, naproxen, cyclooxygenase (COX) enzyme inhibitors, aldosterone, beclometasone, betamethasone, corticosteroids, cortisol, cortisone acetate, deoxycorticosterone acetate, dexamethasone, fludrocortisone acetate, fluocinolone acetonide (e.g., ILUVIEN®), glucocorticoids, hydrocortisone, methylprednisolone, prednisolone, prednisone, steroids, and triamcinolone.

One or more antioxidants, antioxidant cofactors, and/or other factors contribute to increased antioxidant activity may be administered in combination with the preparation of cells, examples of which may include OT-551 (Othera), vitamin C, vitamin E, beta carotene, zinc (e.g., zinc oxide), and/or copper (e.g., copper oxide).

One or more macular xanthophylls (such as lutein and/or zeaxanthin) may be administered in combination with the preparation of cells.

One or more long-chain omega-3 fatty acids, such as docosahexaenoic acid (DHA) and/or eicosapentaenoic acid (EPA)), may be administered in combination with the preparation of cells.

One or more amyloid inhibitors, such as fenretinide, Arc-1905, Copaxone (glatiramer acetate, Teva), RN6G (PF-4382923, Pfizer) (a humanized monoclonal antibody versus ABeta40 and ABeta42), GSK933776 (GlaxoSmithKline) (anti-amyloid antibody), may be administered in combination with the preparation of cells.

One or more ciliary neurotrophic factor (CNTF) agonists (e.g., CNTF which may be delivered in an intraocular device such as NT-501 (Neurotech)) may be administered in combination with the preparation of cells.

One or more inhibitors of RPE65, such as ACU-4429 (Aculea, Inc.) may be administered in combination with the preparation of cells.

One or more factors that target A2E and/or lipofuscin accumulation, such as Fenretinide, and ACU-4429, may be administered in combination with the preparation of cells.

One or more downregulators or inhibitors of photoreceptor function and/or metabolism, such as fenretinide and ACU-4429, may be administered in combination with the preparation of cells.

One or more α2-adrenergic receptor agonists, such as Brimonidine tartrate, may be administered in combination with the preparation of cells.

One or more selective serotonin 1A agonists, such as Tandospirone (AL-8309B), may be administered in combination with the preparation of cells.

In combination with the preparation of cells, one or more factors targeting C-5, membrane attack complex (C5b-9) and/or any other Drusen component may be administered, examples of which include inhibitors of complement factors D, C-3, C-3a, C5, and C5a, and/or agonists of factor H, such as ARC 1905 (Ophthotec) (an anti-C5 Aptamer that selectively inhibits C5), POT-4 (Potentia) (a compstatin derivative that inhibits C3), complement factor H, Eculizumab (Soliris, Alexion) (a humanized IgG antibody that inhibits C5), and/or FCFD4514S (Genentech, San Francisco) (a monoclonal antibody against complement factor D).

One or more immunosuppressants, such as Sirolimus (rapamycin), may be administered in combination with the preparation of cells.

One or more agents that prevent or treat the accumulation of lipofuscin, such as piracetam, centrophenoxine, acetyl-L-carnitine, *Ginko Biloba* or an extract or preparation thereof, and/or DMAE (Dimethylethanolamine), may be administered in combination with the preparation of cells.

Where one or more agent (such as angiogenesis inhibitors, antioxidants, antioxidant cofactors, other factors contribute to increased antioxidant activity, macular xanthophylls, long-chain omega-3 fatty acids, amyloid inhibitors, CNTF agonists, inhibitors of RPE65, factors that target A2E and/or lipofuscin accumulation, downregulators or inhibitors of photoreceptor function and/or metabolism, α2-adrenergic receptor agonists, selective serotonin 1A agonists, factors targeting C-5, membrane attack complex (C5b-9) and/or any other Drusen component, immunosuppressants, agents that prevent or treat the accumulation of lipofuscin, etc.) is administered in combination with the preparation of cells, said agent may be administered concurrently with, prior to, and/or subsequent to said preparation of cells. For example, said agent may be administered to the eye of the patient during the procedure in which said preparation of cells is introduced into the eye of said patient. Administration of said agent may begin prior to and/or continue after administration of said cells to the eye of the patient. For example, said agent may be provided in solution, suspension, as a sustained release form, and/or in a sustained delivery system (e.g., the Allergan Novadur™ delivery system, the NT-501, or another intraocular device or sustained release system).

In certain embodiments, the cells may be engineered to include a recombinant expression construct, which when expressed by the cells in vivo, produces a recombinant version of an agent set out herein. In the case of antibody, this includes both two-chain monoclonal antibodies, as well as epitope binding fragments thereof, e.g., Fab, Fab' and F(ab')$_2$, Fd, Fvs, single-chain Fvs (scFv), disulfide-linked Fvs (sdFv), and fragments comprising either a VL or VH domain, as well as fibronectin scaffolded and other antibody CDR mimetics. The engineered cells may include expression constructs encoding recombinant peptides and proteins, as well as constructs which, when transcribed, form transcripts which give rise to RNA interference agents (such as siRNA, hairpin RNA or the like), aptamers, decoys (bind to transcription factors and inhibit expression of native gene), antisense or the like. The recombinant gene can be operably linked to a transcriptional regulatory element, such as promoter and/or enhancer, which is active in the transplanted cell (such as a constitutively active or photoreceptor-active element) or which can be regulated by small molecules.

Exemplary recombinant agents to be expressed by the transplanted cells include anti-angiogeneic agents, such as those which reduce occurrence of choroidal neovascularization (wet AMD). These include agents which inhibit VEGF mediated vascularization of the eye, such as anti-VEGF antibodies and VEGF receptor traps. Such proteins include antibodies and antibody analogs (such as single chain antibodies, monobodies, antigen binding sites and the like) such as ranibizumab, VEGF-traps such as Aflibercept which are soluble proteins including ligand binding domains from VEGF receptors, which bind to either VEGF or the VEGF receptor and block receptor activation.

Activation of alternative complement pathway implicated in disease progression for certain patients, particularly in the case of dry AMD. Another class of exemplary recombinant agents to be expressed by the transplanted cells include complement inhibitors, such as complement Factor D, Factor C5 and/or Factor C3 Inhibitors. These may be, merely to illustrate, RNA agents or recombinant antibodies.

Drusen deposits in dry AMD resemble amyloid deposits. Accordingly, the transplanted cells may be engineered to express an anti β-amyloid agent. These include recombinant antibodies, β-secretase inhibitors, and the like.

The transplanted cells may also be engineered to express one or more anti-inflammatory agents, such as antagonists/inhibitors of proinflammatory cytokines such as IL-1, IL-2, IL-3, and TNF-α or anti-inflammatory cytokines such as IL-37. The antagonists/inhibitors of proinflammatory cytokines include recombinant antibodies, receptor traps, apatmers, etc. In one embodiment, the transplanted cells can be engineered to express recombinant lipocortin, a potent anti-inflammatory protein.

In the methods of the invention, cells to be transplanted are transferred to a recipient in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium.

The pharmaceutical preparations of the invention are optionally packaged in a suitable container with written instructions for a desired purpose. Such formulations may comprise a cocktail of retinal differentiation and/or trophic factors, in a form suitable for combining with photoreceptor progenitor or photoreceptor cells. Such a composition may further comprise suitable buffers and/or excipients appropriate for transfer into an animal. Such compositions may further comprise the cells to be engrafted.

Pharmaceutical Preparations

The PRPCs or photoreceptor cells may be formulated with a pharmaceutically acceptable carrier. For example, PRPCs or photoreceptor cells may be administered alone or as a component of a pharmaceutical formulation. The subject compounds may be formulated for administration in any convenient way for use in medicine. Pharmaceutical preparations suitable for administration may comprise the PRPCs or photoreceptor cells, in combination with one or more pharmaceutically acceptable sterile isotonic aqueous or non-aqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents. Exemplary pharmaceutical preparations comprises the PRPCs or photoreceptor cells in combination with ALCON® BSS PLUS® (a balanced salt solution containing, in each mL, sodium chloride 7.14 mg, potassium chloride 0.38 mg, calcium chloride dihydrate 0.154 mg, magnesium chloride hexahydrate 0.2 mg, dibasic sodium phosphate 0.42 mg, sodium bicarbonate 2.1 mg, dextrose 0.92 mg, glutathione disulfide (oxidized glutathione) 0.184 mg, hydrochloric acid and/or sodium hydroxide (to adjust pH to approximately 7.4) in water).

When administered, the pharmaceutical preparations for use in this disclosure may be in a pyrogen-free, physiologically acceptable form.

The preparation comprising PRPCS or photoreceptor cells used in the methods described herein may be transplanted in a suspension, gel, colloid, slurry, or mixture. Further, the preparation may desirably be encapsulated or injected in a viscous form into the vitreous humor for delivery to the site of retinal or choroidal damage. Also, at the time of injection, cryopreserved PRPCS photoreceptor cells may be resuspended with commercially available balanced salt solution to achieve the desired osmolality and concentration for administration by subretinal injection. The preparation may be administered to an area of the pericentral macula that was not completely lost to disease, which may promote attachment and/or survival of the administered cells.

The PRPCS and/or photoreceptor cells may be frozen (cryopreserved) as described herein. Upon thawing, the viability of such cells may be at least 20%, at least 30%, at least 40%, at least 50%, at least 60%, at least 70%, at least 80%, at least 90% at least 95% or about 100% (e.g., at least 20%, at least 30%, at least 40%, at least 50%, at least 60%, at least 70%, at least 80%, at least 90% at least 95% or about 100% of the cells harvested after thawing are viable or at least 20%, at least 30%, at least 40%, at least 50%, at least 60%, at least 70%, at least 80%, at least 90% at least 95% or about 100% of the cell number initially frozen are harvested in a viable state after thawing). In some instances, the viability of the cells prior to and after thawing is about 80%. In some instances, at least 90% or at least 95% or about 95% of cells that are frozen are recovered. The cells may be frozen as single cells or as aggregates. For example, the cells may be frozen as neurospheres.

The PRPCS or photoreceptor cells of the disclosure may be delivered in a pharmaceutically acceptable ophthalmic formulation by intraocular injection. When administering the formulation by intravitreal injection, for example, the solution may be concentrated so that minimized volumes may be delivered. Concentrations for injections may be at any amount that is effective and non-toxic, depending upon the factors described herein. The pharmaceutical preparations of PRPCS or photoreceptor cells for treatment of a patient may be formulated at doses of at least about $10^4$ cells/mL. The PRPCS or photoreceptor cell preparations for treatment of a patient are formulated at doses of at least about $10^3$, $10^4$, $10^5$, $10^6$, 107, $10^8$, $10^9$, or $10^{10}$ PRPCS or photoreceptor cells/mL. For example, the PRPCS or photoreceptor cells may be formulated in a pharmaceutically acceptable carrier or excipient.

The pharmaceutical preparations of PRPCS or photoreceptor cells described herein may comprise at least about 1,000; 2,000; 3,000; 4,000; 5,000; 6,000; 7,000; 8,000; or 9,000 PRPCS or photoreceptor cells. The pharmaceutical preparations of PRPCS or photoreceptor cells may comprise at least about $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 105$, $7 \times 10^5$, $8 \times 105$, $9 \times 10^5$, $1 \times 10^6$, $2 \times 10^6$, $3 \times 10^6$, $4 \times 10^6$, $5 \times 10^6$, $6 \times 10^6$, $7 \times 106$, $8 \times 106$, $9 \times 106$, $1 \times 10^7$, $2 \times 10^7$, $3 \times 10^7$, $4 \times 10^7$, $5 \times 10^7$, $6 \times 107$, $7 \times 10^7$, $8 \times 10^7$, $9 \times 10^7$, $1 \times 10^8$, $2 \times 10^8$, $3 \times 10^8$, $4 \times 10^8$, $5 \times 108$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ PRPCS or photoreceptor cells. The pharmaceutical preparations of PRPCS or photoreceptor cells may comprise at least about $1 \times 10^2$-$1 \times 10^3$, $1 \times 10^2$-$1 \times 10^4$, $1 \times 10^4$-$1 \times 10^5$, or $1 \times 10^3$-$1 \times 10^6$ PRPCS OR PRPCS or photoreceptor cells. The pharmaceutical preparations of PRPCS or photoreceptor cells may comprise at least about 10,000, 20,000, 25,000, 50,000, 75,000, 100,000, 125,000, 150,000, 175,000, 180,000, 185,000, 190,000, or 200,000 PRPCS or photoreceptor cells. For example, the pharmaceutical preparation of PRPCS or photoreceptor cells may comprise at least about 20,000-200,000 PRPCS or photoreceptor cells in a volume at least about 50-200 µL. Further, the pharmaceutical preparation of PRPCS or photoreceptor cells may comprise about 50,000 PRPCS or photoreceptor is in a volume of 150 µL, about 200,000 PRPCS or photoreceptor cells in a volume of 150 µL, or at least about 180,000 PRPCS or photoreceptor cells in a volume at least about 150 µL.

In the aforesaid pharmaceutical preparations and compositions, the number of PRPCS or photoreceptor cells or concentration of PRPCS or photoreceptor cells may be determined by counting viable cells and excluding non-viable cells. For example, non-viable PRPCS or photoreceptor may be detected by failure to exclude a vital dye (such as Trypan Blue), or using a functional assay (such as the ability to adhere to a culture substrate, phagocytosis, etc.). Additionally, the number of PRPCS or photoreceptor cells or concentration of PRPCS or photoreceptor cells may be determined by counting cells that express one or more PRPCS or photoreceptor cell markers and/or excluding cells that express one or more markers indicative of a cell type other than PRPCS or photoreceptor.

The PRPCS or photoreceptor cells may be formulated for delivery in a pharmaceutically acceptable ophthalmic vehicle, such that the preparation is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoridal space, conjunctiva, subconjunctival space, episcleral space, intracorneal space, epicorneal space, pars plana, surgically-induced avascular regions, or the macula.

The PRPCS or photoreceptor cells may be contained in a sheet of cells. For example, a sheet of cells comprising PRPCS or photoreceptor cells may be prepared by culturing PRPCS or photoreceptor cells on a substrate from which an intact sheet of cells can be released, e.g., a thermoresponsive polymer such as a thermoresponsive poly(N-isopropylacrylamide) (PNIPAAm)-grafted surface, upon which cells adhere and proliferate at the culture temperature, and then upon a temperature shift, the surface characteristics are altered causing release the cultured sheet of cells (e.g., by cooling to below the lower critical solution temperature (LCST) (see da Silva et al., Trends Biotechnol. 2007 December; 25(12):577-83; Hsiue et al., Transplantation. 2006 Feb. 15; 81(3):473-6; Ide, T. et al. (2006); Biomaterials 27, 607-614, Sumide, T. et al. (2005), FASEB J. 20, 392-394; Nishida, K. et al. (2004), Transplantation 77, 379-385; and Nishida, K. et al. (2004), N. Engl. J. Med. 351, 1187-1196 each of which is incorporated by reference herein in its entirety). The sheet of cells may be adherent to a substrate suitable for transplantation, such as a substrate that may dissolve in vivo when the sheet is transplanted into a host organism, e.g., prepared by culturing the cells on a substrate suitable for transplantation, or releasing the cells from another substrate (such as a thermoresponsive polymer) onto a substrate suitable for transplantation. An exemplary substrate potentially suitable for transplantation may comprise gelatin (see Hsiue et al., supra). Alternative substrates that may be suitable for transplantation include fibrin-based matrixes and others. The sheet of cells may be used in the manufacture of a medicament for the prevention or treatment of a disease of retinal degeneration. The sheet of PRPCS OR photoreceptor cells may be formulated for introduction into the eye of a subject in need thereof. For example, the sheet of cells may be introduced into an eye in need thereof by subfoveal membranectomy with transplantation the sheet of PRPCS or photoreceptor cells, or may be used for the manufacture of a medicament for transplantation after subfoveal membranectomy.

The volume of preparation administered according to the methods described herein may be dependent on factors such as the mode of administration, number of P PRPCS or photoreceptor cells, age and weight of the patient, and type and severity of the disease being treated. If administered by injection, the volume of a pharmaceutical preparations of PRPCS or photoreceptor cells of the disclosure may be from at least about 1, 1.5, 2, 2.5, 3, 4, or 5 mL. The volume may be at least about 1-2 mL. For example, if administered by injection, the volume of a pharmaceutical preparation of PRPCS or photoreceptor cells of the disclosure may be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 µL (microliters). For example, the volume of a preparation of the disclosure may be from at least about 10-50, 20-50, 25-50, or 1-200 µL. The volume of a preparation of the disclosure may be at least about 10, 20, 30, 40, 50, 100, 110, 120, 130, 140, 150, 160, 170, 180, 190, or 200 µL, or higher.

For example, the preparation may comprise at least about $1 \times 103$, $2 \times 103$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, or $9 \times 10^4$ PRPCS or photoreceptor cells per µL. The preparation may comprise 2000 PRPCS or photoreceptor cells per µL, for example, 100,000 PRPCS or photoreceptor cells per 50 µL or 180,000 PRPCS or photoreceptor cells per 90 µL.

The method of treating retinal degeneration may further comprise administration of an immunosuppressant. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, and tacrolimus. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the PRPCS or photoreceptor cells. Immunosuppressive therapy may continue for weeks, months, years, or indefinitely following administration of PRPCS or photoreceptor cells. For example, the patient may be administered 5 mg/kg cyclosporin for 6 weeks following administration of the PRPCS or photoreceptor cells.

The method of treatment of retinal degeneration may comprise the administration of a single dose of PRPCS or photoreceptor cells. Also, the methods of treatment described herein may comprise a course of therapy where PRPCS or photoreceptor cells are administered multiple times over some period. Exemplary courses of treatment may comprise weekly, biweekly, monthly, quarterly, biannually, or yearly treatments. Alternatively, treatment may proceed in phases whereby multiple doses are administered initially (e.g., daily doses for the first week), and subsequently fewer and less frequent doses are needed.

If administered by intraocular injection, the PRPCS or photoreceptor cells may be delivered one or more times periodically throughout the life of a patient. For example, the PRPCS or photoreceptor cells may be delivered once per year, once every 6-12 months, once every 3-6 months, once every 1-3 months, or once every 1-4 weeks. Alternatively, more frequent administration may be desirable for certain conditions or disorders. If administered by an implant or device, the PRPCS or photoreceptor cells may be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

The methods described herein may further comprise the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

The PRPCs or PRs may be used in the manufacture of a medicament to treat retinal degeneration. The disclosure also encompasses the use of the preparation comprising PRPCs or PRs in the treatment of blindness. For example, the preparations comprising human PRPCs or PRs may be used to treat retinal degeneration associated with a number of vision-altering ailments that result in photoreceptor damage and blindness, such as, diabetic retinopathy, macular degeneration (including age related macular degeneration, e.g., wet age related macular degeneration and dry age related macular degeneration), retinitis pigmentosa, and Stargardt Disease (fundus flavimaculatus), night blindness and color blindness. The preparation may comprise at least about 5,000-500,000 PRPCs or PRs (e.g., 100,00 PRPCs or PRs) which may be administered to the retina to treat retinal degeneration associated with a number of vision-altering ailments that result in photoreceptor damage and blindness, such as, diabetic retinopathy, macular degeneration (including age related macular degeneration), retinitis pigmentosa, and Stargardt Disease (fundus flavimaculatus).

The PRPCs or PRs provided herein may be PRPCs or PRs. Note, however, that the human cells may be used in human patients, as well as in animal models or animal patients. For example, the human cells may be tested in mouse, rat, cat, dog, or non-human primate models of retinal degeneration. Additionally, the human cells may be used therapeutically to treat animals in need thereof, such as in veterinary medicine. Examples of veterinary subjects or patients include without limitation dogs, cats, and other companion animals, and economically valuable animals such as livestock and horses.

The following are examples to illustrate the invention and should not be viewed as limiting the scope of the invention.

EXAMPLES

Example 1: Generation of Photoreceptor Progenitor Cells

Human embryonic stem cells were cultured under feeder free conditions in mTESR1 media (Stem Cell Technology) on a Matrigel™ (a soluble preparation from Engelbreth-Holm-Swarm (EHS) mouse sarcoma cells, BD Biosciences) surface. Upon 80-90% confluence, cells were passaged or frozen. Passaging of stem cells was performed using enzymatic (dispase) or non-enzymatic (EDTA-based cell dissociation buffer, Invitrogen) techniques.

Direct differentiation methods were used for generation of eye field progenitor cells, retinal neural progenitor cells, photoreceptor progenitor cells and retinal photoreceptor cells. Formation of embryoid bodies was not required.

Figure 19:
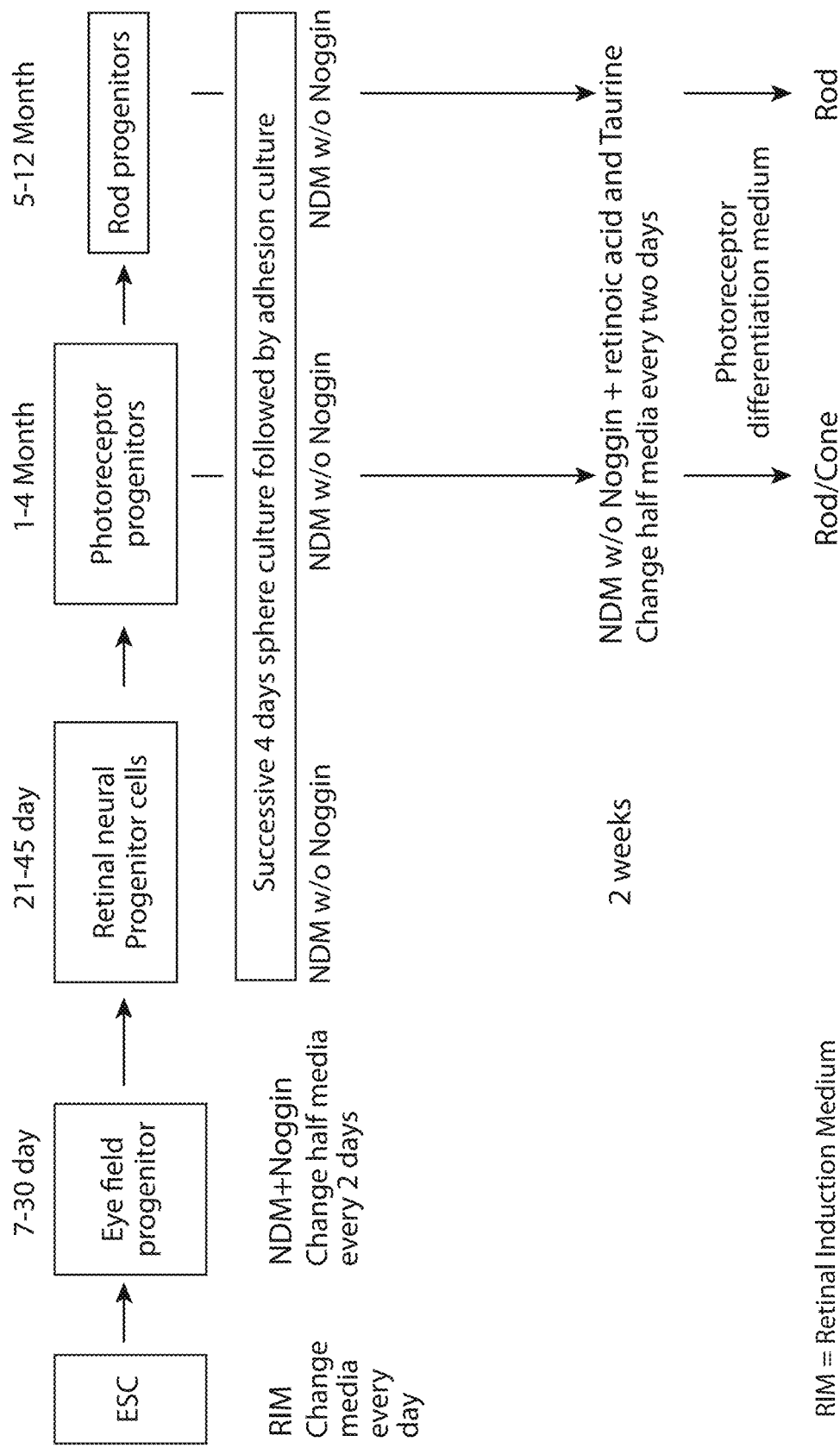
FIG. 19 illustrates the overall method used for photoreceptor development in Examples 1-2 and further illustrates the media used at each step of the process.
Figure 20:
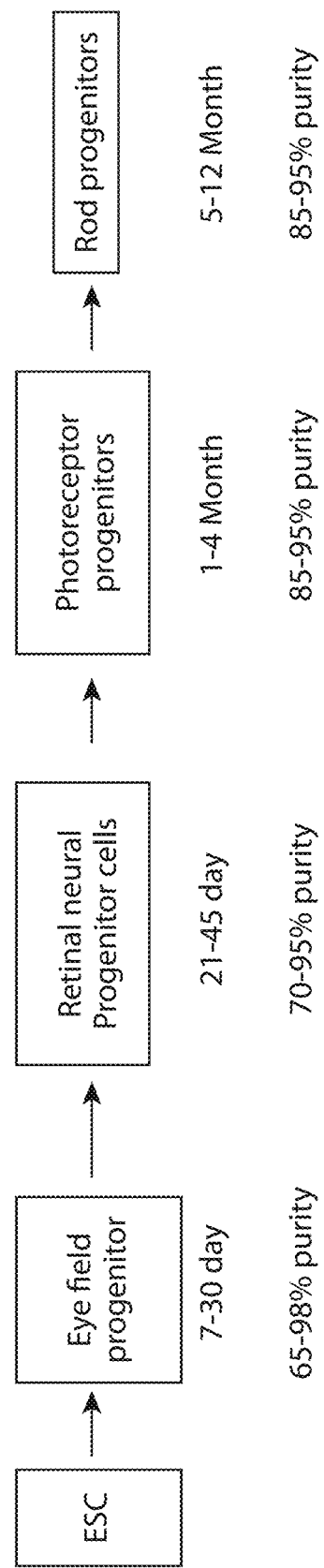
FIG. 20 illustrates the timing of photoreceptor cell and photoreceptor progenitor cell development in Examples 1-2.

The overall method used for photoreceptor development in these examples is schematically illustrated in FIG. 19, which further illustrates the media used at each step of the process.

Based on staining data it was determined that the cells become EFPC between day 7-day 30 (indicated by staining done at day 20 which confirmed this cell identity), they become RNPC between day 21-day 45 (indicated by staining done at day 30), and they become PhRPC between 1-4 month (based on staining done at day 90).

Additionally it was estimated that the timing at which different cell types arose using the methods described in Example 1 were as follows:

Eye Field Progenitors (EFPC): 7-30 days/65%-98% purity

Retinal Neural Progenitors (RNPC): 21-45 days/70%-95% purity

Photoreceptor Progenitors (PhRPs) capable of becoming both rod photoreceptors and cone photoreceptors: 1-4 months/85%-95% purity Photoreceptor Progenitors (PhRPs) thought to have lost or experienced reduction in their capability of becoming rod photoreceptors (but not cone photoreceptors): 5-12 months/ 85%-95% purity.

Figure 1:
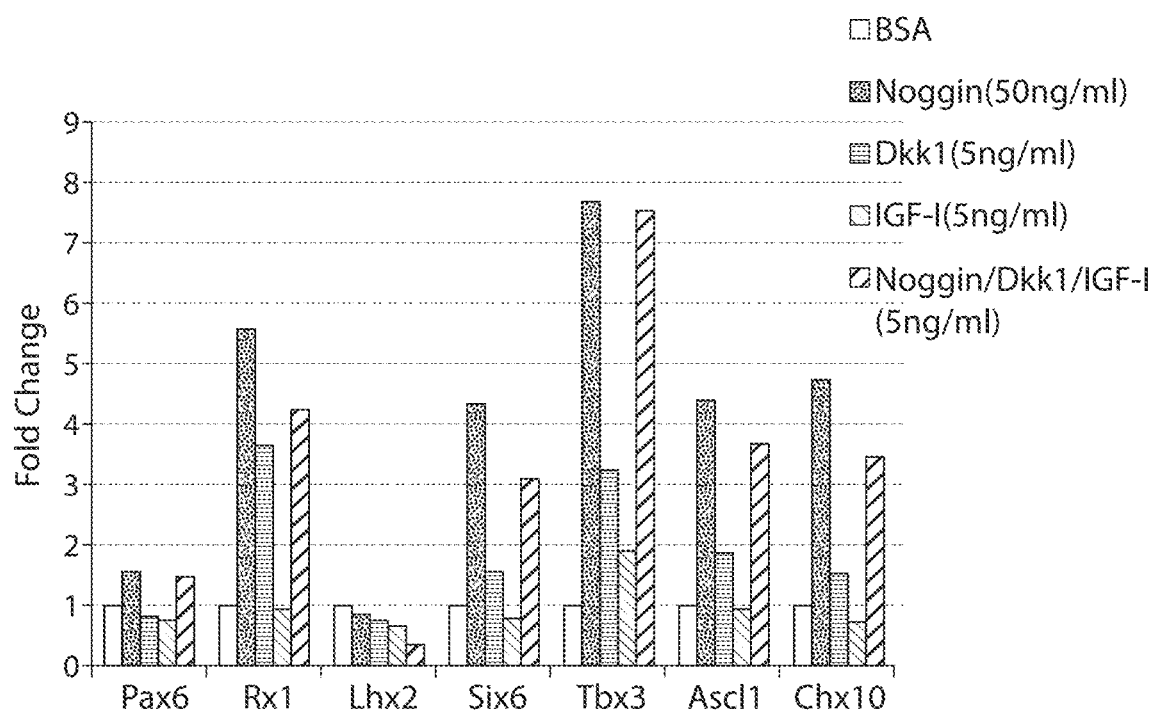
FIG. 1. Real-time PCR analysis of transcripts of eye field transcription factors in cells differentiated under different conditions.

Day 0: Cell differentiation of human pluripotent stem cells was induced at 15-20% confluence. Culture media was changed to retinal induction (RI) medium: DMEM/F12 supplied with 4.5 g/L D-glucose, 100 unit/ml of penicillin, 100 μg/ml of streptomycin, 1% (or optionally 0.1 to 5%) N2 supplement (Invitrogen), 0.2% (or optionally 0.05-2.0%) B27 supplement, 0.1 mM MEM non-essential amino acids solution, 25 μg/ml (or optionally 5-50 g/ml) human insulin was added to the RI medium. The Smad inhibitor Noggin was also included and increased the expression of eye field transcription factors when included at a concentration of 10-100 ng/ml or preferably 50 ng/ml. As shown in FIG. 1, inclusion of different factors including 50 ng/ml Noggin, 5 ng/ml Dkk1, 5 ng/ml IGF-1, or a combination of 5 ng/ml Noggin, 5 ng/ml Dkk1, and 5 ng/ml IGF-1 affected the level of expression of eye field transcription factors in differentiated eye field progenitor cells at day 21. Among those conditions, inclusion of 50 ng/ml Noggin greatly induced the expression of eye field progenitor markers.

The RI medium composition included the following:
N2: 1% (1 ml of N2 per 100 ml media)
B27: 0.2% (0.2 ml of b27 per 100 ml)
Human insulin: 20 µg/ml (in addition to the 5 µg/ml insulin supplied by N2). The final concentration of insulin was 25 µg/ml.
Noggin: 50 ng/ml final concentration.

Figure 2A:
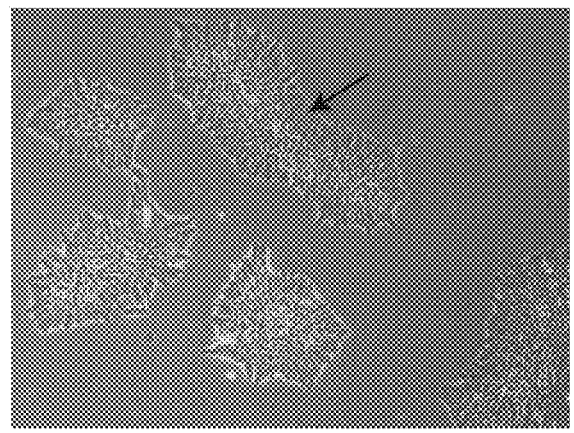
FIGS. 2A-C. Morphology of differentiating cells. (A) At day 1 after cell differentiation, cells at the colony margin were column-shaped (arrow). (B) At day 10 after differentiation, the edge cells became big and flat (arrow head) and the central cells were small and compact (arrow). (C) Rosette like structures formed at day 21.

Day 1-Day 4: A complete media change was done on every day. Though this frequency is preferred, it is thought that changing the medium less often, e.g., every 2-3 days, may be suitable particularly if a larger volume of media is used. Cell colonies continued to grow in the RI media with insulin and Noggin in the same concentrations as in the previous step. After 1 day exposure to RI media, cells located at the colony margin were elongated and column-shaped, as shown in FIG. 2A.

Day 5: Cell cultures became 80-90% confluent on day 5. Media was changed to neural differentiation (ND) medium: Neurobasal Medium (components listed in FIG. 21, Invitrogen) supplied with 4.5 g/L D-glucose, 100 unit/ml of penicillin, 100 µg/ml of streptomycin, 1× GlutaMAX™ (a stabilized form dipeptide from L-glutamine, L-alanyl-L-glutamine), 1% (or optionally 0.1 to 5%) N2 supplement (a chemically defined, serum-free supplement based on Bottenstein's N-1 formulation comprising 1 mM Human Transferrin (Holo), 0.0861 mM Insulin Recombinant Full Chain, 0.002 Progesterone, 10.01 mM Putrescine, and 0.00301 mM Selenite, Invitrogen), 2% (or optionally 0.05-2.0%) B27 supplement (components listed in FIG. 21), 0.1 mM MEM non-essential amino acids solution. Noggin was also added to the ND media at the final concentration of 50 ng/ml (or optionally 10-100 ng/ml).

Figure 2B:
Figure 2C:
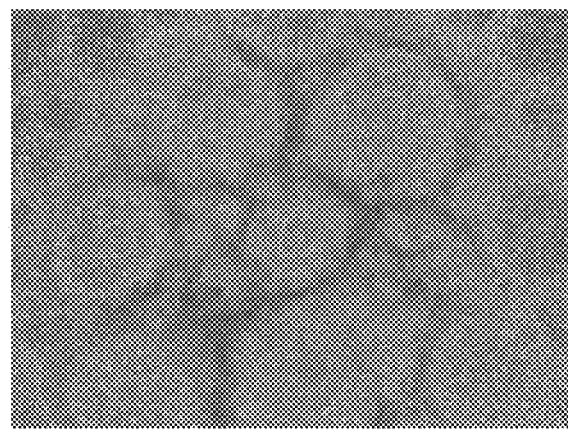
Figure 3A:
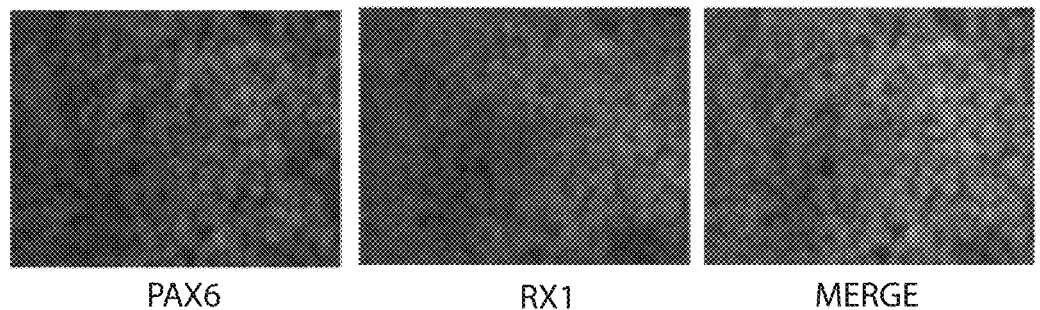
FIGS. 3A-E. Cells cultured at 21 days after initiation of differentiation expressed eye-field transcription factors. (A) Co-expression of PAX6 (green) and RX1 (red), as is apparent from the color version of the Figure. (B) 93% of cells co-expressed PAX6 and RX1 as shown by dual-color flow cytometric analysis. (C) Cells expressed Nestin (red) as is apparent from the color version of the Figure. (D) Cells expressed SOX2 (red) as is apparent from the color version of the Figure. In both (C) and (D), DAPI (blue) labels cell nuclei as is apparent from the color version of the Figure. (E) RT-PCR analysis of transcripts of eye field transcription factors: RX1, PAX6, LHX2, SIX3, SIX6, TBX3 and SOX2.
Figure 3B:
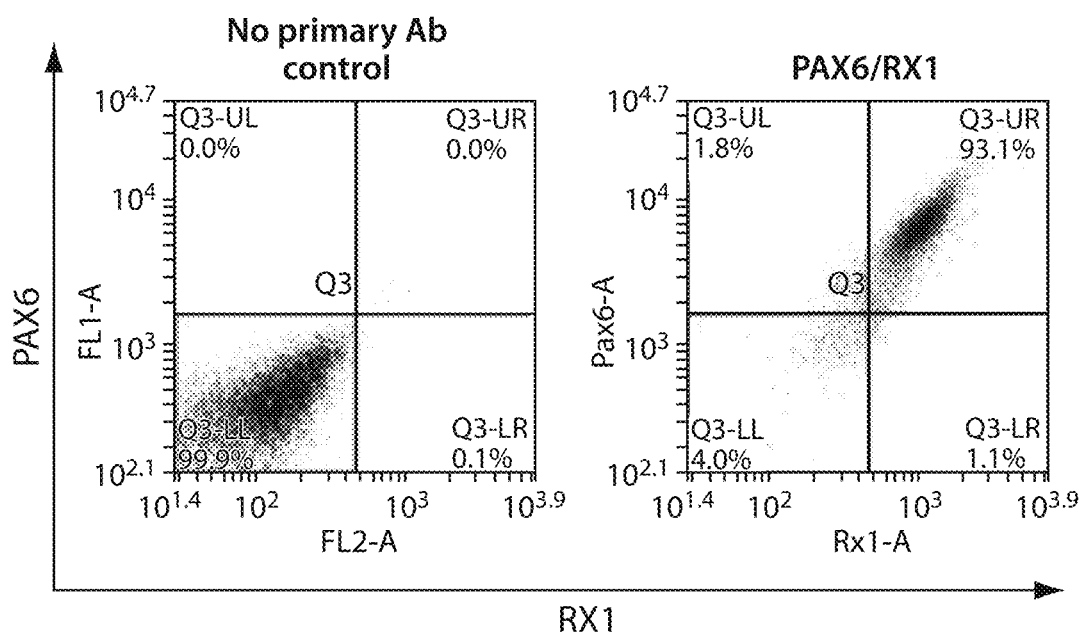
Figure 3C:
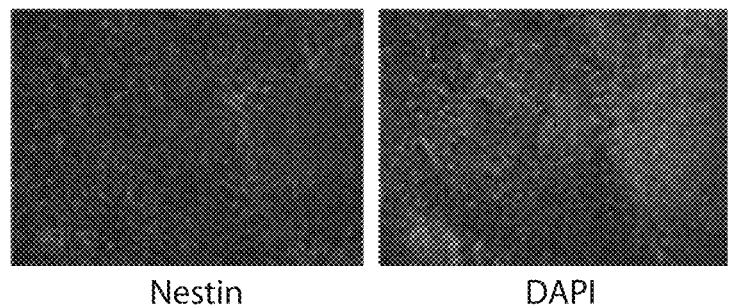
Figure 3D:
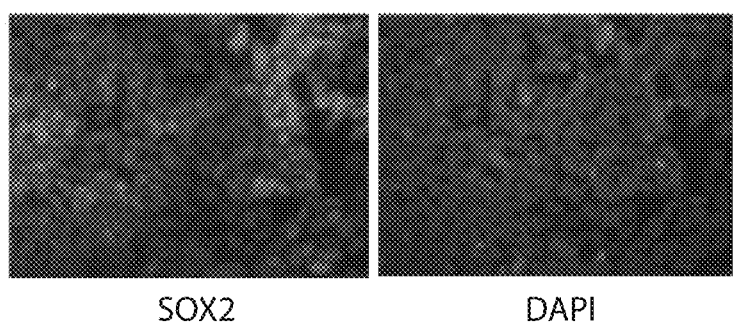
Figure 3E:
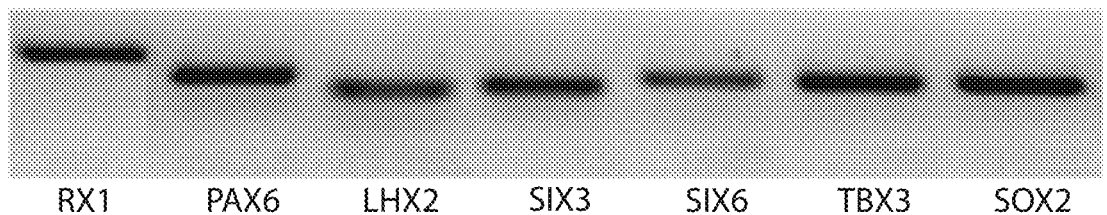

Day 6-Day 20: Cells were maintained in the ND medium. Half the amount of medium was changed every 2 days. Cell colonies continued to grow in the ND medium. The edge cells become flat and large, while the central cells were smaller and formed compact cell clusters (FIG. 2B). Around Day 14, cells located at the center of colonies began to form Rosette-like structures (FIG. 2C). At day 21, over 90% of the cells co-expressed PAX6 and RX1 (FIG. 3A-3B) as revealed by immunostaining and flow cytometry. By immunostaining, cells were positive for Nestin and SOX2 (FIG. 3C-3D). Cells were negative for an ES cell marker (specifically OCT4) and a retinal neural progenitor marker (specifically CHX10). By RT-PCR, cells expressed eye field transcription factors: PAX6, RX1, LHX2, SIX3, SIX6, TBX3 and SOX2 (FIG. 3E). These results indicate that the cells were eye-field progenitor cells.

The cells become eye field progenitors after they are cultured with neural differentiation media, from about day 7-8(about 2-3 days culture in ND media). At these time points detectable pax6/rx1 double positive cells arise. After about day 14 (between days 14-30), high purity (>90%) of eye field progenitor are generated.

Between about days 7-30 "Eye Field Progenitor Cells" or "EFPCs" are formed.

Day 21-Day 24: At Day 21, cells were lifted off from the growth surface and mechanically fragmented into clusters in ND medium without Noggin. Cell clusters were transferred to 100 mm ultra-low attachment culture dishes. Cell clusters rounded up and formed individual spheres (solid clusters) in the suspension culture. At Day 23, half of the culture medium was replaced.

Figure 4A:
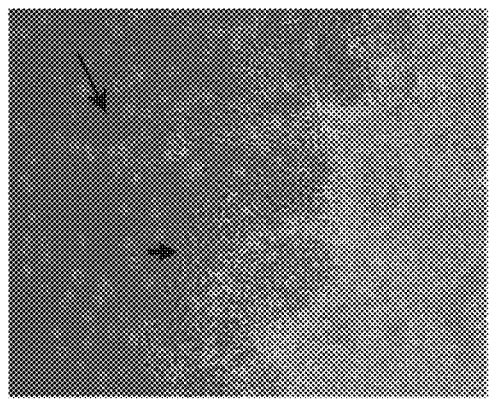
FIGS. 4A-C. Cells cultured at 30 days after initiation of differentiation expressed retinal neural progenitor markers. (A) Morphology of cells. After plating on Matrigel™, neurons migrated out from cell aggregates (arrow). A few epithelial-like cells (arrow head) are observed around cell aggregates. (B) Upper panel, phase contrast image of migrating neurons; Lower panel, migrating neurons expressed Tuj1 (red) as is apparent from the color version of the Figure. (C) Cells co-expressed PAX6 (red) and CHX10 (green), as is apparent from the color version of the Figure.

At Day 25, spheres were collected and dead cells and debris were removed by washing the spheres with the ND media. Cell spheres were plated onto Matrigel™ coated glass chamber slide (for immunostaining) or tissue culture dishes in the ND medium. Spheres attached within 12 hours. They continued to grow and show neuronal phenotypes, specifically exhibiting cell aggregates within the spheres that extended axon-like neurites with some cells migrating out from aggregates (FIG. 4A). There were few big epithelial-like cells which could be eliminated during cell passage (see "Month 2-Month 3" below). The cultures were maintained with half of the culture medium changed every two days until the cell cultures become confluent It was observed that balls of spheres attached to the plate.

Figure 4B:
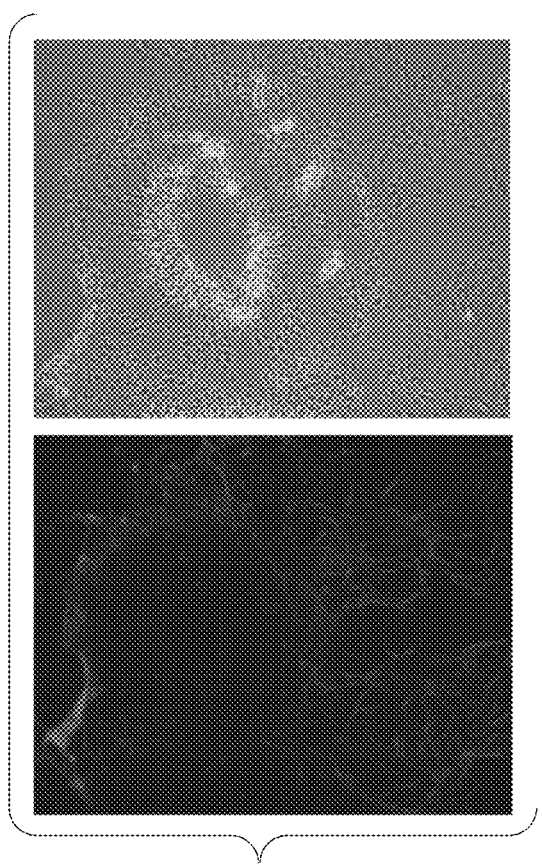
Figure 4C:
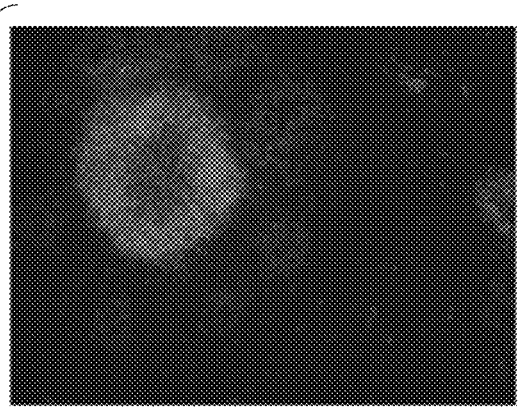
Figure 4C:
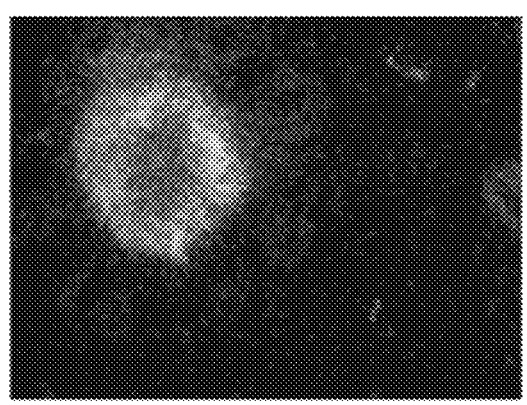
Figure 4C:
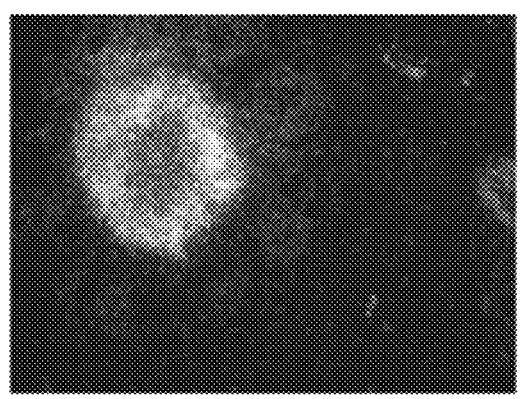

At Day 30, the migrating cells were positive for Tuj1, which labels immature and mature neurons (FIG. 4B). Cells in the aggregates were negative for Tuj1. Over 95% cells (including cells in the aggregates or migrating out from aggregates) co-expressed PAX6 and CHX10 suggesting that they had become retinal neural progenitors (FIG. 4C).

Month 2-Month 3: Growth and passaging cells in the ND media. The cells from the previous step were passaged when they became confluent. A two-step successive passaging technique was used to produce high-purity neural cultures by eliminating the majority of non-neuronal phenotype cells. The first step: neural sphere culture. Cells were enzymatically (e.g., using Accutase) or mechanically dissociated into a mixture of single cells and cell clusters. Cells were transferred to ultra-low attachment dishes in ND medium. All cells with neuronal phenotype form neural spheres in the suspension culture. On day 3, half of the medium was changed and the cells were maintained until day 5. The second step: adherent culture. Neural spheres were collected on day 5 and dead cells and debris were removed by washing the spheres with ND medium. Spheres were plated on Matrigel™-coated tissue culture dishes until confluent. The first and second steps were alternated and the cells were so maintained until the end of the third month.

Figure 5A:
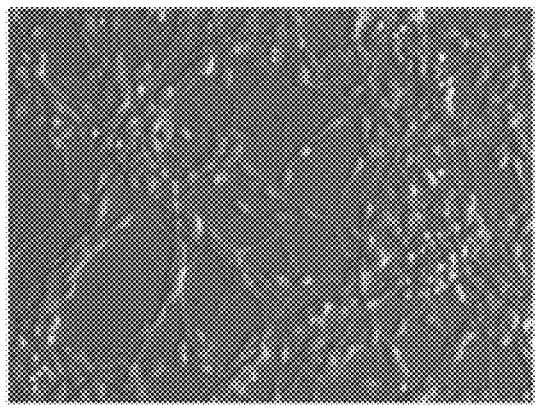
FIGS. 5A-D. Cells cultured at 3 months after initiation of differentiation. (A) Morphology of cells. (B) Cells express PAX6 but not CHX10, as is apparent from the color version of the Figure which shows red staining of some of the cells but no green staining. (C) The expression of Recoverin was restricted to the cytoplasm of the cell body, as is apparent from the color version of the Figure. (D), Real-time RT-PCT analysis of transcripts of Rhodopsin, Opsin, and Recoverin in retinal neural progenitors (RNPs) and photoreceptor progenitor cells (indicated as PhRPs).
Figure 5B:
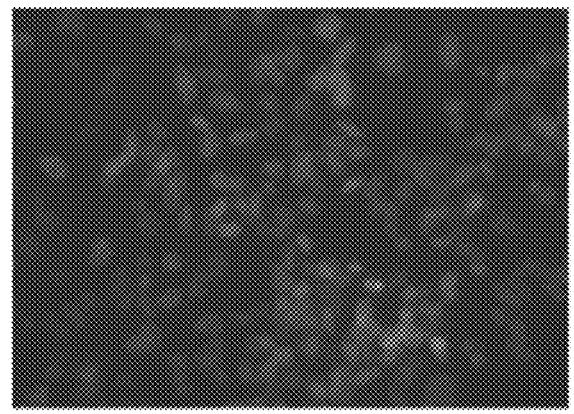
Figure 5C:
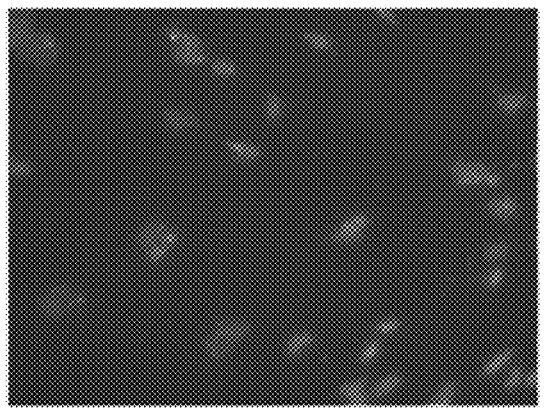
Figure 5D:
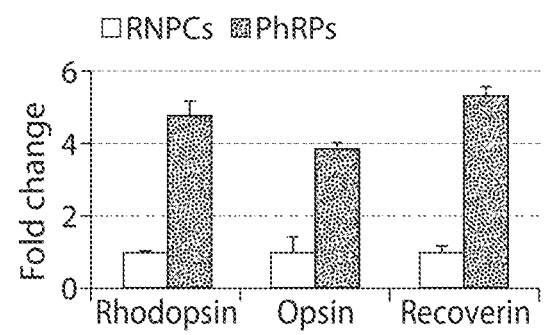
Figure 6A:
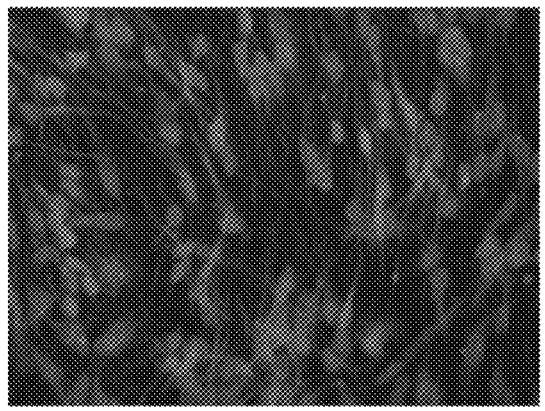
FIGS. 6A-D. Differentiated cells express photoreceptor cell markers. Cells expressed (A) Rhodopsin (red), (B) Rhodopsin (red) and Recoverin (green), (C) Opsin (green), and (D) phosphodiesterase 6A alpha subunit (PDE6a) (red). DAPI (blue) labels cell nuclei. Expression of these markers is apparent from the color version of the Figure.
Figure 6B:
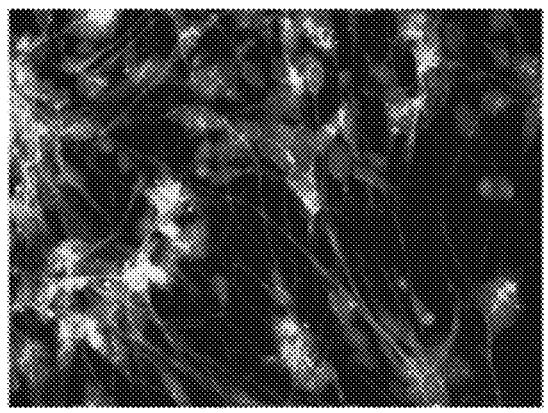
Figure 6C:
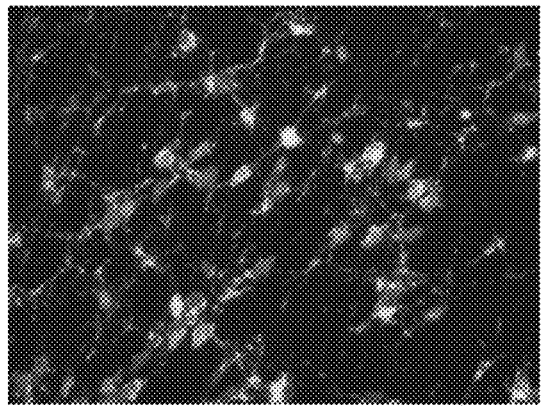
Figure 6D:
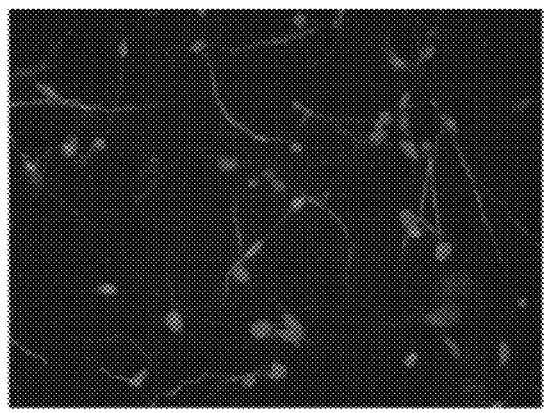

At the end of the 3rd month, the cells showed neural phenotype. Specifically, the cells formed neurites in culture (FIG. 5A). They were capable of proliferation. They expressed PAX6 but were negative for CHX10 as assessed by immunostaining (FIG. 5B). By immunostaining, the cells were positive for Recoverin, which was expressed in the cytoplasm of the cell body (FIG. 5C). The cells also expressed Rhodopsin, Opsin and Recoverin mRNA (FIG. 5D). Real-time PCR analyses revealed that the expressions of transcription factors controlling rod and/or cone photoreceptor differentiation are highly expressed (Table 1). These results indicate that the cells were photoreceptor progenitors. Additionally, at this time-point it was through based on observations that all or essentially all of the cells in the culture are photoreceptor progenitors.

TABLE 1

Quantitative RT-PCT analyses of transcription factors controlling photoreceptor differentiation and regeneration.

| Transcription Factors | Rod/Cone | Fold change (vs. ESC) |
|---|---|---|
| TRβ2 | Cone | 3.5-5 |
| NR2E3 | Rod | 7-11 |
| NRL | Rod | 4-8 |

TABLE 1-continued

Quantitative RT-PCT analyses of transcription factors controlling photoreceptor differentiation and regeneration.

| Transcription Factors | Rod/Cone | Fold change (vs. ESC) |
|---|---|---|
| MASH1 | Rod | 1000-1200 |
| CRX | Rod, Cone | — |
| RORβ | Rod, Cone | 40-60 |
| OTX2 | Rod, Cone | — |

Month 4-Month 9/or longer: In vitro expansion of photoreceptor progenitors. In some experiments the cells were further expanded using the two-step successive passaging technique described above ("Month 2-Month 3"). However, it was observed that over time the cells lose their capability to differentiate into cone photoreceptors (though they retain the ability to differentiate into rod photoreceptors). Specifically, after photoreceptor progenitors were maintained by the two-step successive passaging technique for 9 months in culture and then induced to differentiate, they only produced cells that expressed rod photoreceptor markers and not cells that expressed cone photoreceptor markers. This property could potentially be put to advantageous use, as progenitor cells that preferentially produce rod photoreceptors may be useful in the treatment of diseases wherein rod formation is desirable, or as a reagent for the study of factors involved in photoreceptor progenitor fate determination.

Example 2: Differentiation of Photoreceptor Progenitor Cells: Cell Treatment with Retinoic Acid and Taurine Attached photoreceptor progenitors were treated with retinoic acid in the following conditions for two weeks: ND medium supplied with 2 µM (or optionally 0.2-10 µM) retinoic acid and 100 µM (or optionally 20-500 µM) taurine. Half of the culture medium was changed every 2 days.

Differentiate cells in Photoreceptor differentiation media: The medium was changed to Photoreceptor Differentiation Medium comprising Neurobasal Medium (Invitrogen) supplied with 4.5 g/L D-glucose, 100 unit/ml of penicillin, 100 µg/ml of streptomycin, 1× GlutaMAX™, 1% N2 supplement (Invitrogen), 2% B27 supplement (formula number 080085-SA), with the addition of 5 µM (or optionally 1-100 µM) Forskolin, 10 ng/ml (or optionally 1-100 ng/ml) BDNF, 10 ng/ml (or optionally 1-100 ng/ml) CNTF, 10 ng/ml (or optionally 5-50 ng/ml) LIF and 10 µM (or optionally 1-100 µM) DAPT. Half of the medium was changed every 2 days. Specifically the amounts of each factor were as follows: Forskolin (5 µM), BDNF (10 ng/ml), CNTF (10 ng/ml), LIF (10 ng/ml) and DAPT (10 µM). LIF was determined not to be necessary and can be left out.

At two weeks after initiating cell differentiation, the expressions of Rhodopsin, Opsin (green/red), Recoverin and phosphodiesterase 6A alpha subunit (PDE6a) were detected in the cytoplasm of the cell body and neurites (FIG. 6A-6D). These gene expression results indicate that these are photoreceptor cells.

Example 3: Cryopreservation of Human ESC-Derived Retinal Neural Progenitors

Retinal neural progenitors of the invention, photoreceptor progenitors of the invention and retinoic acid treated photoreceptor progenitors of the invention can be frozen down in an animal-free cryopreservation buffer, such as Cryostor CS10, or another cryopreservation buffer such as 90% FBS and 10% DMSO. With respect to the photoreceptor progenitors, it was observed that freezing cells as neurospheres was beneficial, which may be due to the benefits of cell-cell contact. Preferably the neurospheres were frozen down at a size that was not too large, such as 50-250 cells.

Example 4: Animal Studies in Stargardt Macular Dystrophy Animal Model

Figure 7:
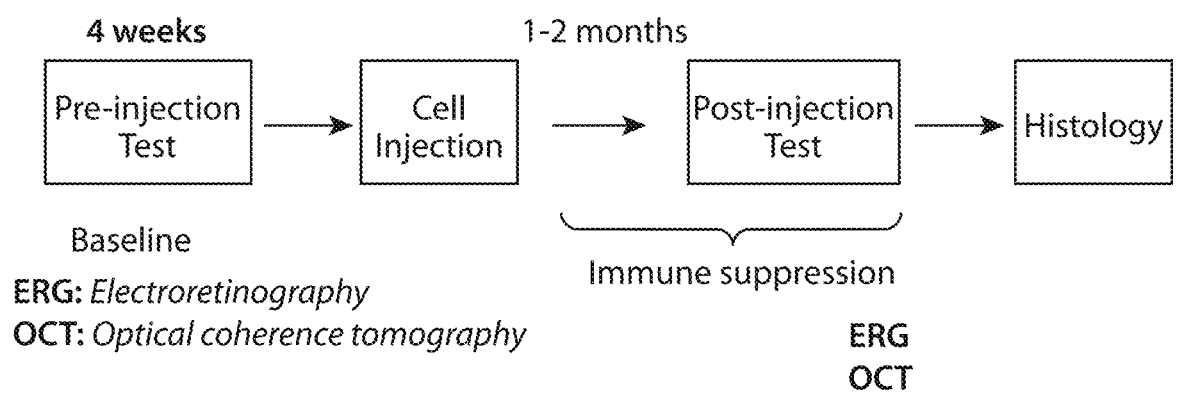
FIG. 7. Schematic diagram of animal studies in ELOVL4-transgenic mice.

Animal studies were carried out in a Stargardt macular dystrophy animal model, ELOVL4 transgenic 2 (TG2) mice (FIG. 7).

Photoreceptor progenitors (produced as described in in Example 1) and separately, retinoic acid and taurine treated photoreceptor progenitors (i.e., immature photoreceptor cells, produced as described in Example 2) were dissociated into single cells using Accutase. Cells were re-suspended in PBS buffer.

28 days-old TG2 mice received an injection of 1 µl of cell suspension containing $5 \times 10^5$ cells into the subretinal space or 150 µl of cell suspension containing $1 \times 10^6$ cells into the tail vein. All mice underwent baseline ERG and OCT tests before cell injection.

Mice were fed with water supplied with Cyclosporin A (USP modified).

Figure 8:
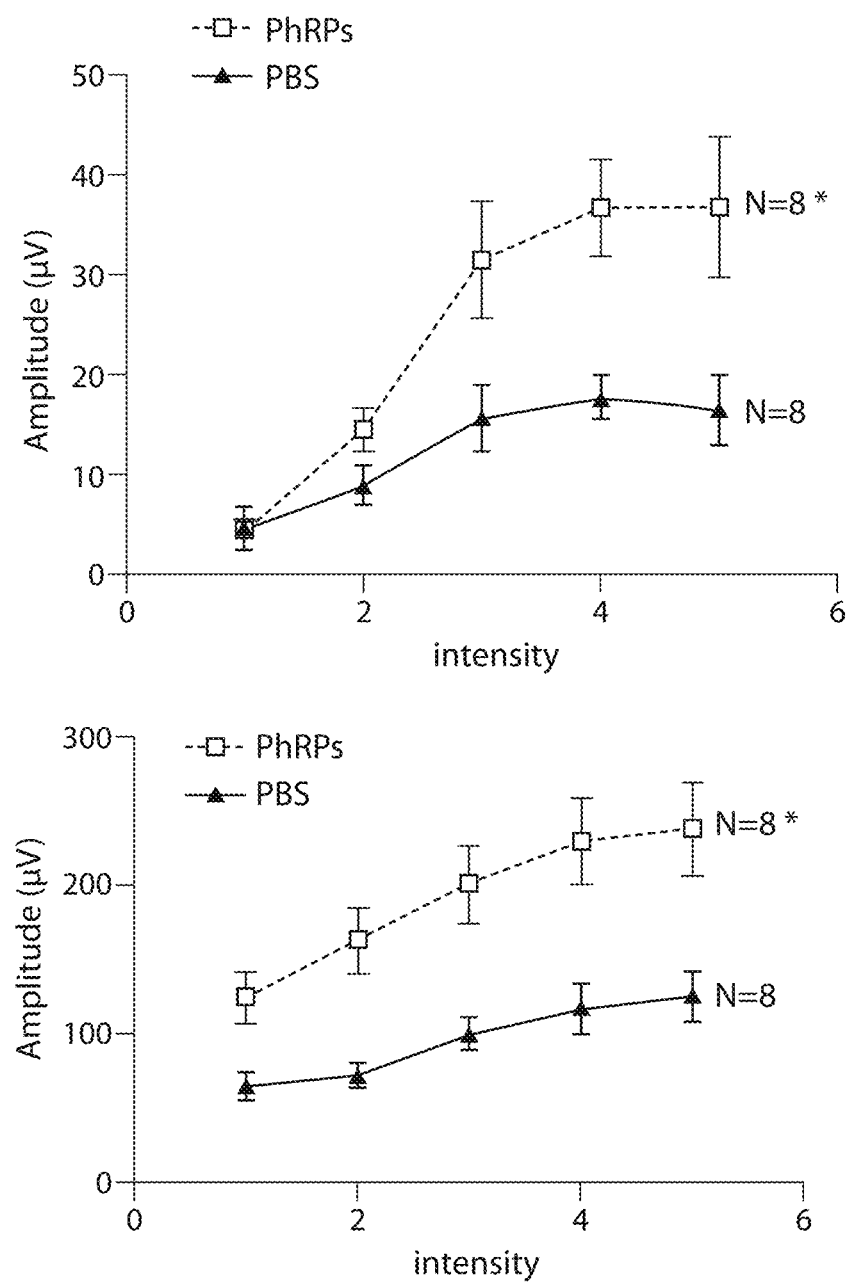
FIG. 8: Scotopic ERG intensity-response function recorded at one month after subretinal cell injection. Stimulus intensity curves for scotopic a-waves (upper panel) and b-waves (lower panel) from ELOVL4-TG2 mice administered PBS (black line) or photoreceptor progenitor cells (indicated as PhRPs, grey line). *, $p<0.001$ (vs. PBS).
Figure 9:
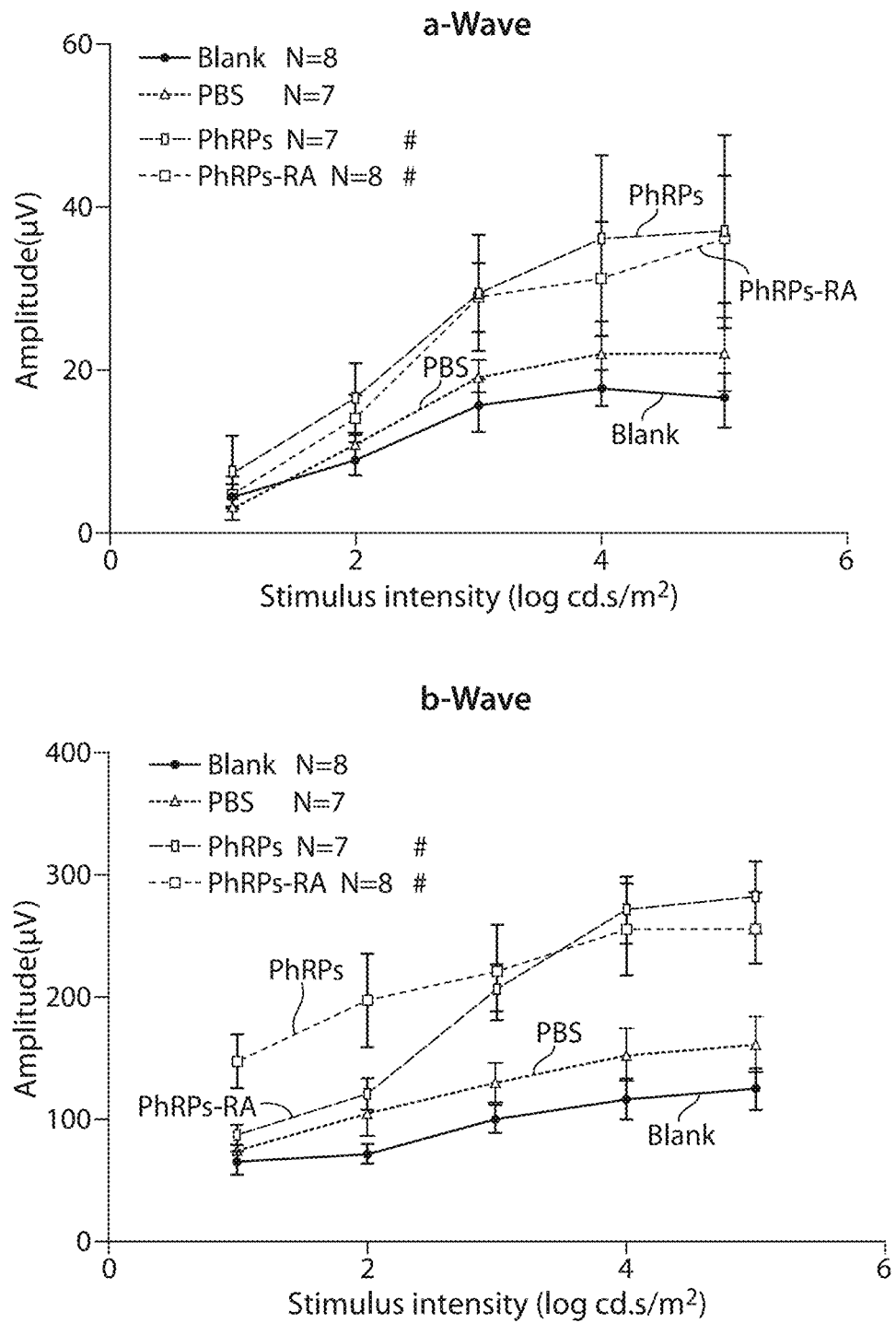
FIG. 9. Scotopic ERG intensity-response function recorded at one month after systemic cell injection. Stimulus intensity curves for scotopic a-waves (upper panel) and b-waves (lower panel) from ELOVL4-TG2 mice administered PBS, photoreceptor progenitor cells (indicated as PhRPs) or retinoic acid treated photoreceptor progenitor cells (PhRPs-RA). Blank represents untreated mice. #, $p<0.01$ (vs. PBS).

At one month after cell injection, mice that received a subretinal injection of photoreceptor progenitors showed a significant improvement of the rod photoreceptor function revealed by a significant increase of the scotopic ERG amplitude of both the a- and b-wave (FIG. 8). Mice that received a tail vein injection of photoreceptor progenitors and retinoic acid and taurine-treated photoreceptor progenitors showed a significant improvement of the Rod photoreceptor function revealed by a significant increase of the scotopic ERG amplitude of both a- and b-wave (FIG. 9).

Figure 10A:
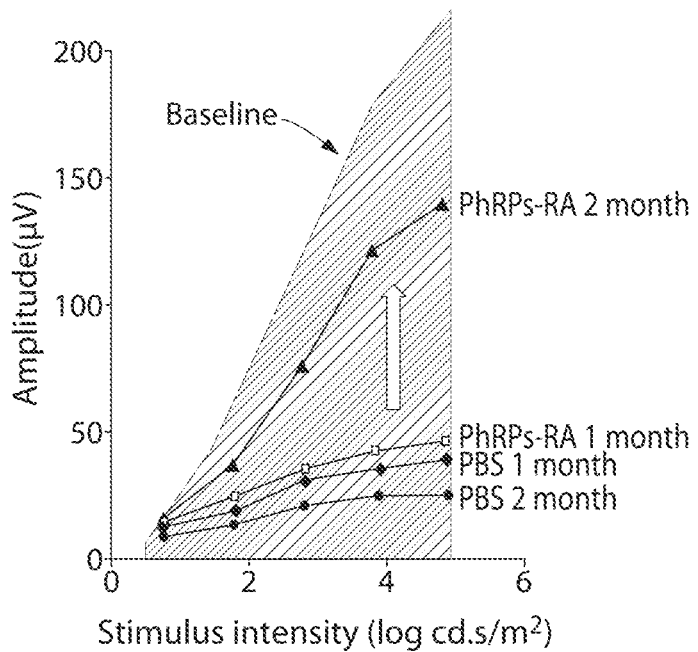
FIGS. 10A-B. Photoreceptor progenitor cell systemic injection restores rod function between one month and two months after cell transplantation. Scotopic ERG amplitude of a-waves (A) and b-waves (B) at one and two month after cell injection from ELOVL4-TG2 mice administered PBS (PBS) or retinoic acid treated photoreceptor progenitor cells (PhRPs-RA).
Figure 10B:
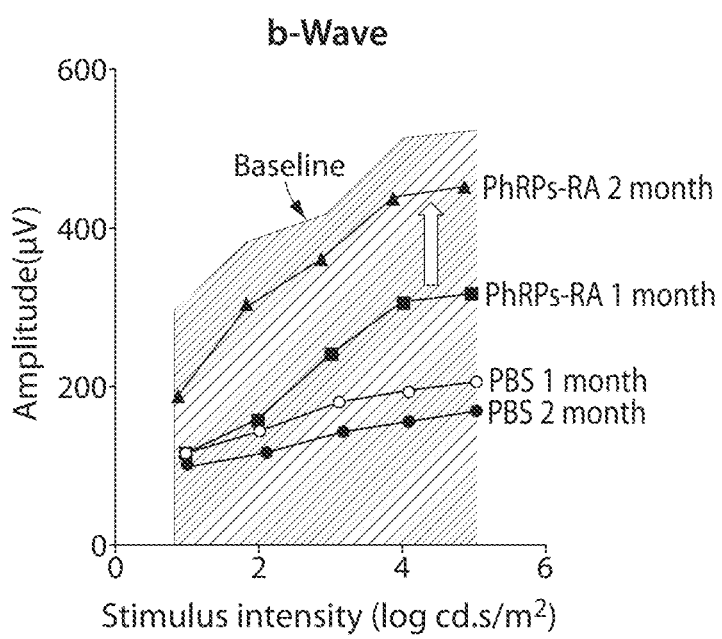
Figure 10C:
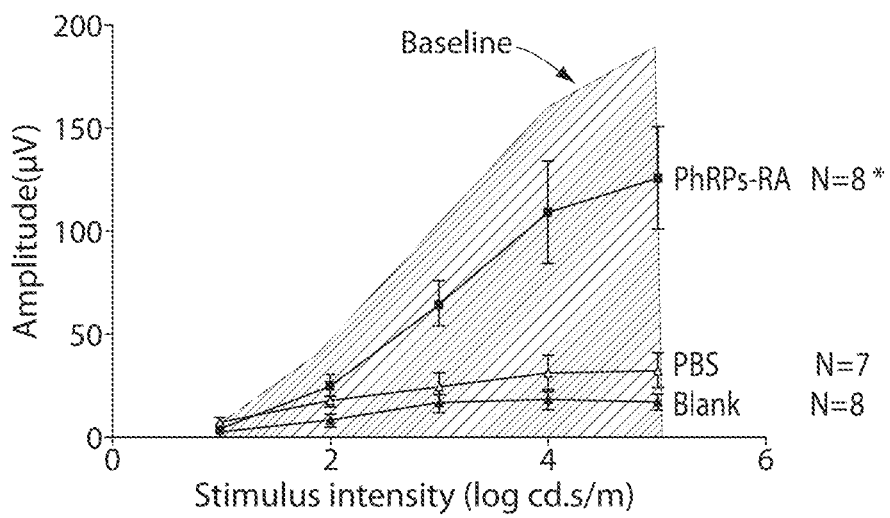
FIG. 10C. Scotopic ERG intensity-response function recorded at two months after systemic cell injection. Stimulus intensity curves for scotopic a-waves (upper panel) and b-waves (lower panel) from ELOVL4-TG2 mice administered PBS or retinoic acid treated photoreceptor progenitor cells (PhRPs-RA). Blank represents untreated mice. Baseline is the level recorded at 4 weeks. *, $p<0.001$ (vs. PBS).
Figure 10C:
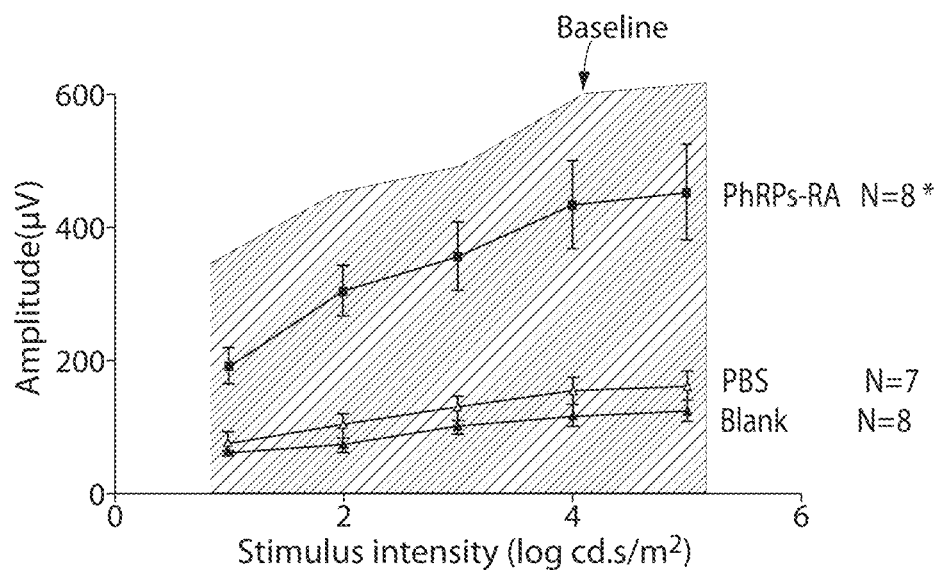
Figure 11:
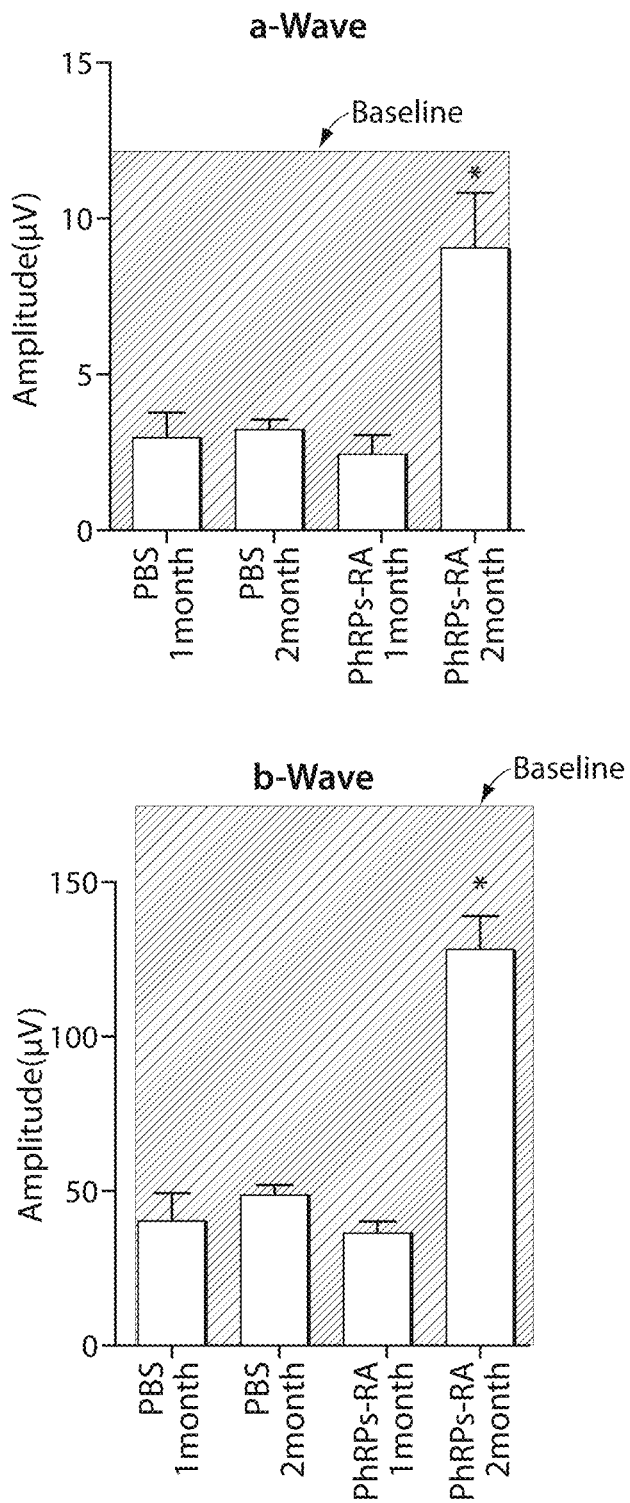
FIG. 11. Photopic ERG amplitude of a-waves (upper panel) and b-waves (lower panel) at one and two month after cell injection from ELOVL4-TG2 mice administered with PBS or retinoic acid treated Photoreceptor progenitors (PhRPs-RA). *, p<0.001 (vs. PBS 2 month).

At two months after cell injection, mice that received a tail vein injection of retinoic acid treated photoreceptor progenitors showed a further improvement of the rod photoreceptor function revealed by a further increase of the amplitude of both a- and b-wave of scotopic ERG responsive curve (FIG. 10A-10C). The function of cone photoreceptors was significantly improved as revealed by a significant increase of the photopic ERG amplitude of both a- and b-wave (FIG. 11).

Figure 12:
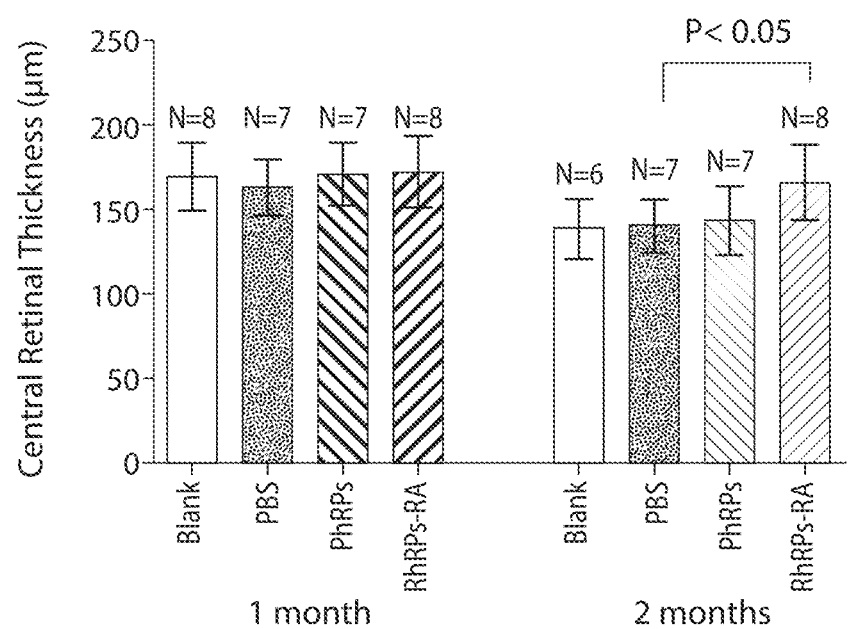
FIG. 12. Whole central retina thickness measured by OCT at one and two months after cell injection from untreated ELOVL4-TG2 mice (blank) and mice administered PBS, photoreceptor progenitor cells (PhRPs), or retinoic acid treated photoreceptor progenitor cells (PhRPs-RA).

At two months after injection, mice that received a tail vein injection of immature photoreceptor cells treated with retinoic acid and taurine showed a significant increase of whole retina thickness revealed by OCT (FIG. 12).

Figure 13A:
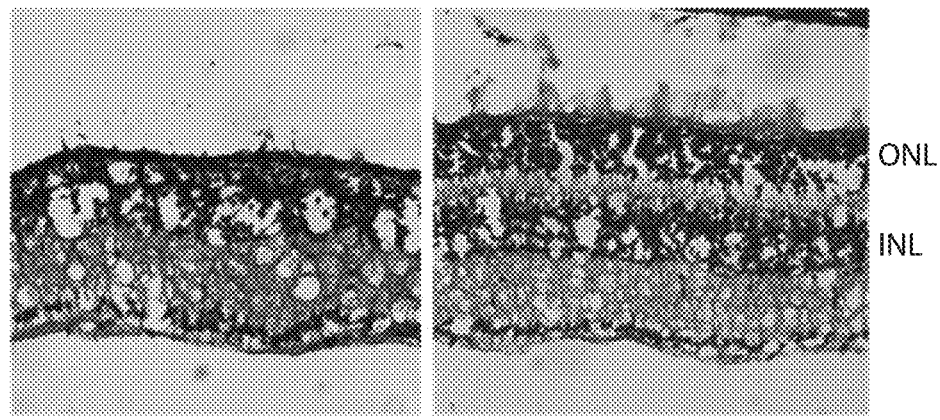
FIGS. 13A-B. (A) Representative images of retina HE staining at two months after cell injection from ELOVL4-TG2 mice administered PBS (Left panel) and retinoic acid treated photoreceptor progenitor cells (Right panel). ONL, outer nuclear layer. INL, internal nuclear layer. (B), Quantification of the thickness of ONL of retina at two month after cell injection from untreated ELOVL4-TG2 mice (blank) and mice administered PBS or retinoic acid treated Photoreceptor progenitors (PhRPs-RA).
Figure 13B:
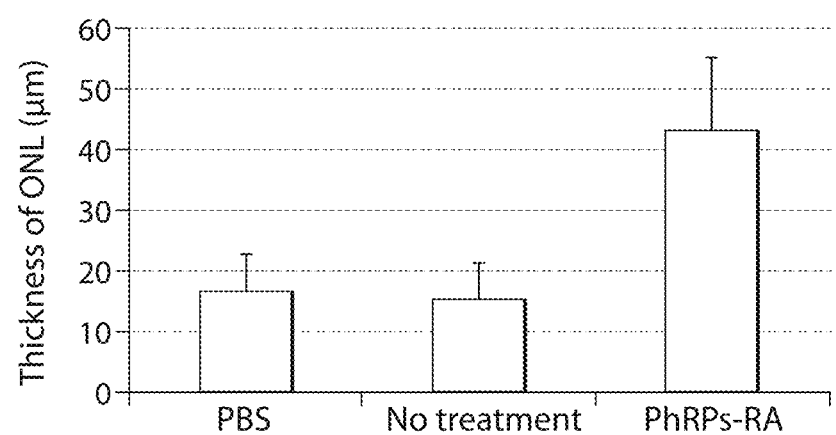
Figure 14:
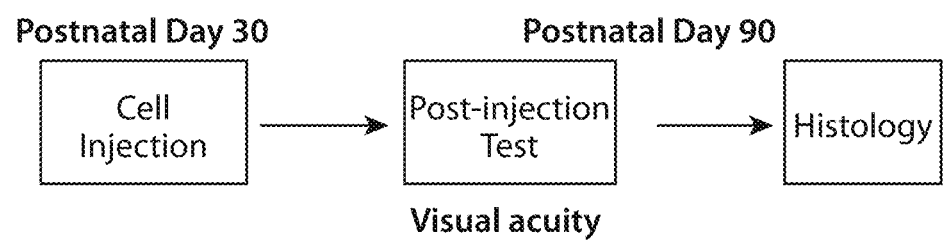
FIG. 14. Schematic diagram of animal studies in RCS rats.

At two months after cell transplantation, there was a significant preservation of photoreceptor neurons in the ONL of retina in mice that received retinoic acid and taurine-treated photoreceptor progenitors (FIG. 13).

Example 5: Animal Models of Achromatopsia (Color Blindness) and Improving Night Vision Cells produced according to the methods described in Example 1 or Example 2 are tested in mouse, sheep, and/or dog models of Achromatopsia (color blindness). The following models are used:

Mouse: (1) the cpfl5 mouse: a naturally occurring mouse model of achromatopsia with a CNGA3 mutation; (2) CNGA3 knockout mice; (3) GNAT2cpfl3 mice: mutation related to GNAT2; (4) PDE6C-cpfl1: mutation related to pde6c.

Sheep: Awassi sheep lambs: mutation in CNGA3

Dog: Two natural occurring canines for mutation in CNGA3 have been identified: the autosomal recessive canine cone degeneration in the Alaskan malamute and the German shorthaired pointer.

Photoreceptor progenitors (produced as described in Example 1) are dissociated into single cells using accutase. Cells and are re-suspended in PBS buffer. The animals receive injections of $2\times10^5$ cells or more into the vitreous cavity or $5\times10^6$ cells or more into a tail vein (e.g., the tail vein). Control animals receive an injection with PBS buffer. After one or two months or at other time points, the animals are given optomotor responsiveness tests to check visual function in order to detect possible improvements thereto. Additionally, histological analysis is performed to determine whether there is any significant preservation of photoreceptor neurons or growth of photoreceptor neurons, and additionally to detect whether cells transplanted into the vitreous cavity showed good survival after injection, and whether the cells differentiated into rod or cone photoreceptor cells expressing markers thereof.

Example 6: Animal Studies in a Photoreceptor Degeneration Rat Model, Royal College of Surgeons (RCS) Rat Photoreceptor progenitors (produced as described in Example 1) were dissociated into single cells using accutase. Cells were re-suspended in PBS buffer.

On postnatal day 30, RCS rats received injections of $2\times10^5$ cells into the vitreous cavity or $5\times10^6$ cells into the tail vein. Control rats received an injection with PBS buffer.

RCS rats were fed with water supplied with Cyclosporin A (USP modified).

At one month and two months after cell injection, rats were given optomotor responsive tests to check visual function. There was no significant improvement in visual function in treated rats (data not shown).

The resulting effect on visual function may be detected by the Optomotor response test, ERG, luminance threshold recording and/or visual center blood flow assay.

Figure 15A:
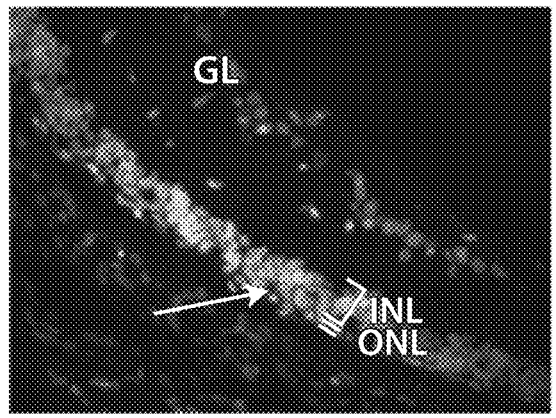
FIGS. 15A-C. Preservation of host photoreceptor cells after transplantation of human ES cell-derived photoreceptor progenitor cells. Retinal sections at P90 stained with DAPI: (A) Outer nuclear layer (ONL) is reduced to 0-1 layer in control rats. (B) Rescued ONL cells in RCS rat after intravenous cell injection, which is 2-4 cells deep. (C) Rescued ONL cells in RCS rat receiving intravitreal cell injection, which is 3-5 cells deep. INL, inner nuclear layer; GL, ganglion cell layer.
Figure 15B:
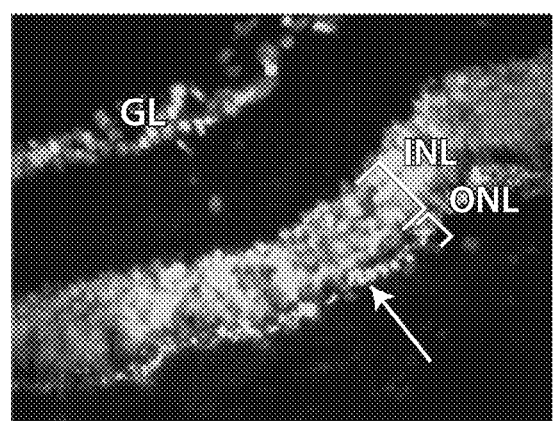
Figure 15C:
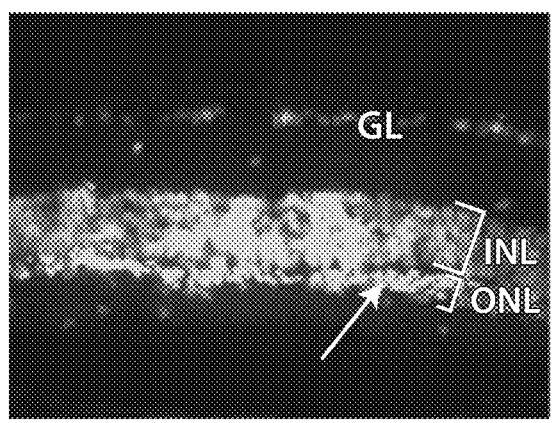

At two months after cell injection, Histology revealed a significant preservation of photoreceptor neurons in the ONL of retina in RCS rats administered with cell treatment (FIG. 15).

Figure 16A:
FIGS. 16A-C. Preservation of host rod photoreceptor cell outer segment (OS) after transplantation of human ES cell-derived photoreceptor progenitor cells. Retinal sections at P90 stained for Rhodopsin (green). (A) Complete loss of rod OS in control rats (arrow). (B) Expression of Rhodopsin in the OS of host rod photoreceptor cells in RCS rat retina after intravenous injection of photoreceptor progenitor cells (arrow). (C) Expression of Rhodopsin in the OS of host rod photoreceptor cells in RCS rat retina after intravitreal transplantation of photoreceptor progenitor cells (arrow). Expression of Rhodopsin is apparent in the color version of the Figure.
Figure 16B:
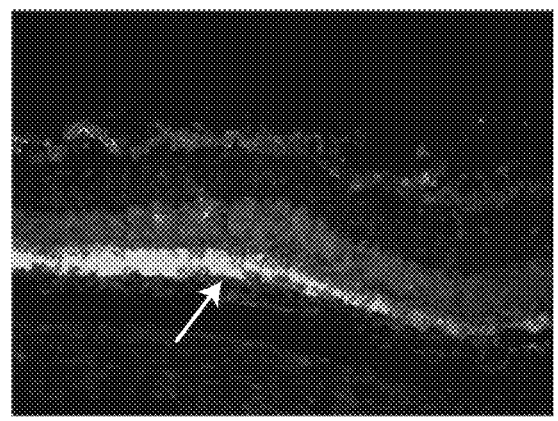
Figure 16C:
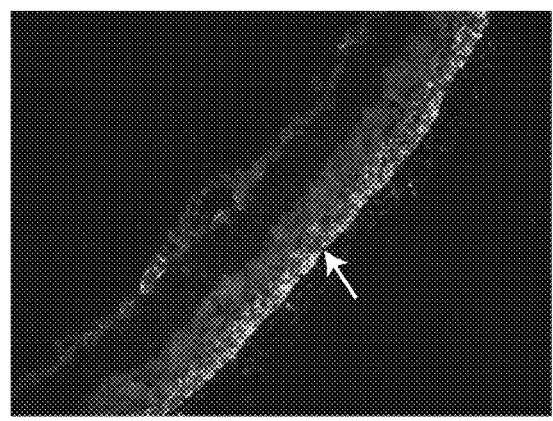
Figure 17A:
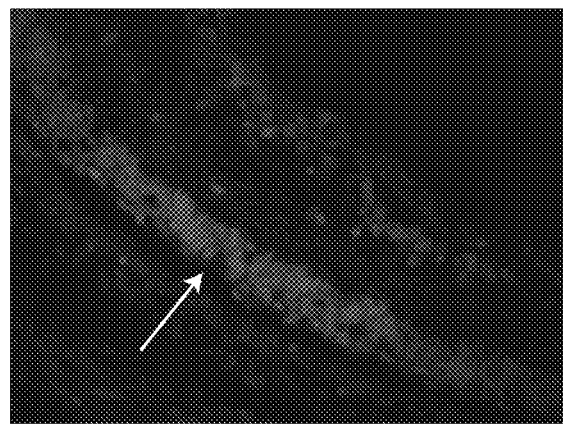
FIGS. 17A-C. Preservation of host cone photoreceptor cell outer segment (OS) after transplantation of human ES cell-derived photoreceptor progenitor cells. Retinal sections at P90 stained for Opsin (green). (A) Complete loss of cone OS in control rats (arrow). (B) Expression of Opsin in the OS of host cone photoreceptor cells in RCS rat retina after intravenous injection of photoreceptor progenitor cells (arrow). (C) Expression of Opsin in the OS of host cone photoreceptor cells in RCS rat retina after intravitreal transplantation of photoreceptor progenitors (arrow). Expression of Opsin is apparent in the color version of the Figure.
Figure 17B:
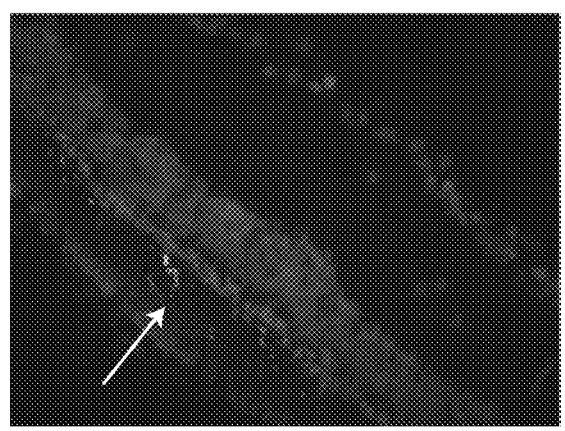
Figure 17C:
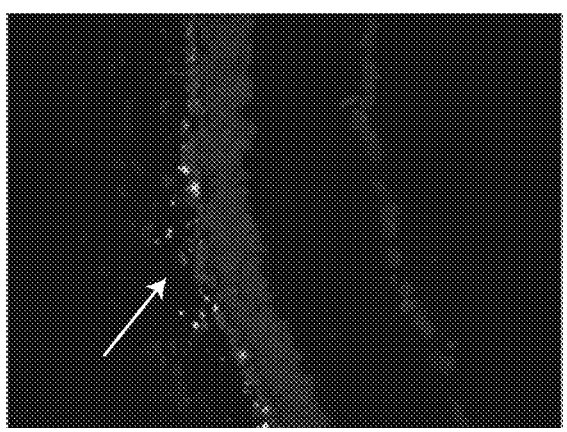

Preservation of rod and cone photoreceptor outer segment revealed by immunostaining of Rhodopsin (rod) and Opsin (cone) was observed in cell treated groups (both intravitreal and tail vein injection, FIG. 16 and FIG. 17).

Figure 18A:
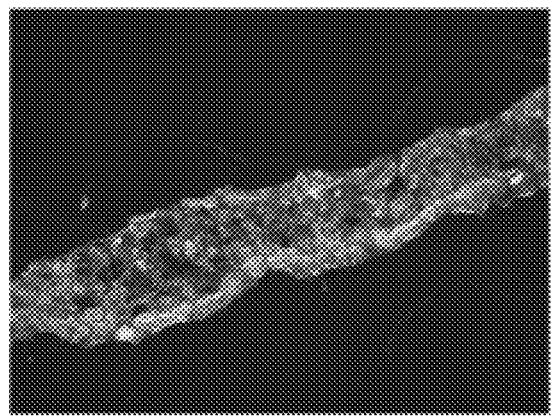
FIGS. 18A-B. Human ES cell-derived photoreceptor progenitor cells transplanted into the vitreous of RCS rats differentiated into mature rod photoreceptor cells. Retinal sections at P90 stained for rhodopsin (green in A), Recoverin (green in B). Human cells were labeled with anti-HuNU antibody (red). DAPI labeled all nuclei. Expression of rhodopsin and recoverin and staining with DAPI is apparent in the color version of the Figure.
Figure 18B:
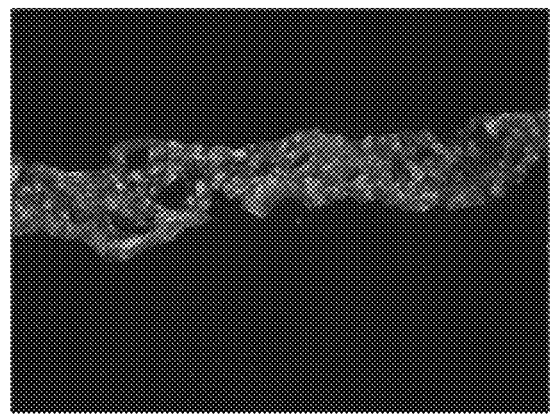

Cells transplanted into the vitreous cavity showed good survival at 2 months after injection, then further differentiated into rod photoreceptor cells expressing rod photoreceptor markers (FIG. 18).

Figure 28:
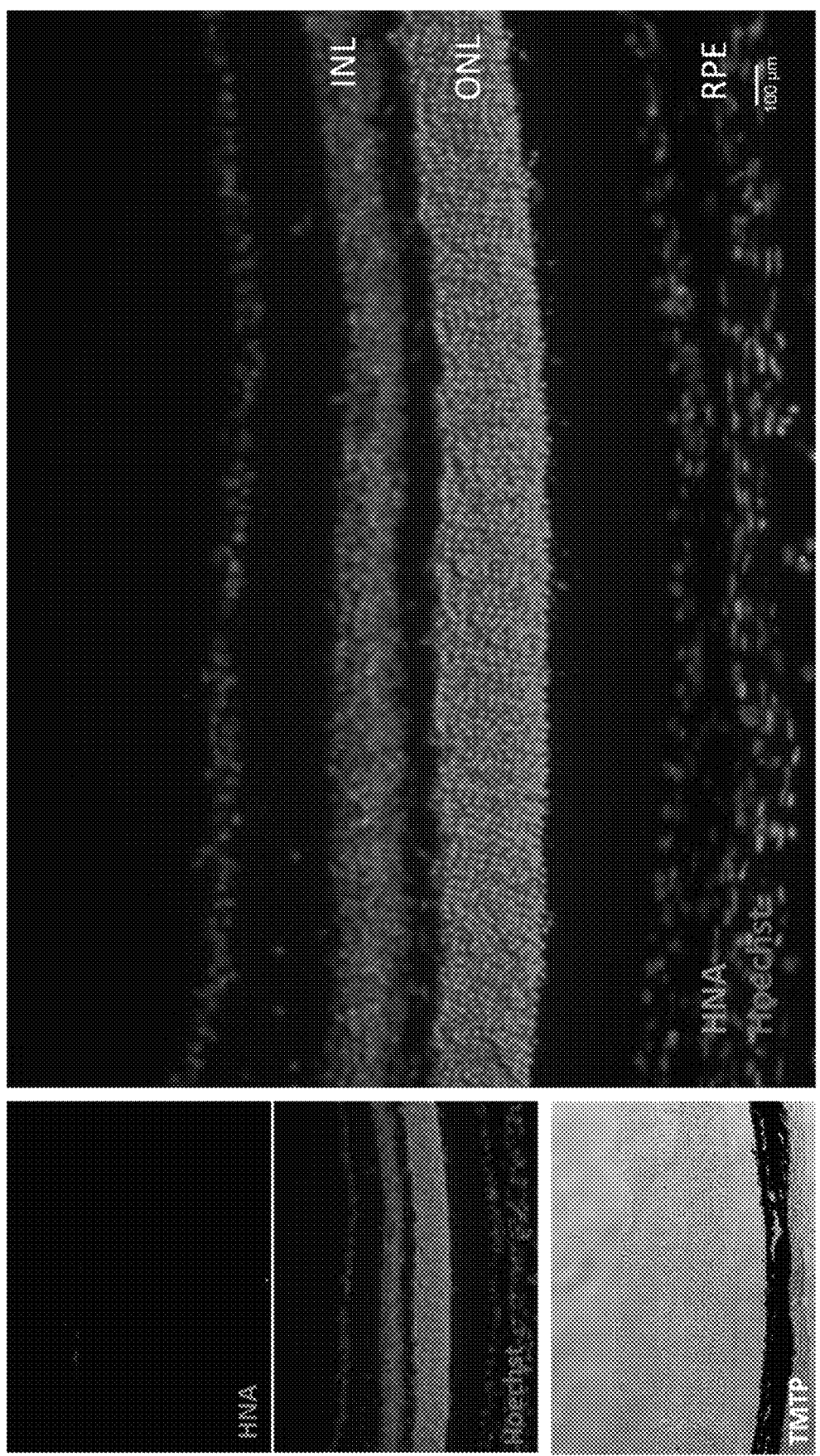
FIG. 28 provides cross-sectional images of the retina, including the INL, ONL and RPE, of control eyes in wild type mice (that did not receive a cell transplantation). The side panels show staining with HNA and Hoechst, and a TMTP image. No HNA staining is observable.

Example 7: Survival, Integration and Migration of hESC Cell Derived Photoreceptor Progenitor Cells in Wild Type Mice Donor cells are H9 hESC-derived photoreceptor progenitors. Cells were generated according to the methods described herein. Host mice were adult (age >8 weeks) WT mice (strain C57/B16) (N=18 mice). In each mouse, one eye was injected subretinally with donor cells, while the other eye acted as a non-transplant control. Specimens were collected for histology at 1, 2 and 3 weeks post injection (N=6 at each time point). For histology, tissue was placed upon an Isopore™ polycarbonate membrane (Millipore, TMTP) and bright field microscopy was used for imaging. Successful recovery of 5 million cells from 1 vial (>95% cells viable by trypan blue assay) was observed. These cells formed neural spheres post-thaw. H9 hESC-derived photoreceptor progenitor donor cells survival was observed at 1, 2 and 3 weeks post-transplant. Donor cells were observed in the subretinal space at 1 and 2 weeks post-transplant. Their migration towards the outer nuclear layer (ONL) of the retina was evident at 3 weeks, and integration into the ONL was also was observed at 3 weeks post-transplant (see FIGS. 24-27). Cross-sectional images of control eyes are shown in FIG. 28.

Example 8: Animal Studies in Rd1 Mouse Model: Transplantation of hESC and hiPSC Derived Photoreceptor Progenitors in Rd1 Mice Cell Preparation. Cells were transfected in vitro, using a Rhodopsin Kinase GFP+ mutant AAV2 viral vector in order to enhance detection of transplanted cells in morphology assessment.

Recovery, transfection and dissociation timeline. At 0 hrs, cells were thawed and cultured; at 24 hrs, cells were transfected with AAV2 Y444F RHOKpr.GFP; at 48 hrs, neural spheres were generated; at 72 hrs, cells were transplanted.

Experimental groups. Donor cells were H9 hESC-derived photoreceptor progenitors transfected with AAV2Y444FRHOKpr.GFP and HA-iPSC-derived photoreceptor progenitors transfected with AAV2Y444FRHOKpr.GFP.

In each mouse, one eye was injected subretinally with cells, and the other eye acted as a non-transplant control. Specimens were collected for histology at 1, 2 and 3 weeks post injection.

Cell Transplantation. Host mice were either C3H/HeNHsd (rd1) (Harlan) with total retinal degeneration or wild type mice, aged 10-12 wk (N=16) (n=8 for ESC, n=8 for iPSC). Rd1 mice are a model of aggressive retinal degeneration with loss of all photoreceptors usually at about 21 days of age. Reference can be made to Han et al. Molecular Vision 2013, 19:2579-2589 for a description of the phenotype and underlying genotype of these mice. At the time of transplantation, the rd1 recipient mice were considered blind, as defined in this model system. The negative control was untreated rd1 mice (age-matched, N=8). The positive control was untreated WT mice (age-matched, N=8). Hosts were anesthetized with an i.p. injection of medetomidine hydrochloride (1 mg/kg body weight) and ketamine (60 mg/kg body weight) in sterile water in the ratio of 5:3:42. Pupils were dilated using 1% (wt/vol) tropicamide (Bausch & Lomb) to facilitate transpupillary visualization with an operating microscope (Leica). Cells were transplanted subretinally using a Hamilton syringe and a sharp 34-gauge needle inserted tangentially through the sclera into the subretinal space, creating a long self-sealing scleral tunnel. Under direct vision, the entire bevel was placed within the subretinal space to avoid reflux. The cell suspension was injected, creating a consistently sized superotemporal bleb. To further minimize expulsion of transplanted cells, normalization of intraocular pressure was verified by continuous direct ophthalmoscopy to monitor for the full return of retinal vessel perfusion, optic nerve head perfusion, and corneal clarity before rapid needle withdrawal. Mice were immune-suppressed using Cyclosporin A (50 mg/kg/day) in a 5% fruit cordial 2 days prior to and 3 weeks after transplantation.

Tissue Collection. Mice were perfusion-fixed with 1-4% paraformaldehyde (PFA) in PBS. Retinal sections were prepared by cryoprotecting fixed eyes in 20% (wt/vol) sucrose before embedding in optimum cutting temperature compound (TissueTek) and frozen in isopentane cooled in liquid nitrogen. Cryosections (16-18 μm) were cut and affixed to poly-L-lysine-coated slides. For flat mounts, retinas were dissected free in PBS or collected after calcium imaging and fixed in 4% (wt/vol) PFA overnight.

Histology and Immunohistochemistry. Retinal sections or flat mounts were blocked in 0.01M PBS containing serum and 0.1% Triton-X 100 for 1-3 h before being incubated with primary antibody overnight (flat mounts: 3 d) at 4° C. After rinsing 3×5 min with PBS, sections were incubated with 1:400 appropriate Alexa-tagged secondary antibodies (Molecular Probes, Invitrogen) for 2 h at 4° C., rinsed, and counterstained with Hoechst 33342. Specimens were mounted using ProLong Gold (Invitrogen).

Confocal Microscopy. Retinal sections were viewed on a confocal microscope (Zeiss LSM710). GFP-positive cells were located using epifluorescence illumination before taking a series of XY optical sections. The fluorescence of Hoechst, GFP, DsRed, Alexa-555, Alexa-568, and Alexa-635 was sequentially excited using 350-nm UV, 488-nm argon, and the 543-nm HeNe lasers, as appropriate. Stacks were built to give XY projection images where appropriate, and images were processed using Volocity (Perkin-Elmer), Image J, and Adobe Photoshop CS4 version 11.0.2.

Functional Test. Mice were dark adapted >12 h before experiment and testing was conducted in a dark room. The light source for behavioral assessment consisted of a dim green LED array suspended above the testing apparatus, emitting dim green light centered at 510 nm (~10 lux) to assess rod-mediated function. Tester and scorer were blinded to treatment.

Optomotor Response. Contrast sensitivities and visual acuities of treated and untreated eyes were measured by observing the optomotor responses of mice to rotating sinusoidal gratings. Mice reflexively respond to rotating vertical gratings by moving their head in the direction of grating rotation. The protocol yields independent measures of the acuities of right and left eyes based on the unequal sensitivities of the two eyes to pattern rotation: right and left eyes are most sensitive to counter-clockwise and clockwise rotations, respectively. A double-blind two alternative forced choice procedure was employed, in which the observer was "masked" to both the direction of pattern rotation and to which eye received hESC/hIPSC-derived photoreceptor progenitors.

Briefly, each mouse was placed on a pedestal located in the center of an optokinetic drum with black vertical stripes corresponding to 0.1 cycles per degree (cpd) spatial frequency. Four inward facing LCD computer monitors were used. Mice were observed by an overhead infrared video camera with infrared light source. The drum was illuminated from above by a dim green light (~13 lux). Mice were habituated 24 hr before testing (5 min habituation in spinning drum). Each experimental run consisted of 3 minute clockwise rotation and 3 minute anti-clockwise rotation divided into alternating 30 second periods. Once the mouse became accustomed to the pedestal, a 7 s trial was initiated by presenting the mouse with a sinusoidal striped pattern that rotates either clockwise or counter-clockwise, as determined randomly by the OptoMotry™ software. Involuntary reflex head tracking responses are driven by the left (clockwise rotations) and right (counter-clockwise rotations) eyes, respectively. Visual acuity and contrast sensitivity were measured under scotopic conditions. The observer selected the direction of pattern rotation based on the animal's optomotor response and the monitors returned to 50% gray until the next trial.

Dependent variable. Head tracks. A response was measured when the mouse completed a slow head-tracking motion in the direction of the drum's rotation followed by a rapid repositioning of the head to a central position (data calculated manually, scorer blinded to treatment).

Results

Figure 29:
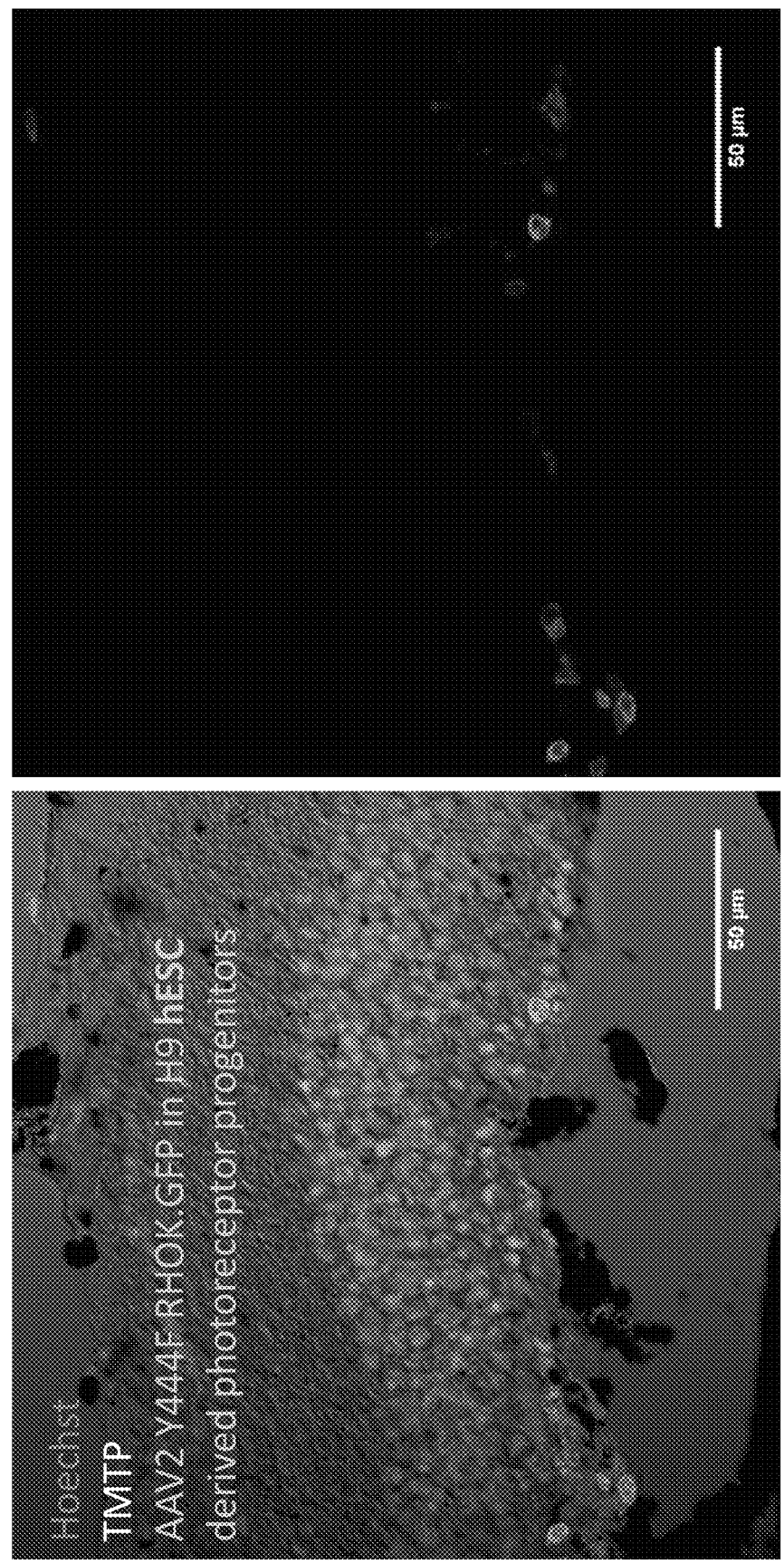
FIG. 29. Cross-sectional images of the retina of rd1 mice 3 weeks post-transplant with hESC-derived photoreceptor progenitors infected with AAV2-Y444F-RHOK.GFP virus. Hoechst positive staining indicates the presence of cells. TMTP is a bright field image. Green cells are GFP-positive human cells as is apparent from the color version of the Figure.
Figure 30:
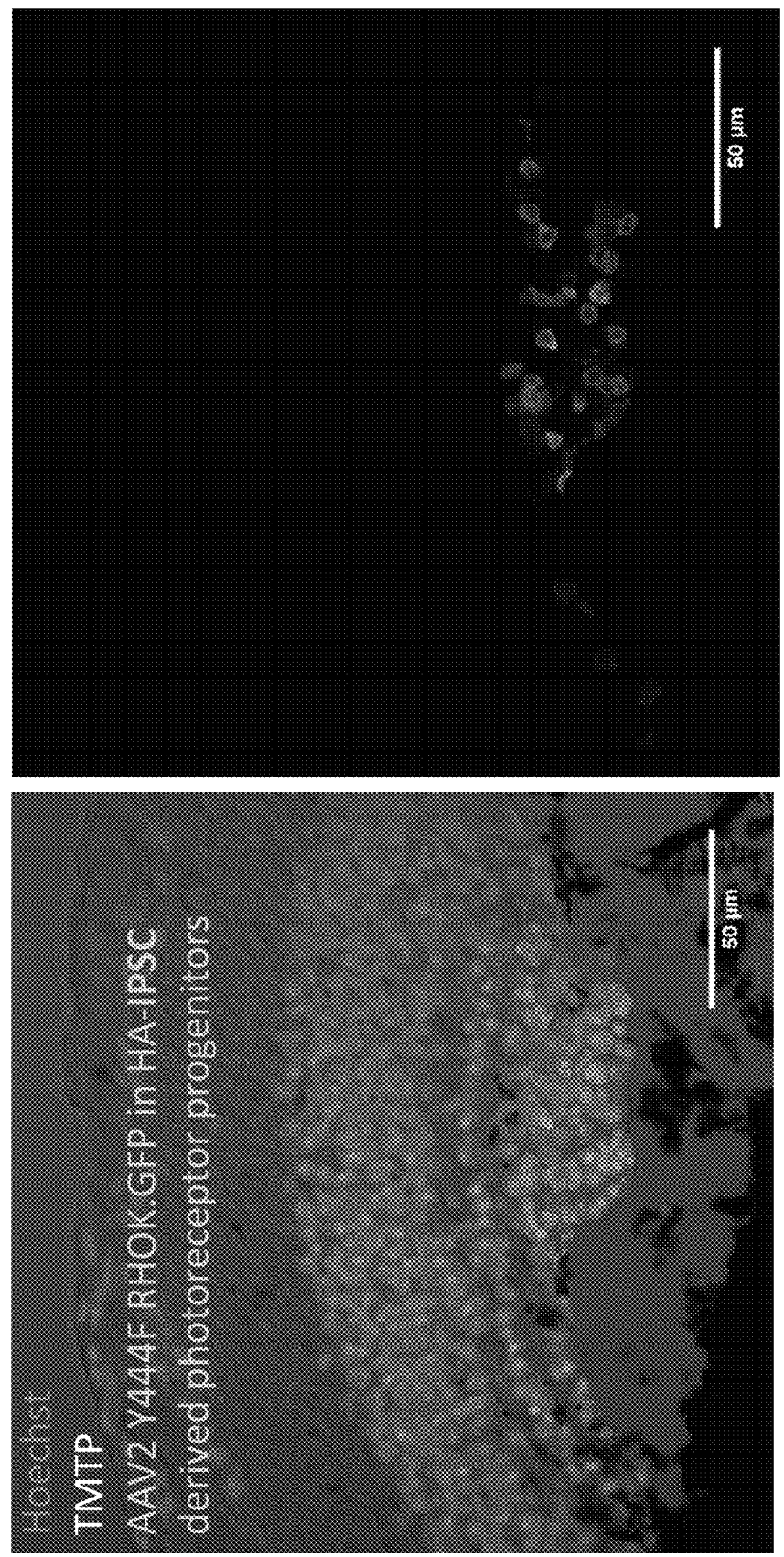
FIG. 30. Cross-sectional images of the retina of rd1 mice 3 weeks post-transplant with hiPSC-derived photoreceptor progenitors infected with AAV2-Y444F-RHOK.GFP virus. Hoechst positive staining indicates the presence of cells. TMTP is a bright field image. Green cells are GFP-positive human cells as is apparent from the color version of the Figure.

Both hESC- and hiPSC-derived photoreceptor progenitors survived and aligned with INL of the mouse retina, as shown in FIGS. 29 and 30 respectively.

Rd1 mice having completely degenerated endogenous photoreceptors (i.e., rd1 mice at time of transplant) showed a significantly higher optokinetic response ($P<0.005$) at 3 weeks post transplantation of human photoreceptor progenitors from both hESC and hiPSC as compared to untreated rd1 mice, as shown in FIG. 31.

The data evidence that both hESC and iPSC derived photoreceptor progenitor cells are able to regenerate at least partial visual acuity in the rd1 mice. Significantly, the data evidence a cell replacement mechanism of action rather than an attenuation of disease progression.

Example 9. Additional Animal Studies in Rd1 Mouse Model: Transplantation of hESC and hiPSC Derived Photoreceptor Progenitors in Rd1 Mice This study assessed the therapeutic potential of photoreceptor progenitors derived from human embryonic and induced pluripotent stem cells (ESCs and iPSCs) using a protocol suitable for future regulatory approvals towards clinical trials. ESCs and iPSCs were cultured using a synchronized differentiation process consisting of four specific stages of defined conditions, resulting in generation of a near-homogeneous population of photoreceptor progenitors. This synchronized differentiation process generates photoreceptor precursors which homogeneously express photoreceptor specific genes. Following transplantation into rd1 mice with end-stage retinal degeneration, these cells differentiate into photoreceptors and form a cell layer connected with host retinal neurons. Visual function is partially restored in treated animals, as evidenced by two visual behavioral tests. The magnitude of improvement is correlated with engrafted cell numbers. These data validate the potential of human pluripotent stem cells for photoreceptor replacement therapies and reveal similar efficacy using either ESCs or iPSCs as source material.

Retinal photoreceptor cell differentiation. To induce neural differentiation, 90% confluent human pluripotent stem cells were split onto Matrigel™ at a 1:25 ratio. When cell colonies grew to about 50-100 cells, cell differentiation was initiated by directly switching cell culture medium from mTESR1 to retinal induction medium (RIM) containing DMEM/F12, N2 and B27 serum-free supplements, 100 units/ml penicillin, 100 μg/ml streptomycin (Life Technologies), 0.45% glucose (Sigma), 20 μg/ml human insulin (Roche), and 50 ng/ml human Noggin (Peprotech) at 37° C./5% $CO_2$. On day 5, the RIM was switched to neural differentiation medium plus (NDM+) containing Neurobasal, N2 and B27 serum-free supplements, 100 units/ml penicillin, 100 μg/ml streptomycin, Glutamax, MEM non-essential amino acid (Life Technologies), 0.45% glucose and 50 ng/ml human Noggin for two weeks. On day 19, cells were mechanically lifted using a scraper (Corning) and plated into ultra-low attachment dishes in NDM minus (NDM−), without Noggin. Cells formed neural spheres in the suspension culture. After four days (day 23), neural spheres were collected and plated on Matrigel™ coated surface in NDM−. Cells were maintained in NDM− until the desired maturation stage for a given experiment.

To generate mature photoreceptor-like cells, photoreceptor progenitors (PhRP) were dissociated into single cells using accutase digestion and plated on Matrigel™ coated dishes at the density of $10^5/cm^2$. Cells were cultured in photoreceptor differentiation medium containing Neurobasal, N2 and B27 serum-free supplements, 100 units/ml penicillin, 100 μg/ml streptomycin, Glutamax, MEM nonessential amino acid (Life Technologies), 0.45% glucose, 10 ng/ml human BDNF, 10 ng/ml human CNTF, 2 μM retinoid acid and 10 μM DAPT for two weeks.

Animals. Wild type (WT) C57BL/6 mice were provided by the Biomedical Sciences division, University of Oxford and C3H/HeNHsd-Pde6b$^{rd1}$ (rd1) mice were purchased from Harlan Laboratories (Hillcrest, UK). Mice were all female and were 10-12 weeks old at the time of intraocular injection. All animals were housed under standard 12:12 hour light/dark cycle, with food and water available ad libitum.

Cell counts. The number of surviving donor cells per eye was determined by quantification of GFP positive cells in non-overlapping sections through each eye. Cells were considered for analysis if they resided in the subretinal space or within the outer nuclear layer, and counted in the entire area between the two or a serrata to account for all surviving cells in each eye. The number of residual host cones was quantified following immunohistochemistry, using an antibody against cone arrestin in four complete histological sections per eye (n=5 eyes per group).

Optomotor response (OMR) Mice were placed on a raised platform in the center of a custom built rotating cylinder with a square-wave grating of black vertical stripes corresponding to 0.1 cycles per degree (cpd) spatial frequency. Mice were dark adapted for >12 hours prior to the procedure and testing was conducted in a dark room, with the cylinder illuminated from above by a custom LED array emitting a dim 510-nm green light (150 nW·cm−2·s−1, approximately 10 lux at the platform). Thorough cleaning with 70% ethanol was conducted before each test and the tester was masked to the treatment. Mice were first habituated to the environment for 1 min during which the drum remained stationary and mice were free to explore the platform. Each experimental run consisted of 1 minute clockwise and 1 minute anticlockwise rotation, divided into alternating 30 second periods (Lipinski et al., 2015). The experimental run was repeated three times for each animal. The rotation of the square-wave grating elicited an optomotor response, with a single response consisting of a slow head-tracking motion in the direction of the drum's rotation followed by a rapid repositioning of the head to a central position. Mean wild-type (WT) response was derived by testing age matched mice (n=8). Behavior was recorded by use of a digital camera mounted directly above the central platform. All experiments were conducted by a single researcher and the number of head tracks was quantified manually by two independent scorers blinded with regards to treatment, and averaged between the three experimental runs.

Light avoidance response. Mice were tested in a partitioned arena with equally sized dark and light chambers connected by an aperture through which the animals were able to transition freely, as previously described (Singh et al., 2013). Briefly, mice were dark adapted >12 h before testing and testing was conducted in a dark room. The light chamber was lit by a LED array suspended above the chamber emitting dim green light centered at 510 nm (maximal illumination of 150 nW·cm−2·s−1, approximately 10 lux at the arena floor). Both chambers were thoroughly cleaned with 70% ethanol before each test and the tester was masked to treatment group. Pupils were dilated 10 min prior to testing with one drop of 1% atropine. Mice were placed in the middle of the lit chamber facing away from the connecting aperture. Each trial lasted 10 min, and all mice were test-naive (a single trial per mouse). Entrance to a chamber was recorded only when all four paws had crossed into that chamber. Light avoidance was measured by the percentage of time spent in the dark chamber. The number of full body transitions between chambers and distance travelled within the lit chamber were recorded as a measure of anxiety-related behavior. Mean wild-type (WT) response was derived by testing age matched mice (n=8). Data were recorded by a digital camera mounted above the lit chamber and calculated by ANY-Maze video tracking software (Version 4.5). All experiments were conducted by a single researcher.

Statistical Analyses. All measures are presented as average and standard error of the mean (SEM).

Results

Robust Generation of Retinal Neural Progenitors from Human Pluripotent Stem Cells Under Defined Serum- and Feeder-Free Condition A simple and efficient method to generate highly-enriched retinal cells from human PSCs using a multi-step strategy was developed. First, hESCs were directly induced to differentiate in retinal induction medium (RIM) followed by exposure to neural differentiation medium (NDM) containing Noggin. After short exposure (usually ≈4 days) to RIM, cells at the edge of colonies became elongated and exhibited a columnar phenotype, and small cells dominated the center of these colonies after further differentiation. A majority of cells at this stage expressed paired box 6 (PAX6), nestin and sex determining region Y-box 2 (SOX2), suggesting they were committed to neural stem cells. Approximately two weeks after differentiation and expansion in NDM, only a few large cells were observed at the edge of neural stem cell colonies. Rapid upregulation of PAX6 and retinal homeobox gene 1 (RX1) transcription factors was observed; >95% and >90% of cells at day 13 expressed PAX6 and RX1, respectively (FIG. 32A), and most of them (>90%) were double positive for PAX6 and RX1 (FIGS. 32B-C). RT-PCR analyses showed expression of PAX6, RX1, LIM Homeobox 2 (LHX2), SIX homeobox 3 (SIX3), SIX homeobox 6 (SIX6) and T-Box 3 (TBX3) in these cells. Real-time quantitative reverse transcription polymerase chain reaction (qRT-PCR) also demonstrated a dramatic decrease in the expression of octamer-binding transcription factor 4 (OCT4) and nanog, two critical pluripotent genes. These results demonstrated a robust differentiation of hESCs towards retinal neural cells with gene profiles corresponding to eye field progenitors (EFP).

After 19-21 days in NDM, EFP cells were collected and plated to form neural spheres in suspension culture. After re-plating on Matrigel™ coated surface, neural spheres rapidly attached to the surface and formed long axon-like neurites. Cell bodies spread out on the Matrigel™ surface probably due to cell migration or active cell proliferation. Cells continually expanded and formed neural rosettes within a week. More than 95% of cells at this stage, including migrated-out neurons or neurons within aggregates, co-expressed PAX6 and Ceh-10 Homeo domain containing homolog (CHX10) (FIG. 32D), suggesting they were retinal neural progenitor cells (RNPC).

To validate the methodology, multiple hESC and iPSC lines, generated with different strategies, were subjected to retinal neuron differentiation and analyzed for the expression of PAX6, RX1 and nestin by flow cytometry. Results demonstrated that all tested cell lines generated a near-homogenous population expressing these markers (data not shown), confirming the robustness of the retinal differentiation platform.

Generation of Photoreceptor Progenitors and Photoreceptor-Like Cells

The ability of PSC-RNPCs to further differentiate into more mature retinal neurons such as photoreceptor progenitors (PhRP) and photoreceptors was then tested. After culturing PSC-RNPCs in NDM without noggin supplementation, cells further differentiated into photoreceptor progenitors, as characterized by gradual loss of proliferative capacity as well as expression of transcription factors involved in photoreceptor development. Cell population doubling time was approximately 10 days at the beginning and extended to 4 weeks by 10 months. After one passage, most cells (>90%) started to express Cone-Rod homeobox (CRX), Neural retina leucine zipper (NRL), retinoid X receptor gamma (RXRγ) and thyroid hormone receptor β2 (TRβ2), transcription factors that are essential for photoreceptor cell fate determination and development. At passage 4 (approximately 3 months in NDM without noggin), dramatic morphological changes were observed. Although a majority of neurons formed short neurites at this stage, neurite branching from the cell body was reduced or absent. Most cells at this stage remained positive for PAX6, NRL, CRX, Nuclear receptor subfamily 2, group E, member 3 (NR2E3) and RXRγ, but lost the expression of CHX10 (FIG. 33A), and less than 10% of them were positive for Ki67, a cellular marker that is strictly associated with cell proliferation. Real-time RT-PCR revealed up-regulation of Achaete-scute family BHLH transcription factor 1 ASCL1 and RAR-related orphan receptor beta (RORβ) genes in these cells (FIG. 33B). Although recoverin protein was detected at low level (FIG. 33C), rhodopsin and opsin proteins remained undetectable, although mRNA levels for both genes were substantially up-regulated in PhRPs in comparison to the levels in RNPCs (FIG. 33D). Both neuN antibody and $2^{nd}$ antibody alone stained negatively in these cells (FIG. 33A). These results indicate that cells were differentiating towards retinal photoreceptors, probably at the stage of PhRPs. Near-homogenous PhRPs were similarly generated from multiple human iPSC lines, which expressed both rod and cone specific transcription factors, NRL and TRβ2. Using multiple hESC and iPSC lines, approximately $1-2\times10^8$ PhRPs were generated from $10^6$ PSCs, therefore a 6-well plate of PSCs ($10-12\times10^6$) could generate $1-2\times10^9$ PhRPs, potentially sufficient for hundreds of patients.

To generate photoreceptor-like cells, PhRPs were further cultured in medium containing retinoic acid, DAPT, Brain-derived neurotrophic factor (BDNF) and ciliary neurotrophic factor (CNTF) for two weeks. Most cells (≈95%) expressed rhodopsin, recoverin and phosphodiesterase 6 alpha (PDE6α), markers of rod photoreceptor (FIG. 34A), and green/red opsin (M-opsin) protein (FIG. 34B), a marker for cone photoreceptors. A majority of cells at this stage co-expressed rhodopsin and M-opsin (FIG. 34B, right panel), indicating PSC-PhRPs possess the potential to differentiate into both rod and cone photoreceptors. Cells expressing photoreceptor-specific markers were also generated from iPS-PhRPs (FIG. 34C).

Since cone and rod photoreceptors are generated from the same pool of retinal neural progenitors at different developmental stages, with L-M-cone and rod photoreceptors being the last retinal neurons generated, PhRPs were continually passaged in vitro for 8 months before commencing differentiation and maturation. After 8 months of culture, PhRPs were able to differentiate into photoreceptor-like cells expressing rod-specific proteins rhodopsin and PDE6α (FIG. 34D) but not cone specific markers.

Human PSC-Derived PhRPs Survived in Severely Degenerated Subretinal Space of Rd1 Mice H9-ESC and HA-iPSC derived PhRPs were selected for further in vivo investigation. In order to discern transplanted human cells following transplantation, PhRP spheres were transduced by a recombinant serotype2 capsid-mutant adeno-associated virus (rAAV2/2 Y444F), expressing GFP under the photoreceptor-specific human rhodopsin kinase promoter. GFP expression was achieved in vitro 7 days post-transduction in 70-90% of cells. To reduce culture time prior to transplantation, and validate the controlled transduction of donor cells, PhRP derived from H9-ESC (ESC-PhRP) were subretinally transplanted to WT mice 48 hours post-transduction. Transplanted human cells, positive for both GFP and human nuclear antigen (HNA), were observed in the subretinal space of WT mice 7 days post-transplantation, without transduction of the host retina by GFP, confirming the expression of GFP was contained to donor cells. Hence for transplantation in the severely degenerate retina, dissociated PhRP were transplanted 48 hours following AAV delivery.

The rd1 mouse model of progressive RP was used. In this model most photoreceptors are lost by 3-4 weeks of age (Lolley et al., 1994) followed by progressive degeneration and loss of the ONL by 6-8 weeks of age (Assawachananont et al., 2014; Cehajic-Kapetanovic et al., 2015; Singh et al., 2013). Human PhRPs were transplanted into the subretinal space of rd1 mice aged 10-12 weeks, at the end-stage of ONL degeneration. To prevent immune-rejection of human cells, immunosuppression with cyclosporine was administered to host mice (West et al., 2010), starting 2 days prior to transplantation and continuing throughout the experiment.

A first group of rd1 mice received transplantation of ESC-PhRPs, a second group received transplantation of iPSC-PhRPs, and a third group received a sham transplantation of PBS (n=8 per group, unilateral injections). To control for cell survival and transfection of the retina by free AAV particles, a further group (n=5) received transplantation of H9-ESC derived retinal neural progenitor cells (RNPCs). All cells were transduced by rAAV2 Y444F.GFP prior to transplantation.

Three weeks post-transplantation, a distinct layer of GFP+ cells was observed in vivo in animals injected with ESC-PhRPs (FIG. 35A) and iPSC-PhRPs (FIG. 35B). Histology revealed GFP+ human cells interposed in the subretinal space of animals in both ESC-PhRP (FIG. 35C) and iPSC-PhRP (FIG. 35D) treated groups three weeks post-transplantation. On average 6.45±1.1% (mean±1 S.E.M) of transplanted ESC-PhRPs and 5.7±1% of iPSC-PhRPs survived per animal, (n=8 specimens each). Under 0.001% of GFP-RNPCs, which were transplanted as a control for cell survival, were observed in the subretinal space of rd1 mice, and were only evident in eyes of 2 of 5 transplanted animals. This confirms that observed GFP+ cells were indeed donor-derived cells and not a result of host retina transduction, and further validates the appropriate developmental stage of PSC-derived PhRP for cell survival following transplantation.

Grafted GFP-positive cells expressed human nuclear antigen and developed processes to interact with host circuitry. However, similar to a previous report of transplantation in the rd1 mouse (Singh et al., 2013), transplanted PhRPs in this study did not adopt normal photoreceptor morphology (FIG. 35E) as described when retinae with a residual ONL were treated with mouse progenitors (Lakowski et al., 2010; MacLaren et al., 2006; Pearson et al., 2012; Yao et al., 2011) or human cells (Lamba et al., 2009).

Transplanted Human PSC-Derived PhRPs Mature In Vivo

Three weeks post-transplantation, ESC-PhRPs and iPSC-PhRPs examined by immunohistochemistry expressed mature photoreceptor proteins, including the pan-photoreceptor marker recoverin (FIGS. 36A-B, respectively) and the rod-specific cGMP phosphodiesterase β6 (PDE6β) located in the outer processes of transplanted cells (FIGS. 36C-D). A deficit in this latter phototransduction-enzyme is the underlying cause of retinal degeneration in the rd1 mouse, and thus this confirmed its expression by donor rods. The rod specific protein rhodopsin (FIGS. 36E-F) and cone-specific protein cone arrestin (FIGS. 36G-H) were also expressed in transplanted cells of both treatment groups, and at this stage no co-expression was observed with rod and cone markers. These observations indicate differentiation of human PhRPs towards rod and cone photoreceptor-like cells. Normal photoreceptors signaling can be identified by the synaptic vesicle glycoprotein, synaptophysin between photoreceptor synaptic terminals and host bipolar cells. Three weeks post-transplantation synaptophysin protein was present between the human graft and the host retina, indicated that donor cells are interacting with host circuitry. Host Muller glia (GFAP positive) extended their processes into and formed connection with the engrafted human PhRPs, and grafted cell extended processes into the host INL. Confocal stacks from a whole-retina flatmount demonstrated the morphology and formation of cell processes in transplanted PhRPs 3 weeks after transplantation into the rd1 subretinal space.

Recovery of Basic Visual Function in Animals with End-Stage Retinal Degeneration In order to further assess transplanted cell maturation and integration into host circuitry, treated rd1 mice were analyzed for changes in basic behavioral function. Behavioral testing was conducted after dark adaptation and using dim 510-nm illumination to target transplanted rod cells.

The presence of an optomotor response (OMR) to a rotating grating was assessed, by adapting a previous protocol (Lipinski et al., 2015). The test animal is placed in the center of a rotating striped drum. An OMR is recorded when the animal turns its head to track the rotating grating. Tracking in each direction is independently driven by one eye (Harvey et al., 1997); an OMR elicited by rotation in a clockwise direction is driven by the left eye, and a response to anti-clockwise rotation is driven by the right eye (the treated eye in this study) (FIG. 37A). Significant improvement in OMR was found in treated eyes compared to untreated eyes of the same animals transplanted with ESC-PhRPs ($t=2.86$, $p<0.05$) and iPSC-PhRPs ($t=5.02$, $p<0.01$), but not in the sham treatment group ($t=0.31$, ns) (FIG. 37B). A significant difference was also found between the three treatment groups in the number of treated eye-derived head tracks ($F=7.8$, $p<0.01$), with post hoc analysis revealing improvements in ESC-PhRP ($p<0.05$) and iPSC-PhRP ($p<0.01$) groups compared to sham (FIG. 37B).

Behavioral performance was correlated to the number of positively identified human cells for each animal, and a positive correlation was found between the number of GFP+ cells and performance in OMR for both ESC-PhRP ($R^2=0.626$, $F=10.0$, $p<0.05$; FIG. 37C) and iPSC-PhRP ($R^2=0.518$, $F=6.45$, $p<0.05$; FIG. 37D) treated animals.

To qualify further the observed behavior, a light avoidance assay was conducted, as previously described (Singh et al., 2013), where animals could transition between light and dark compartments of a test arena (FIG. 37E); in this test, the degree of light avoidance is measured to infer visual function. Here, animals in the three treatment groups did not differ in their tendency to avoid light (ANOVA, $F=1.4$, $p=0.261$ (ns); FIG. 37F) or in anxiety-related behavior. However, since there was a similar trend to that observed in the OMR experiment, the light avoidance behavior was qualified to the number of engrafted cells in each animal. As with the OMR, the number of engrafted cells in individual animals was found to be strongly correlated with light avoidance behavior in both ESC-PhRP ($n=8$, $R^2=0.729$, $F=16.1$, $p<0.01$; FIG. 37G) and iPSC-PhRP ($n=8$, $R^2=0.612$, $F=9.46$, $p<0.05$; FIG. 37H) treated animals. Since light avoidance behavior is driven by light-intensity, which might have a threshold effect to the number of light-sensitive cells, a sub-analysis of the three groups was performed, including only animals with above-median number of surviving cells (top 50%) in the treated groups. In this case, a difference was observed between treatment groups ($X^2=6.0$, $p=0.041$) with an increase in light avoidance in both ESC-PhRP ($n=4$, $p<0.05$) and iPSC-PhRP ($n=4$, $p<0.05$) treated animals compared to sham treatment (FIG. 37I).

In order to exclude the possibility that the functional improvements presented here were due to a non-specific trophic effect on residual host cone-photoreceptors, remaining cones were examined histologically by staining for cone-arrestin. Some residual cones were present in PSC-treated and sham groups; however remaining cones were morphologically abnormal, with inner and outer segments being absent. The number of residual cones did not differ between ESC-PhRP, iPSC-PhRP or sham treatment groups (one way ANOVA, $n=5$ per group, $F=0.56$, $p=0.58$, ns). These data suggest that PhRP transplantation had no obvious protective effect on the morphology of host cones, or on the number of cones in the host retina.

Discussion

Collectively, the data presented show that PhRP cells can be derived from multiple human ESC and iPSC lines. PhRP cells transplanted in the severely degenerated retina, formed a new layer, replacing the degenerated ONL and became immuno-positive for phototransduction proteins, adopting a morphology consistent with generating a primitive outer segment. The restoration of basic behavioral light responses correlated to the number of engrafted cells in the subretinal space.

A completely serum-free and feeder-free direct differentiation system efficiently supports development of functional PhRPs from human PSCs. The synchronized differentiation process may be used to reproducibly generate highly enriched retinal PhRPs on a large scale from a range of human PSC lines. This system is amenable to the development of an in vitro GMP-compliant retinal cell manufacturing protocol for future preclinical and human studies. In particular, this differentiation method allows generation of PhRPs at different development stages, which could be used to target various retinal degeneration diseases at different progression stages. For example, the differentiation process of human ESC and iPSC lead to stepwise differentiation into EFPs, RNPCs, PhRPs and photoreceptor-like cells that homogeneously express cell-specific genes without further sorting.

Human ESC and iPSC derived PhRPs were subretinally transplanted in the rd1 mouse model of end-stage RP. PhRPs were transplanted in this fast degeneration model at 10-12 weeks of age, a time point in which there is no remaining ONL (Assawachananont et al., 2014; Singh et al., 2013). Robust cell survival and in vivo expression of photoreceptor markers by transplanted cells suggest that the severely damaged retina is a permissive space for human cell maturation. Survival and maturation in the completely degenerate retina has been achieved by transplantation of mouse primary cells in suspension (Singh et al., 2013) or mouse PSC-derived 3D retinal sheets (Assawachananont et al., 2014), but has not been shown before using human derived cells.

An improvement was found in optomotor response in treated animals which was of a similar magnitude using either ESC or iPSC derived cells, corroborating in vitro observations of similar differentiation efficacy in these cell lines. Both the OMR response and light avoidance behavior correlated with the numbers of surviving donor cells.

REFERENCES

Assawachananont, J., Mandai, M., Okamoto, S., Yamada, C., Eiraku, M., Yonemura, S., Sasai, Y., and Takahashi, M. (2014). Transplantation of embryonic and induced pluripotent stem cell-derived 3D retinal sheets into retinal degenerative mice. Stem cell reports 2, 662-674.

Barber, A. C., Hippert, C., Duran, Y., West, E. L., Bainbridge, J. W., Warre-Cornish, K., Luhmann, U. F., Lakowski, J., Sowden, J. C., Ali, R. R., et al. (2013). Repair of the degenerate retina by photoreceptor transplantation. Proceedings of the National Academy of Sciences of the United States of America 110, 354-359.

Busskamp, V., Duebel, J., Balya, D., Fradot, M., Viney, T. J., Siegert, S., Groner, A. C., Cabuy, E., Forster, V., Seeliger, M., et al. (2010). Genetic reactivation of cone photoreceptors restores visual responses in retinitis pigmentosa. Science (New York, N.Y.) 329, 413-417.

Cehajic-Kapetanovic, J., Eleftheriou, C., Allen, Annette E., Milosavljevic, N., Pienaar, A., Bedford, R., Davis, Katherine E., Bishop, Paul N., and Lucas, Robert J. (2015). Restoration of Vision with Ectopic Expression of Human Rod Opsin. Current Biology 25, 2111-2122.

Cornish, E. E., Xiao, M., Yang, Z., Provis, J. M., and Hendrickson, A. E. (2004). The role of opsin expression and apoptosis in determination of cone types in human retina. Experimental eye research 78, 1143-1154.

Cramer, A. O., and MacLaren, R. E. (2013). Translating induced pluripotent stem cells from bench to bedside: application to retinal diseases. Current gene therapy 13, 139-151.

Dowling, J. E. (2012). The retina: an approachable part of the brain, Rev. edn (Cambridge, Mass.: Belknap Press of Harvard University Press).

Eberle, D., Santos-Ferreira, T., Grahl, S., and Ader, M. (2014). Subretinal transplantation of MACS purified photoreceptor precursor cells into the adult mouse retina. Journal of visualized experiments: JoVE, e50932.

Eberle, D., Schubert, S., Postel, K., Corbeil, D., and Ader, M. (2011). Increased integration of transplanted CD73-positive photoreceptor precursors into adult mouse retina. Investigative ophthalmology & visual science 52, 6462-6471.

Eiraku, M., and Sasai, Y. (2012). Mouse embryonic stem cell culture for generation of three-dimensional retinal and cortical tissues. Nature protocols 7, 69-79.

Gonzalez-Cordero, A., West, E. L., Pearson, R. A., Duran, Y., Carvalho, L. S., Chu, C. J., Naeem, A., Blackford, S. J., Georgiadis, A., Lakowski, J., et al. (2013). Photoreceptor precursors derived from three-dimensional embryonic stem cell cultures integrate and mature within adult degenerate retina. Nature biotechnology 31, 741-747.

Gouras, P., Du, J., Kjeldbye, H., Yamamoto, S., and Zack, D. J. (1992). Reconstruction of degenerate rd mouse retina by transplantation of transgenic photoreceptors. Investigative ophthalmology & visual science 33, 2579-2586.

Haider, N. B., Jacobson, S. G., Cideciyan, A. V., Swiderski, R., Streb, L. M., Searby, C., Beck, G., Hockey, R., Hanna, D. B., Gorman, S., et al. (2000). Mutation of a nuclear receptor gene, NR2E3, causes enhanced S cone syndrome, a disorder of retinal cell fate. Nature genetics 24, 127-131.

Hartong, D. T., Berson, E. L., and Dryja, T. P. (2006). Retinitis pigmentosa. Lancet 368, 1795-1809.

Harvey, R. J., De'Sperati, C., and Strata, P. (1997). The early phase of horizontal optokinetic responses in the pigmented rat and the effects of lesions of the visual cortex. Vision research 37, 1615-1625.

Hirami, Y., Osakada, F., Takahashi, K., Okita, K., Yamanaka, S., Ikeda, H., Yoshimura, N., and Takahashi, M. (2009). Generation of retinal cells from mouse and human induced pluripotent stem cells. Neuroscience letters 458, 126-131.

Jin, Z. B., Okamoto, S., Xiang, P., and Takahashi, M. (2012). Integration-free induced pluripotent stem cells derived from retinitis pigmentosa patient for disease modeling. Stem cells translational medicine 1, 503-509.

Koso, H., Minami, C., Tabata, Y., Inoue, M., Sasaki, E., Satoh, S., and Watanabe, S. (2009). CD73, a novel cell surface antigen that characterizes retinal photoreceptor precursor cells. Investigative ophthalmology & visual science 50, 5411-5418.

Kwan, A. S., Wang, S., and Lund, R. D. (1999). Photoreceptor layer reconstruction in a rodent model of retinal degeneration. Experimental neurology 159, 21-33.

La Torre, A., Lamba, D. A., Jayabalu, A., and Reh, T. A. (2012). Production and transplantation of retinal cells from human and mouse embryonic stem cells. Methods Mol Biol 884, 229-246.

Lakowski, J., Baron, M., Bainbridge, J., Barber, A. C., Pearson, R. A., Ali, R. R., and Sowden, J. C. (2010). Cone and rod photoreceptor transplantation in models of the childhood retinopathy Leber congenital amaurosis using flow-sorted Crx-positive donor cells. Human molecular genetics 19, 4545-4559.

Lakowski, J., Han, Y. T., Pearson, R. A., Gonzalez-Cordero, A., West, E. L., Gualdoni, S., Barber, A. C., Hubank, M., Ali, R. R., and Sowden, J. C. (2011). Effective transplantation of photoreceptor precursor cells selected via cell surface antigen expression. Stem cells (Dayton, Ohio) 29, 1391-1404.

Lamba, D. A., Gust, J., and Reh, T. A. (2009). Transplantation of human embryonic stem cell-derived photoreceptors restores some visual function in Crx-deficient mice. Cell stem cell 4, 73-79.

Lamba, D. A., Karl, M. O., Ware, C. B., and Reh, T. A. (2006). Efficient generation of retinal progenitor cells from human embryonic stem cells. Proceedings of the National Academy of Sciences of the United States of America 103, 12769-12774.

Lamba, D. A., McUsic, A., Hirata, R. K., Wang, P. R., Russell, D., and Reh, T. A. (2010). Generation, purification and transplantation of photoreceptors derived from human induced pluripotent stem cells. PloS one 5, e8763.

Lipinski, D., Barnard, A., Singh, M., Martin, C., Lee, E., Davies, W., and MacLaren, R. (2015). CNTF gene therapy confers lifelong neuroprotection in a mouse model of human retinitis pigmentosa. Mol Therapy, in press.

Lolley, R. N., Rong, H., and Craft, C. M. (1994). Linkage of photoreceptor degeneration by apoptosis with inherited defect in phototransduction. Investigative ophthalmology & visual science 35, 358-362.

Luo, J., Baranov, P., Patel, S., Ouyang, H., Quach, J., Wu, F., Qiu, A., Luo, H., Hicks, C., Zeng, J., et al. (2014). Human retinal progenitor cell transplantation preserves vision. The Journal of biological chemistry 289, 6362-6371.

MacLaren, R. E., Pearson, R. A., MacNeil, A., Douglas, R. H., Salt, T. E., Akimoto, M., Swaroop, A., Sowden, J. C., and Ali, R. R. (2006). Retinal repair by transplantation of photoreceptor precursors. Nature 444, 203-207.

Mellough, C. B., Sernagor, E., Moreno-Gimeno, I., Steel, D. H., and Lako, M. (2012). Efficient stage-specific differentiation of human pluripotent stem cells toward retinal photoreceptor cells. Stem Cells 30, 673-686.

Meyer, J. S., Shearer, R. L., Capowski, E. E., Wright, L. S., Wallace, K. A., McMillan, E. L., Zhang, S. C., and Gamm, D. M. (2009). Modeling early retinal development with human embryonic and induced pluripotent stem cells. Proceedings of the National Academy of Sciences of the United States of America 106, 16698-16703.

Nakagawa, M., Koyanagi, M., Tanabe, K., Takahashi, K., Ichisaka, T., Aoi, T., Okita, K., Mochiduki, Y., Takizawa, N., and Yamanaka, S. (2008). Generation of induced pluripotent stem cells without Myc from mouse and human fibroblasts. Nature biotechnology 26, 101-106.

Osakada, F., Ikeda, H., Mandai, M., Wataya, T., Watanabe, K., Yoshimura, N., Akaike, A., Sasai, Y., and Takahashi, M. (2008). Toward the generation of rod and cone photoreceptors from mouse, monkey and human embryonic stem cells. Nature biotechnology 26, 215-224.

Osakada, F., Jin, Z. B., Hirami, Y., Ikeda, H., Danjyo, T., Watanabe, K., Sasai, Y., and Takahashi, M. (2009). In vitro differentiation of retinal cells from human pluripotent stem cells by small-molecule induction. Journal of cell science 122, 3169-3179.

Pearson, R. A., Barber, A. C., Rizzi, M., Hippert, C., Xue, T., West, E. L., Duran, Y., Smith, A. J., Chuang, J. Z., Azam, S. A., et al. (2012). Restoration of vision after transplantation of photoreceptors. Nature 485, 99-103.

Punzo, C., and Cepko, C. (2007). Cellular responses to photoreceptor death in the rd1 mouse model of retinal degeneration. Investigative ophthalmology & visual science 48, 849-857.

Schwartz, S. D., Hubschman, J. P., Heilwell, G., Franco-Cardenas, V., Pan, C. K., Ostrick, R. M., Mickunas, E., Gay, R., Klimanskaya, I., and Lanza, R. (2012). Embryonic stem cell trials for macular degeneration: a preliminary report. Lancet 379, 713-720.

Schwartz, S. D., Regillo, C. D., Lam, B. L., Eliott, D., Rosenfeld, P. J., Gregori, N. Z., Hubschman, J. P., Davis, J. L., Heilwell, G., Spirn, M., et al. (2015). Human embryonic stem cell-derived retinal pigment epithelium in patients with age-related macular degeneration and Stargardt's macular dystrophy: follow-up of two open-label phase 1/2 studies. Lancet 385, 509-516.

Singh, M. S., Charbel Issa, P., Butler, R., Martin, C., Lipinski, D. M., Sekaran, S., Barnard, A. R., and MacLaren, R. E. (2013). Reversal of end-stage retinal degeneration and restoration of visual function by photoreceptor transplantation. Proceedings of the National Academy of Sciences of the United States of America 110, 1101-1106.

Song, W. K., Park, K. M., Kim, H. J., Lee, J. H., Choi, J., Chong, S. Y., Shim, S. H., Del Priore, L. V., and Lanza, R. (2015). Treatment of Macular Degeneration Using Embryonic Stem Cell-Derived Retinal Pigment Epithelium: Preliminary Results in Asian Patients. Stem cell reports.

Stingl, K., Bartz-Schmidt, K. U., Besch, D., Braun, A., Bruckmann, A., Gekeler, F., Greppmaier, U., Hipp, S., Hortdorfer, G., Kernstock, C., et al. (2013). Artificial vision with wirelessly powered subretinal electronic implant alpha-IMS. Proceedings Biological sciences/The Royal Society 280, 20130077.

Sun, J., Mandai, M., Kamao, H., Hashiguchi, T., Shikamura, M., Kawamata, S., Sugita, S., and Takahashi, M. (2015). Protective effects of human iPS-derived retinal pigmented epithelial cells in comparison with human mesenchymal stromal cells and human neural stem cells on the degenerating retina in rd1 mice. Stem cells (Dayton, Ohio), n/a-n/a.

Swaroop, A., Kim, D., and Forrest, D. (2010). Transcriptional regulation of photoreceptor development and homeostasis in the mammalian retina. Nature reviews Neuroscience 11, 563-576.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tucker, B. A., Park, I. H., Qi, S. D., Klassen, H. J., Jiang, C., Yao, J., Redenti, S., Daley, G. Q., and Young, M. J. (2011). Transplantation of adult mouse iPS cell-derived photoreceptor precursors restores retinal structure and function in degenerative mice. PloS one 6, e18992.

West, E. L., Pearson, R. A., Barker, S. E., Luhmann, U. F., Maclaren, R. E., Barber, A. C., Duran, Y., Smith, A. J., Sowden, J. C., and Ali, R. R. (2010). Long-term survival of photoreceptors transplanted into the adult murine neural retina requires immune modulation. Stem cells (Dayton, Ohio) 28, 1997-2007.

Xiao, M., and Hendrickson, A. (2000). Spatial and temporal expression of short, long/medium, or both opsins in human fetal cones. The Journal of comparative neurology 425, 545-559.

Yao, J., Feathers, K. L., Khanna, H., Thompson, D., Tsilfidis, C., Hauswirth, W. W., Heckenlively, J. R., Swaroop, A., and Zacks, D. N. (2011). XIAP therapy increases survival of transplanted rod precursors in a degenerating host retina. Investigative ophthalmology & visual science 52, 1567-1572.

Zrenner, E., Bartz-Schmidt, K. U., Benav, H., Besch, D., Bruckmann, A., Gabel, V.-P., Gekeler, F., Greppmaier, U., Harscher, A., Kibbel, S., et al. (2011). Subretinal electronic chips allow blind patients to read letters and combine them to words. Proceedings of the Royal Society B: Biological Sciences 278, 1489-1497.

The invention claimed is:

1. A method of improving visual acuity in a subject having end stage retinal degeneration caused by loss of photoreceptors, comprising
administering to the sub-retinal space of the subject a preparation of photoreceptor progenitor cells, wherein at least 70% of the cells in the preparation are immunocytochemically PAX6(+) and CHX10(−), wherein the subject is characterized as having eyesight of 20/200 or worse prior to administration, and wherein administration of the preparation results in improved visual acuity.

2. The method of claim 1, wherein the subject is human and the photoreceptor progenitor cells are human.

3. The method of claim 1, wherein the photoreceptor progenitor cells are derived in vitro from pluripotent stem cells.

4. The method of claim 3, wherein the pluripotent stem cells are selected from the group consisting of embryonic stem cells and induced pluripotent stem cells.

5. The method of claim 1, wherein the photoreceptor progenitor cells are HLA-genotypically identical to each other.

6. The method of claim 1, wherein the photoreceptor progenitor cells are genomically identical to each other.

7. The method of claim 1, wherein a majority of the photoreceptor progenitor cells in the preparation is mRNA transcript positive for Nr2e3, Tr2, ROR and NRL as detected by qPCR.

8. The method of claim 1, wherein the photoreceptor progenitor cells express at least 2-fold more, relative to retinal neural progenitor cells, of one or more markers selected from uPA, Tenascin-C, CXCL16, CX3CL1 and Chitinase 3 like-1, as detected by immunoassay of secreted proteins or mRNA transcript levels by qPCR.

9. The method of claim 1, wherein the photoreceptor progenitor cells have replicative capacity to undergo at least 20 population doublings in cell culture with less than 25 percent of the cells undergoing cell death, senescing or differentiating into phenotypically nonphotoreceptor cells by the 20th doubling.

10. The method of claim 1, wherein the photoreceptor progenitor cells have transferrin protein and or transferrin mRNA levels that are at least 25 percent less than glyceraldehyde 3-phosphate dehydrogenase protein or mRNA levels respectively.

11. The method of claim 1, wherein the photoreceptor progenitor cells maintain plasticity to differentiate into both rods and cones.

12. The method of claim 1, wherein the preparation includes less than 1% pluripotent stem cells.

13. The method of claim 1, wherein the photoreceptor progenitor cells are at least 75%, at least 85%, at least 95%, at least 99% or about 100% pure with respect to other cell types.

14. The method of claim 1, wherein the photoreceptor progenitor cells are administered in suspension.

15. The method of claim 1, wherein the photoreceptor progenitor cells are administered on a matrix or a support.

16. The method of claim 1, wherein the photoreceptor progenitor cells are administered at a dose of about $10^3$-$10^4$ cells.

17. The method of claim 1, wherein the subject is characterized as having eyesight worse than 20/200.

18. The method of claim 1, wherein the preparation of photoreceptor progenitor cells is pyrogen-free and mycogen-free.

19. The method of claim 1, wherein the photoreceptor progenitor cells are mRNA transcript positive for recoverin, opsin and rhodopsin.

20. The method of claim 3, wherein the in vitro differentiation of pluripotent stem cells comprises differentiating the pluripotent stem cells into eye field progenitor cells under adherent conditions, and differentiating the eye field progenitor cells into the photoreceptor progenitor cells.

21. The method of claim 1, wherein the photoreceptor progenitor cells are capable of differentiating into photoreceptor cells in vitro.

22. The method of claim 21, wherein the photoreceptor progenitor cells are capable of differentiating differentiate into photoreceptor cells in vitro in the presence of retinoic acid and taurine.

23. The method of claim 21, wherein the photoreceptor cells express rhodopsin, opsin, recoverin, and PDE6a.

* * * * *